United States Patent
Umansky et al.

(10) Patent No.: US 10,246,747 B2
(45) Date of Patent: *Apr. 2, 2019

(54) METHODS OF USING MIRNA FROM BODILY FLUIDS FOR EARLY DETECTION AND MONITORING OF MILD COGNITIVE IMPAIRMENT (MCI) AND ALZHEIMER'S DISEASE (AD)

(71) Applicant: DiamiR, LLC, Princeton, NJ (US)

(72) Inventors: Samuil R. Umansky, Princeton, NJ (US); Kira S. Sheinerman, New York, NY (US); Vladimir Tsivinsky, Sharon, MA (US)

(73) Assignee: DiamiR, LLC, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/390,110

(22) Filed: Dec. 23, 2016

(65) Prior Publication Data

US 2017/0107575 A1    Apr. 20, 2017

Related U.S. Application Data

(62) Division of application No. 14/112,765, filed as application No. PCT/US2012/034025 on Apr. 18, 2012, now Pat. No. 9,556,487.

(60) Provisional application No. 61/546,431, filed on Oct. 12, 2011, provisional application No. 61/478,766, filed on Apr. 25, 2011, provisional application No. 61/476,591, filed on Apr. 18, 2011.

(51) Int. Cl.
*C12Q 1/68* (2018.01)
*C12N 15/113* (2010.01)
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/112* (2013.01); *C12Q 2600/118* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 4,785,507 A | 11/1988 | Miyazaki et al. | |
| 4,829,304 A | 5/1989 | Baird | |
| 4,939,663 A | 7/1990 | Baird | |
| 7,653,509 B2 | 1/2010 | Bagwell | |
| 7,897,356 B2 | 3/2011 | Klass et al. | |
| 7,993,831 B2 | 8/2011 | Latham et al. | |
| 8,486,826 B2 | 7/2013 | Umansky et al. | |
| 8,632,967 B2 | 1/2014 | Kuroda et al. | |
| 8,648,017 B2 | 2/2014 | Umansky et al. | |
| 9,447,471 B2 | 9/2016 | Qu et al. | |
| 9,540,692 B2 | 1/2017 | Xu | |
| 9,605,315 B2 | 3/2017 | Patel et al. | |
| 9,611,511 B2 | 4/2017 | Keller et al. | |
| 9,708,667 B2 | 7/2017 | Yanai et al. | |
| 9,726,676 B2 | 8/2017 | Grabe et al. | |
| 9,790,554 B2 | 10/2017 | Keller et al. | |
| 9,803,242 B2 | 10/2017 | Umansky et al. | |
| 9,809,857 B2 | 11/2017 | Wang | |
| 9,933,440 B2 | 4/2018 | Goetzl | |
| 2007/0161004 A1 | 7/2007 | Brown et al. | |
| 2008/0020390 A1 | 1/2008 | Mitchell et al. | |
| 2008/0139801 A1 | 6/2008 | Umansky et al. | |
| 2008/0171667 A1 | 7/2008 | Brown et al. | |
| 2009/0004668 A1 | 1/2009 | Chen et al. | |
| 2009/0075258 A1 | 3/2009 | Latham et al. | |
| 2009/0081640 A1 | 3/2009 | Umansky et al. | |
| 2009/0176723 A1 | 7/2009 | Brown et al. | |
| 2010/0151480 A1 | 6/2010 | Taylor et al. | |
| 2010/0167937 A1 | 7/2010 | Goldknopf et al. | |
| 2010/0167948 A1 | 7/2010 | Krichevsky et al. | |
| 2010/0184046 A1 | 7/2010 | Klass et al. | |
| 2010/0196426 A1 | 8/2010 | Skog et al. | |
| 2010/0216139 A1 | 8/2010 | Galas et al. | |
| 2010/0227908 A1 | 9/2010 | Cairns | |
| 2010/0267804 A1 | 10/2010 | Port et al. | |
| 2010/0279292 A1 | 11/2010 | Marsh et al. | |
| 2010/0286044 A1 | 11/2010 | Litman et al. | |
| 2010/0323357 A1 | 12/2010 | Nana-Sinkam et al. | |
| 2011/0003704 A1 | 1/2011 | Skog et al. | |
| 2011/0053157 A1 | 3/2011 | Skog et al. | |
| 2011/0053158 A1 | 3/2011 | Mambo et al. | |

(Continued)

FOREIGN PATENT DOCUMENTS

| | | |
|---|---|---|
| CN | 101942502 A | 1/2011 |
| CN | 101962685 A | 2/2011 |

(Continued)

OTHER PUBLICATIONS

See http://www.mirbase.org/cgi-bin/mature.pl?mature_acc=MIMAT0000446, retrieved from the web on Oct. 30, 2017 (Year: 2017).*
Zhao et al (PLoS ONE 5(10):e13735, 2010) (Year: 2010).*
Zampetaki et al (Circ Res. 2010;107:810-817) (Year: 2010).*
Mestdagh et al (Nucl. Acids Res. 36(21):e143, 2008) (Year: 2008).*
Wang (RNA (2009), 15:716-723) (Year: 2009).*
Wu et al (J. Biomed. Biotech. 2011, Article ID 597145, 7 pages (Year: 2011).*
Liu et al (Eur. J Cancer 47: 784-791, Mar. 2011) (Year: 2011).*
Delrieu et al (CNS Drugs 2011; 25 (3): 213-226) (Year: 2011).*

(Continued)

*Primary Examiner* — Richard A Schnizer
(74) *Attorney, Agent, or Firm* — Troutman Sanders LLP

(57) ABSTRACT

Described are methods for early diagnosis and progression monitoring of Mild Cognitive Impairment (MCI) and Alzheimer's Disease (AD) by quantifying neurite and/or synapse miRNAs in bodily fluids.

19 Claims, 53 Drawing Sheets

(56) References Cited

U.S. PATENT DOCUMENTS

| | | |
|---|---|---|
| 2011/0086348 A1 | 4/2011 | Prasad et al. |
| 2011/0111976 A1 | 5/2011 | Fare et al. |
| 2011/0117111 A1 | 5/2011 | Kwon et al. |
| 2011/0117560 A1 | 5/2011 | Spinale et al. |
| 2011/0143360 A1 | 6/2011 | Kuroda et al. |
| 2011/0160285 A1 | 6/2011 | Anderson et al. |
| 2011/0160290 A1 | 6/2011 | Tewari et al. |
| 2012/0034608 A1 | 2/2012 | Zhou et al. |
| 2012/0093936 A1 | 4/2012 | Lindenberg et al. |
| 2012/0184599 A1 | 7/2012 | Marcet et al. |
| 2012/0252693 A1 | 10/2012 | Umansky et al. |
| 2012/0270746 A1 | 10/2012 | Kuroda et al. |
| 2013/0131194 A1 | 5/2013 | Skog et al. |
| 2014/0120545 A1 | 5/2014 | Umansky et al. |
| 2014/0170648 A1 | 6/2014 | Kuroda et al. |
| 2014/0194319 A1 | 7/2014 | Skog et al. |
| 2014/0194613 A1 | 7/2014 | Skog et al. |
| 2014/0256562 A1 | 9/2014 | Umansky et al. |
| 2014/0357507 A1 | 12/2014 | Umansky et al. |
| 2016/0273043 A1 | 9/2016 | Umanksy et al. |
| 2017/0362656 A1 | 12/2017 | Umansky et al. |

FOREIGN PATENT DOCUMENTS

| | | |
|---|---|---|
| EP | 3118334 A1 | 1/2017 |
| EP | 3133147 A1 | 2/2017 |
| JP | 2010536372 A | 12/2010 |
| JP | 2010538653 A | 12/2010 |
| JP | 5624470 B2 | 11/2014 |
| RU | 2367959 C1 | 9/2009 |
| WO | 2005118806 A2 | 12/2005 |
| WO | 2007073737 A1 | 7/2007 |
| WO | 2008/045505 A2 | 4/2008 |
| WO | 2008153692 A2 | 12/2008 |
| WO | 2009009457 A1 | 1/2009 |
| WO | 2009012468 A2 | 1/2009 |
| WO | 2009015357 A1 | 1/2009 |
| WO | 2009025852 A2 | 2/2009 |
| WO | 2009036236 A1 | 3/2009 |
| WO | 2009070653 A1 | 6/2009 |
| WO | 2009100029 A1 | 8/2009 |
| WO | 2009114681 A2 | 9/2009 |
| WO | 2009120877 A2 | 10/2009 |
| WO | 2009132273 A2 | 10/2009 |
| WO | 2009133915 A1 | 11/2009 |
| WO | 2009143379 A2 | 11/2009 |
| WO | 2010054386 A2 | 5/2010 |
| WO | 2010117829 A2 | 10/2010 |
| WO | 2011015720 A1 | 2/2011 |
| WO | 2011057003 A2 | 5/2011 |
| WO | 2012145363 A1 | 10/2012 |
| WO | 2012145409 A1 | 10/2012 |
| WO | 2013036936 A1 | 3/2013 |
| WO | 2015073972 A1 | 5/2015 |
| WO | 2017/120285 A1 | 7/2017 |
| WO | 2017/165458 A1 | 9/2017 |

OTHER PUBLICATIONS

Petersen et al (Neurology 75: 889-897, 2010) (Year: 2010).*
European Communication pursuant to Article 94(3) EPC dated Nov. 6, 2015, which issued during prosecution of European Application No. 10779376.2.
European Search Report Issued in European Application No. EP16192259.6; dated Jan. 16, 2017, 2 pages.
International Preliminary Report on Patentability issued in PCT/US2012/034098 dated Oct. 22, 2013; 15 pages.
Japanese Office Action Issued in Japanese Patent Application No. 2014-506516 dated Apr. 4, 2016 (and English-language translation thereof), 20 pages.
Japanese Office Action issued in Japanese Patent Application No. 2014-506516 dated Mar. 1, 2017.
Liang, Y. "An expression meta-analysis of predicated microRNA targets identifies a diagnostic signature for lung cancer", BMC Med. Genomics, 2008, vol. 1;61, pp. 1-16.
Linder, Kirsten et al., "Circulating microRNAs: emerging biomarkers for diagnosis and prognosis in patients with gastrointestinal cancers", Clinical Science, 2015, vol. 128, pp. 1-15.
Miyachi, M. et al. "Circulating muscle-specifics microRNA, miR-206, as a potential diagnostic marker for rhabdomyosarcoma", Biochem. Biophys. Res. Commun. (2010), vol. 400, p. 89-93.
Sheinerman et al. "Plasma microRNA biomarkers for detection of mild cognitive impairment: biomarker validation study," Aging, Dec. 2013, vol. 5, No. 12, Dec. 2013, pp. 925-938.
Weber, J.A. et al., "The microRNA spectrum in 12 body fluids," Clin. Chem., 2010, vol. 56, pp. 1733-1741.
Kye, M.J. et al., "Somatodendritic microRNAs identified by laser capture and multiplex RT-PCR", RNA (2007), vol. 13, pp. 1224-1234.
Landgraf, Pablo, "A Mammalian microRNA Expression Atlas Based on Small RNA Library Sequencing", Cell (2007), vol. 129(7), pp. 1401-1414.
Laterza, Omar F. et al., "Plasma MicroRNAs as Diagnostically Sensitive and Specific Biomarkers of Tissue Injury", Clinical Chemistry (2009), vol. 55:11, pp. 1-7.
Lee, E.J. et al., "Systematic evaluation of microRNA processing patterns in tissues, cell lines, and tumors", RNA (2008) vol. 14, pp. 35-42.
Liang, Y. et al., "Characterization of microRNA expression profiles in normal human tissues", BMC Genomics (2007), vol. 8, pp. 166-185.
Lin et al., "Multimodal MRI Neuroimaging Biomarkers for Cognitive Normal Adults, Amnestic Mild Cognitive Impairment and Alzheimer's Disease" Neurology Research International vol. 2012, Article ID 907409, 17 pages.
Liu, Da-Zhi et al., "Brain and blood microRNA expression profiling of ischemic stroke, intracerebral hemorrhage, and kainate seizures", J. Cereb. Blood Flow Metab., advance online publication, 2009, doi:10.1038/jcbfm.2009.186, pp. 1-12.
Lodes, Michael J. et al., "Detection of Cancer with Serum miRNAs on an Oligonucleotide Microarray", PLoS ONE (2009), vol. 4(7): e6229.
Londin et al., "Analysis of 13 cell types reveals evidence for the expression of numerous novel primate- and tissue-specific microRNAs," Proc. Natl. Acad. Sci. USA (2015), E1106-E1115.
Low, L.K. et al., "Axon pruning: an essential step underlying the developmental plasticity of neuronal connections", Phil. Trans. R. Soc. B. (2006), vol. 361, pp. 1531-1544.
Lugli, G. et al., "Expression of microRNAs and their precursors in synaptic fractions of adult mouse forebrain", Journal of Neurochemistry (2008), vol. 106, pp. 650-661.
Lugli, G. et al., "File S2. Entire list of measured human, rat and mouse microRNAs by microarray after filtering and normalization", Journal of Neurochemistry, vol. 106,2008.
Maes, Olivier C. et al., "Methodology for Discovery of Alzheimer's Disease Blood-Based Biomarkers", J. Gerantol. A. Biol. Sci. Med. Sci. (2009), vol. 64A, pp. 636-645.
Maes, Olivier C. el al., "MicroRNA: Implications for Alzheimer's Disease and other Human CNS Disorders", Current Genomics (2009), vol. 10, pp. 154-168.
Mapstone et al., "Plasma phospholipids identify antecedent memory impairment in older adults" Nature Medicine 20 (4): 415-418, 2014.
McDonald et al., "Analysis of circulating microRNA: pre-analytical and analytical challenges", Clin. Chem. (2011), vol. 57, pp. 833-840.
McKhann, G.M. et al., "The diagnosis of dementia due to Alzheimer's disease: Recommendations from National Institute on Aging-Alzheimer's Association workgroups on diagnostic guidelines for Alzheimer's disease", Alzheimers Dement. (2011), vol. 7, pp. 263-269.
Miller, G., "Alzheimer's biomarker initiative hits its stride", Science (2009), vol. 326, pp. 386-389.
Mitchell, Patrick S. et al., "Circulating microRNAs as stable blood-based markers for cancer detection" Proc. Natl. Acad. Sci. USA (2008), vol. 105(30): pp. 10513-10518.

(56) References Cited

OTHER PUBLICATIONS

Murayama, S. et al., "The Pathology of Alzheimer's Disease", Clinician (2006), No. 553, pp. 15-19.
Naterna-Naranjo, Orlangie et al., "Identification and quantitative analyses of microRNAs located in the distal axons of sympathetic neurons", RNA (2010), vol. 16, pp. 1516-1529.
Office Action Issued in Japanese Patent Application No. 2014-506501 dated Mar. 16, 2016 (and English-language translation thereof), 15 pages.
Office action issued in European Patent Application No. 10 779376.2, dated Nov. 6, 2015.
Olsen, Line et al., "MicroRNAs Show Mutually Exclusive Expression Patterns in the Brain of Adult Male Rats", PLoS ONE (2009), vol. 4(10):e7225.
Peltier, H.J. et al., "Normalization of microRNA expression levels in quantitative RT-PCR assays: identification of suitable reference RNA targets in normal and cancerous human solid tissues", RNA (2008), vol. 14, pp. 844-852.
Ray, S. et al., "Classification and prediction of clinical Alzheimer's diagnosis based on plasma signaling proteins", Nat. Med. (2007), vol. 13, pp. 1359-1362.
Satoh, "Molecular network of microRNA targets in Alzheimer's disease brains", Exp. Neurol. (2012), vol. 235, pp. 436-446, ePub Sep. 16, 2011.
Satoh, J-i, "MicroRNAs and Their Therapeutic Potential for Human Diseases: Aberrant MicroRNA Expression in Alzheimer's Disease Brain", J. Pharmacol. Sci. (2010), vol. 114, pp. 269-275.
Schipper, et al., "MicroRNA expression in Alzheimer blood mononuclear cells", Gene Regul. Syst. Bio. (2007), vol. 1, pp. 263-274.
Schmand, B. et al., "Value of Neurophysiological Tests, Neuroimaging, and Biomarkers for Diagnosing Alzheimer's Disease in Younger and Older Age Cohorts", J. Am. Geriatr. Soc. (2001), vol. 59, pp. 1705-1710.
Schratt, Gerhard, "microRNAs at the synapse", Nature Reviews Neuroscience (2009), vol. 10, pp. 842-849.
Schratt, Gerhard, M. et al., "A brain-specific microRNA regulates dendritic spine development", Nature (2006), vol. 329, pp. 283-289.
Sempere, Lorenzo F. et al., "Expression profiling of mammalian microRNAs uncovers a subset of brain-expressed microRNAs with possible roles in murine and human neuronal differentiation", Genome Biology (2004), vol. 5:R13, pp. R13.1-R13.11.
Sheinerman et al., "Universal screening test based on analysis of circulating organ-enriched microRNAs: a noval to diagnostic screening", Expert Rev. Mol. Diagn. (2015), vol. 15(3), pp. 329-338.
Sheinerman et al., "Analysis of organ-enriched micro-RNAs in plasma as an approach to development of Universal Screening Test: feasibility study", Journal of Translational Medicine (2013), vol. 11, p. 304.
Sheinerman et al., "Early detection of neurodegenerative diseases" Cell Cycle (2013), vol. 12:1, pp. 1-2.
Sheinerman et al., "Plasma microRNA biomarkers for detection of mild cognitive impairment", Aging (2012), vol. 4, No. 9, pp. 590-605.
Sheinerman et al., "Circulating cell-free microRNA as biomarkers for screening, diagnosis, and monitoring of neurode-generative diseases and other neurologic pathologies", Front. Cell. Neurosci. (2013), vol. 7, Art. 150, pp. 1-10.
Shingara, J. et al., "An optimized isolation and labeling platform for accurate microRNA expression profiling", RNA (2005), vol. 11, pp. 1461-1470.
Skog, J. et al., "Glioblastoma microvesicles transport RNA and proteins that promote tumour growth and provide diagnostic biomarkers", Nat. Cell. Biol. (2008), vol. 10(12), pp. 1470-1476.
Sperling, R.A. et al., "The diagnosis of dementia due to Alzheimer's disease: Recommendations from National Institute on Aging—Alzheimer's Association workgroups on diagnostic guidelines for Alzheimer's disease", Alzheimer's Dement. (2011), vol. 7, pp. 280-292.
Supplementary Figures and Tables from Peltier et al., RNA, 2008, 14:844-852.

Veerla, S. et al., "MiRNA expression in urothelial carcinomas: important roles of miR-10a, miR-222, miR-125b, miR-7 and miR452 for lung stage and metastasis, and frequent homozygous losses of miR-31", International Journal of Cancer (2009), vol. 124, pp. 2236-2242.
Wang, Guo-Kun et al., "Circulating microRNA: a novel potential biomarker for early diagnosis of acute myocardial infarction in humans", European Heart Journal (2010), vol. 31, Issue 6, pp. 659-666.
Wang, Kai et al., "Circulating microRNAs, potential biomarkers for drug-induced liver injury", Proc. Natl. Acad. Sci. USA (2009), vol. 106(11), pp. 402-4407.
Wang, Wang-Xia et al., "The Expression of MicroRNA miR-107 Decreases Early in Alzheimer's Disease and May Accelerate Disease Progression through Regulation of beta-Site Anyloid Precursor Protein-Cleaving Enzyme 1", The Journal of Neuroscience (2008), vol. 28, pp. 1213-1223.
Xu, S. et al., "MicroRNA (miRNA) transcriptome of mouse retina an didentificaton foa sensory organ-specific miRNA cluster", Journal of Biological Chemistry (2007), vol. 282, pp. 25052-25066.
Yoo, et al., "Oxidative Stress Regulated Genes in Nigral Dopaminergic Neuronal Cells: correlation with the Known Pathology in Parkinson's Disease", Molecular Brain Research (2003), vol. 110, pp. 76-84.
Yoshiyama, Y. et al., "Synapse Loss and Microglial Activation Precede Tangles in P301S Tauopathy Mouse Model", Neuron. (2007), vol. 53, pp. 337-351.
Adachi, Taichi et al., "Plasma MicroRNA 499 as a Biomarker of Acute Myocardial Infarction", Clinical Chemistry (2010), vol. 56, No. 7, pp. 1183-1185.
Albert, M.S. et al., "The diagnosis of mild cognitive impairment due to Alzheimer's disease: Recommendations from National Institute on Aging—Alzheimer's Association workgroups on diagnostic guidelines for Alzheimer's disease", Alzheimers Dement. (2011), vol. 7, pp. 270-279.
Australian Office Action Issued in Australian Patent Application No. 2012245628 dated Jun. 8, 2016, 6 pages.
Backes, Christina et al., "A dictionary on microRNAs and their putative target pathways", Nucleic Acids Res (2010), vol. 38, pp. 4476-4486,
Bak, Mads et al., "MicroRNA expression in the adult mouse central nervous system", RNA (2008), vol. 14(3), pp. 432-444.
Bartel, D.P., "MicroRNAs: target recognition and regulatory functions", Cell (2009), vol. 136, pp. 215-233.
Bishop, D.L. et al., "Axon branch removal at developing synapses by axosome shedding", Neuron (2004), vol. 44, pp. 651-661.
Braak et al., "Neuropathological staging of Alzheimer's related changes", Acta Neuropathol. (1991), vol. 82, pp. 239-259.
Brase, Jan C. et al., "Circulating miRNAs are correlated with tumor progression in prostate cancer", International Journal of Cancer (2011), vol. 128(3), pp. 608-616.
Brase, Jan C. et al., "Serum microRNAs as non-invasive biomarkers for cancer", Molecular Cancer, vol. 9, pp. 306-315, 2010.
Bredesen, "mCiRNA-Synaptic Crystal Ball?", Aging (2012), vol. 4, No. 11, pp. 732-733.
Charras, Guillaume T. et al., "Life and times of a cellular bleb", Biophys J. (2008), vol. 94(5), pp. 1836-1853.
Chen, Xi, "Characterization of microRNAs in serum: a novel class of biomarkers for diagnosis of cancer and other diseases", Cell Research (2008), vol. 18, pp. 997-1006.
Chim, Stephen S.C. et al., "Detection and Characterization of Placental MicroRNAs in Maternal Plasma," Clinical Chemistry (2008), vol. 54(3), pp. 482-490.
Chinese Office Action dated Mar. 26, 2015, which issued during prosecution of Chinese Application No. 201280030048.6.
Chinese Office Action dated Jun. 2, 2015, which issued during prosecution of Chinese Application No. 201280030033.X.
Chinese Office Action dated Aug. 5, 2015 in corresponding Application No. 201280030048.6.
Chinese Office Action dated Nov. 24, 2015, which issued during prosecution of Chinese Application No. 201280030048.6.
Chinese Office Action dated Aug. 5, 2015 in corresponding Application No. 201280030048.6 (including English translation).

(56) References Cited

OTHER PUBLICATIONS

Cogswell, John P. et al., "Identification of miRNA Changes in Alzheimer's Disease Brain and CSF Yields Putative Biomarkers and Insights into Disease Pathways", Journal of Alzheimer's Disease (2008), vol. 14, pp. 27-41.
Eaton, BA, et al., "Synapse disassembly", Genes Dev. (2003), vol. 17, pp. 2075-2082.
Edbauer, D., et al., "Regulation of synaptic structure and function by FMRP-associated microRNAs miR-125b and miR-132", Neuron (2010), vol. 65(3), pp. 373-384.
Emery, VO, "Alzheimer disease: are we intervening too late?", J Neural Transm (2011), vol. 118(9), pp. 1361-1378.
European Communication pursuant to Article 94(3) EPC dated Jan. 5, 2016, which issued during prosecution of European Application No. 12773705.4.
European Search Report dated Jan. 26, 2015, which issued during prosecution of European Application No. 12773705.4, which corresponds to the present application.
European Communication pursuant to Article 94(3) EPC dated Jun. 25, 2015, which issued during prosecution of European Application No. 12 774 179.1.
European Communication Pursuant to Article 94(3) EPC dated May 24, 2013, which issued during prosecution of European Application No. 10779376.2.
European Communication pursuant to Article 94(3) EPC dated Aug. 21, 2014, which issued during prosecution of European Application No. 10 779 376.2.
European Search Report dated Oct. 30, 2014, which issued during prosecution of European Application No. 12774179.1.
Fackler, OT et al., "Cell motility through plasma membrane blebbing", J Cell Biol. (2008), vol. 181(6), pp. 879-884.
Geekiyanage et al., "Blood serum miRNA: Non-invasive biomarkers for Alzheimer's disease", Exp Neurol. (2012), vol. 235, pp. 491-496, ePub Dec. 1, 2011.
Gillardon et al. "MicroRNA and proteome expression profiling in early-symptomatic a-synuclein(A30P)-transgenic mice", Proteomics Clinical Applications (2008), vol. 2(5), pp. 697-705.
Griffiths-Jones, S., et al., "miRBase: microRNA sequences, targets and gene nomenclature", Nucleic Acids Res. (2006), vol. 34, Database issue: D140-D144.
Hebert et al. "Alterations of the microRNA network cause neurodegenerative disease", Trends in Neurosciences 2009, 32(4):199-206.
Hebert et al., "Loss of microRNA cluster miR-29a/b-1 in sporadic Alzheimer's disease correlates with increased BACEI/beta-secretase expression", Proc Natl Acad Sci USA (2008), vol. 105, pp. 6415-6420.
Henriksen et al., "The future of blood-based biomarkers for Alzheimer's disease", Alzheimer's & Dementia 10 (2014) pp. 115-131.
Hua et al. "A Catalogue of Glioblastoma and Brain MicroRNAs Identified by Deep Sequencing," OMICS A Journal of Integrative Biology (2012), vol. 16, No. 12, pp. 690-699.
Hua, Y-J. et al., "Identification and target prediction of miRNAs specifically expressed in rat neural tissue", BMC Genomics (2009), vol. 10, pp. 214-225.
Hunter, Melissa Piper, et al., "Detection of microRNA Expression in Human Peripheral Blood Microvesicles", PLoS ONE (2008), vol. 3(11): e3694.
International Search Report and Written Opinion of the International Searching Authority dated Apr. 28, 2015 issued during prosecution of International Application No. PCT/US2014/65959.
International Preliminary Report on Patentability for International Application No. PCT/US2010/055495, dated May 8, 2012.
International Search Report and Written Opinion of the International Searching Authority for International Application No. PCT/US12/34098, dated Jul. 17, 2012.
International Search Report and Written Opinion of the International Searching Authority for International Application No. PCT/US12/34025, dated Sep. 28, 2012.
International Search Report for International Application No. PCT/US2010/055495, dated Jun. 6, 2011.
Ji, Xi et al., "Plasma miR-208 as a Biomarker of Myocardial Injury", Clinical Chemistry (2009), vol. 55(11), pp. 1944-1949.
Kemppainen, et al., "MicroRNAs as biomarkers in blood and other biofluids", poster 2010? [Retrieved from the Internet Sep. 8, 2012: <http://www.asuragen.comipdfs/postersibiomarkers.pdf>].
Koirala, S. et al., "Pruning an Axon Piece by Piece", Neuron (2004), vol. 44, pp. 578-580.
Kosaka, Nobuyoshi et al., "Circulating microRNA in body fluid: a new potential biomarker for cancer diagnosis and prognosis", Cancer Sci. (2010), vol. 101, pp. 2087-2092.
Kosaka, Nobuyoshi et al., "Secretory Mechanisms and Intercellular Transfer of MicroRNAs in Living Cells", J Biol Chem. (2010), vol. 285(23), pp. 17442-17452.
Canadian Office Action Issued in Canadian Patent Application No. 2,833,389, dated Nov. 21, 2017, 4 pages.
Canadian Office Action Issued in Canadian Patent Application No. 2,833,375, dated Nov. 24, 2017, 7 pages.
European Extended Search Report Issued in European Application No. EP14862355.6, dated Jun. 9, 2017, 8 pages.
International Search Report and Written Opinion of the International Searching Authority dated May 8, 2017 issued during prosecution of International Application No. PCT/US2017/012258.
International Search Report and Written Opinion Issued in International Application No. PCT/US2017/23470, dated Jul. 31, 2017, 24 pages.
Issler, O., et al., "Determining the Role of microRNAs in Psychiatric Disorders," Nature Reviews Neuroscience, 2015, vol. 16, pp. 201-212.
Japanese Office Action Issued in Japanese Patent Application No. 2014-506501 dated Apr. 4, 2016 (and English-language translation thereof) 20 pages.
Spelling, R.A., et al., "Toward defining the preclinical stages of Alzheimer's disease: Recommendations from the National Institute on Aging and the Alzheimer's Association workgroup", Alzheimer's & Dementia (2011), pp. 1-13.
Communication pursuant to Rules 161(2) and 162 EPC received for European Patent Application No. 12774179.1, dated Nov. 26, 2013, 3 pages.
Communication pursuant to Rules 70(2) and 70a(2) EPC received for European Patent Application No. 12774179.1, dated Nov. 18, 2014, 1 page.
Extended European Search Report received for European Patent Application No. 16185046.6, dated Nov. 15, 2016, 12 pages.
Final Office Action received for U.S. Appl. No. 13/508,262, dated Jul. 30, 2013, 10 pages.
Final Office Action received for U.S. Appl. No. 14/112,684, dated Apr. 28, 2016, 19 pages.
Final Office Action received for U.S. Appl. No. 14/112,765, dated Oct. 9, 2015, 18 pages.
Final Office Action received for U.S. Appl. No. 15/037,559, dated Apr. 18, 2018, 26 pages.
Gene Cards entry for MIR146A, retrieved from https://www.genecards.org/cgi-bin/carddisp.p;?gene=MIR146A&keywords=mir146 on Apr. 14, 2018.
International Preliminary Report on Patentability received for PCT Patent Application No. PCT/US2012/034025, dated Oct. 31, 2013, 9 pages.
International Preliminary Report on Patentability received for PCT Patent Application No. PCT/US2014/065959, dated Jun. 2, 2016, 15 pages.
Non-Final Office Action received for U.S. Appl. No. 13/508,262, dated Mar. 7, 2013, 12 pages.
Non-Final Office Action received for U.S. Appl. No. 14/112,684, dated Jul. 9, 2015, 23 pages.
Non-Final Office Action received for U.S. Appl. No. 14/112,765, dated Apr. 28, 2015, 15 pages.
Non-Final Office Action received for U.S. Appl. No. 15/037,559, dated Jul. 27, 2017, 14 pages.

(56) References Cited

OTHER PUBLICATIONS

Office Action received for Canadian Patent Application No. 2,780,222, dated Jan. 18, 2018, 5 pages.
Office Action received for Chinese Patent Application No. 201280030033.X, dated Aug. 15, 2016.
Office Action received for Chinese Patent Application No. 201280030033.X, dated Nov. 24, 2015.
Office Action received for Chinese Patent Application No. 201280030048.6, dated Aug. 5, 2014.
Office Action received for European Patent Application No. 12773705.4, dated Dec. 8, 2016, 4 pages.
Office Action received for European Patent Application No. 12773705.4, dated Sep. 16, 2014, 6 pages.
Office Action received for European Patent Application no. 14862355.6, dated Mar. 20, 2018, 5 pages.
Goetz, Christopher G., "The History of Parkinson's Disease: Early Clinical Descriptions and Neurological Therapies", Cold Spring Harb Perspect Med vol. 1, 2011, 15 pages.
Pogue et al., "Micro RNA-125b (miRNA-125b) Function in Astrogliosis and Glial Cell Proliferation", Neuroscience Letters, vol. 476, 2010, pp. 18-22.
Vlaminck et al., "Circulating Cell-Free DNA Enables Noninvasive Diagnosis of Heart Transplant Rejection", Science Translational Medicine, vol. 6, No. 241, Jun. 18, 2014, pp. 1-19.
Non-Final Office Action received for U.S. Appl. No. 15/606,747, dated Jun. 1, 2018, 60 pages.
Boeri, M. et al., "MicroRNA Signatures in Tissues and Plasma Predict Development and Prognosis of Computed Tomography Detected Lung Cancer" PNAS (2011) vol. 108, No. 9, pp. 3713-3718.
Kroh, E.M. et al., "Analysis of Circulating MircoRNA Biomarkers in Plasma and Serum Using Quantitative Reverse Transcription-PCR (qRT-PCR)" Methods (2010) vol. 50, pp. 298-301.
Meyer, S.U. et al., "Normalization Strategies for MircoRNA Profiling Experiments: A 'Normal' Way to a Hidden Layer of Complexity?" Biotechnol. Lett. (2010) vol. 32, pp. 1777-1788.
"MirVana PARIS Kit Instructions" Ambion, Life Technologies (2011) 36 pages total.

\* cited by examiner

| MCI Patient Number | MCI compared to AD | | MCI compared to AMC | | |
|---|---|---|---|---|---|
| | mir-451 / mir-132 | mir-451 / mir-874 | miR-451 / miR-491-5p | miR-7 / miR-491-5p | miR-16 / miR-491-5p |
| 1 | | | | | |
| 2 | | | | | |
| 3 | ▓ | ▓ | ▓ | | |
| 4 | | | | | |
| 5 | ▓ | ▓ | ▓ | | ▓ |
| 6 | | | | | |
| 7 | ▓ | ▓ | ▓ | | |
| 8 | ▓ | ▓ | ▓ | | ▓ |
| 9 | | | | | |
| 10 | | | | ▓ | ▓ |
| 11 | | | | | |
| 12 | | | | | |
| 13 | ▓ | ▓ | ▓ | ▓ | ▓ |
| 14 | ▓ | ▓ | ▓ | ▓ | ▓ |
| 15 | ▓ | ▓ | ▓ | ▓ | ▓ |
| 16 | ▓ | ▓ | ▓ | ▓ | ▓ |
| 17 | | | | | |
| 18 | | | | | |
| 19 | ▓ | ▓ | ▓ | ▓ | ▓ |
| 20 | ▓ | ▓ | ▓ | ▓ | ▓ |

Figure 24

METHODS OF USING MIRNA FROM BODILY FLUIDS FOR EARLY DETECTION AND MONITORING OF MILD COGNITIVE IMPAIRMENT (MCI) AND ALZHEIMER'S DISEASE (AD)

CROSS REFERENCE TO RELATED APPLICATIONS

This application is a divisional of U.S. patent application Ser. No. 14/112,765, filed Oct. 18, 2013, which is a U.S. National Phase application under 35 U.S.C. § 371 of International Patent Application No. PCT/US2012/034025, filed Apr. 18, 2012 and published in English on Oct. 26, 2012 as WO 2012/145363 under PCT Article 21(2), and which claims priority from U.S. Provisional Application Ser. No. 61/476,591 filed on Apr. 18, 2011, U.S. Provisional Application Ser. No. 61/478,766, filed on Apr. 25, 2011, and U.S. Provisional Application Ser. No. 61/546,431 filed on Oct. 12, 2011, all of which are incorporated herein by reference in their entirety.

TECHNICAL FIELD OF THE INVENTION

The present invention is directed to methods for early diagnosis and progression monitoring of Mild Cognitive Impairment (MCI) and Alzheimer's Disease (AD) by quantifying neurite and/or synapse miRNAs in bodily fluids.

BACKGROUND OF THE INVENTION

Alzheimer's disease (AD) is the most common neurodegenerative disease, which comprise a large group of pathologies caused by metabolic changes in brain cells, loss of synapses and other compartments of neurons, and finally neuronal death (for review see *Neurodegenerative diseases: From Molecular Concepts to Therapeutic Targets*. Editors: R. von Bernhardi, N.C. Inestrosa, Nova Publishers, 2008). Due to increased lifespan, neurodegenerative diseases in general and AD in particular have become very common in developed countries. In the US alone, there are currently more than 5.4 million (and 36 million worldwide) people living with AD, and estimated 70-80 million people, who are over 55 years old, are considered to be at risk of developing the disease. In 2011, the annual cost of healthcare services for AD patients in the US was estimated at $183 billion (Rocca, W. A. et al. Alzheimer's & Dementia. 2011, 7:80-93; http://www.alz.org/downloads/Facts_Figures_2011.pdf).
Drug development and successful treatment of AD and other neurodegenerative diseases are significantly complicated by the absence of effective methods for their early diagnosis and monitoring. Development of effective diagnostic methods is further complicated by the strong brain potential to compensate for the dysfunction and loss of neurons over a long period of time. This results in late clinical manifestation of disease symptoms when treatment cannot be very successful due to serious morphologic changes in the brain including the massive loss of neurons. Thus, diagnostic methods based on detection of early events in the disease development are particularly desirable.

Alzheimer's disease is characterized by neuronal death in several disease-specific areas of the brain, such as hippocampus and cortex. However, the neuronal loss is a relatively late event in the disease progression that typically is preceded by synaptic dysfunction, synaptic loss, neurite retraction, and the appearance of other abnormalities such as axonal transport defects (See, e.g., Crews, Masliah, Human Mol Gen., 2010, 19:R12-R20; Bredesen, Molecular Neurodegeneration 2009, 4:27; Nimmrich and Ebert, Rev Neurosci. 2009, 20:1-12; Yoshiyama et al., Neuron. 2007, 53:337-351; Wishart et al., J Neuropathol Exp Neurol. 2006, 65:733-739; Gylys et al., Neurochem Int. 2004; 44:125-131; Conforti et al., Trends Neurosci. 2007, 30:159-166; Revuelta, et al. Am J Alzheimers Dis Other Demen 2008, 23: 97-102). Numerous studies are devoted to description of axon destruction with shedding of membrane-enclosed "axosomes", axon, dendrite and spine pruning, and disassembly of synapses (Goda, Davis, Neuron 2003, 40:243-264; Eaton, Davis, Genes Development, 2003, 17:2075-2082; Koirala, Ko, Neuron, 2004, 44:578-580; Bishop et al., Neuron, 2004, 44:651-661; Low, Cheng, Phil. Trans. R. Soc. B 2006 361, 1531-1544).

Currently there are attempts to develop anti-AD therapeutics capable of restoring dendritic spine density and synapses (Adlard et al., PLoS ONE, 2011, 6:e17669).

The first symptomatic stage of Alzheimer's disease that is manifested by mild clinical symptoms is Mild Cognitive Impairment (MCI), which is usually defined as an intermediate state between normal aging and dementia (DeCarli, Lancet Neurol., 2003, 2:15-21; Stephan et al., Alzheimer's Res Therapy, 2009, 1:1-9; Apostolova et al., Human Brain Mapping, 2010, 31:786-797). On average, MCI patients convert to dementia at a rate of 10-15% annually (Petersen et al., Arch Neurol. 2001, 58:1985-1992; Apostolova et al., Human Brain Mapping, 2010, 31:786-797). However, currently the MCI outcome is not reliably predictable. First, up to 40% of MCI patients revert to normal status (Larrieu et al., Neurology, 2002, 59:1594-1599; Brooks, Loewenstein, Alzheimer's Res Therapy, 2010, 2:28-36), and autopsy studies demonstrate that a substantial percentage of MCI patients do not have evidence of AD pathology (Jicha et al., Arch Neurol, 2006, 63:674-681; Khan, Alkon, Neurobiol. Aging, 2010, 31:889-900). Second, about 20% of MCI patients who convert to dementia are diagnosed not with AD but other neurodegenerative diseases, such as vascular, Lewy body, Huntington, Parkinson, and other dementias (Jicha et al., Arch Neurol, 2006, 63:674-681; Stephan et al., Alzheimer's Res Therapy, 2009, 1:1-9). Third, disease progression varies for AD patients from slow to intermediate and rapid (Doody et al., Alzheimer's Res Therapy, 2010, 2:2-10). Even clinically MCI is not a homogeneous pathology and can be described as two conditions, with amnestic symptoms (aMCI) and without amnestic symptoms (Dlugaj et al., Dement Geriatr Cogn Disord., 2010, 30:362-373; Brooks, Loewenstein, Alzheimer's Res Therapy, 2010, 2:28-36). Some publications have demonstrated that aMCI converts to dementia much more often and is a better predictor of AD (Mariani et al., J Alzheimer's Dis., 2007, 12:23-35; Luck et al., Psychiatr Prax., 2008, 35:331-336; Koivunen et al., Neurology, 2011, 76:1085-1099). However, other authors have not found significant difference in the conversion rate for two MCI forms (Rountree et al., Dement Geriatr Cogn Disord., 2007, 24:476-482).

Currently, diagnosis of AD and other forms of dementia is based on analysis of the patient's cognitive function. As mentioned above, due to effective compensatory mechanisms in the brain, the decrease of cognitive function is usually registered when a disease is in its later stages and fewer treatments are available. Amyloid plaques between neurons, neurofibrillary tau-tangles, and an overall shrinkage of brain tissue are the hallmarks of AD, and there were many attempts to develop diagnostic tests based on these phenomena. New imaging techniques, including in vivo detection of β-amyloid deposition (e.g., positron emission tomography (PET), computed tomography (CT), magnetic resonance imaging (MRI), multiphoton imaging, magnetoencephalography (MEG), electroencephalography (EEG) etc.) (Mucke, Nature, 2009, 461:895-897; Mistur et al., J. Clin. Neurol., 2009, 5:153-166; Miller, Science, 2009, 326: 386-389; Perrin et al., Nature, 2009, 461: 916-922) are becoming increasingly popular, but cannot be used for screening purposes.

The existing diagnostic molecular tests for AD and other forms of dementia can be divided into two groups. The first group is based on analysis of single nucleotide polymorphisms (SNP), which is helpful for predicting a higher risk of a disease but not for diagnostics (Bettens et al., Hum Mol Genet. 2010, 19(R1):R4-R11). The second group uses analysis of proteins involved in AD pathogenesis or brain-specific proteins, such as neural thread protein (NTP), in bodily fluids (Schipper, Alzheimer's & Dementia. 2007, 3:325-332). However, these tests are not sufficiently sensitive and specific. Recently published data have demonstrated high sensitivity of AD detection by measuring concentrations of three protein biomarkers (beta-amyloid protein 1-42, total tau protein, and phosphorylated tau181P protein) in the cerebrospinal fluid (CSF) (Meyer et al., Arch Neurol. 2010, 67:949-956; Fagan A. M. et al. Arch. Neurol, 2011, 68:1137-1144). The high invasiveness of the CSF collection procedure makes such tests impractical and challenging for everyday clinical use. Several groups have reported diagnostic assays for AD based on analysis of a large number of proteins or antibodies in human blood (Ray S. et al. 2007, Nat. Med. 13, 1359-1362; Reddy M. M. et al. 2011, Cell 144, 132-142; Nagele E. et al. 2011, PLoS One 6, e23112), However, other researchers were not able to confirm the results of these studies (Bjorkqvist M et al. 2012, PLoS One 7, e29868).

On the 19$^{th}$ of April, 2011 The National Institute on Aging/Alzheimer's Association provided new Diagnostic Guidelines for Alzheimer's Disease (Khachaturian Z S, 2011 Alzheimer's and Dementia. 7, 253-256). The new guidelines were published in four papers devoted to: (i) classification of the AD phases, namely the dementia phase, the symptomatic pre-dementia phase (MCI), and the asymptomatic, preclinical phase of AD (pre-MCI) (Jack et al., 2011, Alzheimer's and Dementia. 7, 257-262); (ii) Recommendations from NIA for the diagnosis of dementia due to AD (McKhann et al., 2011, Alzheimer's and Dementia. 7, 263-269); (iii) Recommendations from NIA for the diagnosis of MCI due to AD (Albert et al., 2011, Alzheimer's and Dementia. 7, 270-279); and (iv) Recommendations from NIA toward defining pre-MCI (Sperling et al., 2011, Alzheimer's and Dementia. 7, 280-292). The new guidelines stress the current lack of and a great need for reliable biomarkers which can be used for detection of pre-MCI and pre-symptomatic AD, as well as MCI and AD.

Thus, there is a huge need in a non-invasive or minimally invasive molecular test(s) capable to detect MCI or even earlier asymptomatic stages of AD (pre-MCI). Further, it would be even better if such a test could be used for prognosis of the disease outcome and disease and treatment monitoring.

Metabolic changes occurring in AD and other neurodegenerative diseases cause the destruction of spines, dendrites, axons, and synapse loss, and the latter likely induces neuronal death (Bredesen, Molecular Neurodegeneration 2009, 4:27; Crews, Masliah, Human Mol Gen., 2010, 19:R12-R20). Similar processes happen during embryonic brain development. Numerous neurons are trying to establish intercellular contacts, those neurons that do it successfully survive, and other neurons die (Butts et al., Cell Death Differ. 2008, 15:1178-1186; Enokido and Hatanaka, Gan To Kagaku Ryoho. 1994, 21:615-620; Gasic and Nicotera, Toxicol Lett. 2003, 139:221-227).

Axon destruction with shedding of membrane-enclosed "axosomes", axon, dendrite and spine pruning, and disassembly of synapses lead to appearance of cell-free vesicles containing cytoplasmic components of neurons, axons, neurites, spines and synapses, including proteins, RNA and their degradation products. There are other processes leading to liberation of these compounds into the extracellular medium, in particular, blebbing (Charras et al., Biophys. J. 2008, 94:1836-1853; Fackler, Grosse, J. Cell Biol. 2008, 181:879-884), exocytosis (Skog et al. Nat Cell Biol., 2008, 10:1470-1476) and other forms of active secretion (Wang et al. Nucleic Acids Res., 2010, 38:7248-7259; Kosaka et al., J Biol Chem., 2010, 285:17442-17452; Pigati et al., PLoS ONE, 2010, e13515).

MicroRNAs (miRNAs) are a class of non-coding RNAs whose final product is an approximately 22 nt functional RNA molecule. They play important roles in the regulation of target genes by binding to complementary regions of messenger transcripts to repress their translation or regulate degradation (Griffiths-Jones Nucleic Acids Research, 2006, 34, Database issue: D140-D144). Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). There are other classes of less characterized small RNAs (reviewed in Kim, Mol. Cells, 2005, 19: 1-15).

Many of miRNAs are specific to or over-expressed in certain organs/tissues/cells (see, e.g., Hua et al., BMC Genomics, 2009, 10:214; Liang et al., BMC Genomics. 2007, 8:166; Landgraf et al., Cell. 2007, 129:1401-1414; Lee et al., RNA. 2008, 14:35-42).

Some miRNAs, including those that are cell-specific, are enriched in certain cellular compartments, particularly in axons, dendrites and synapses (see, e.g., Schratt et al., Nature. 439:283-289, 2006; Lugli et al., J Neurochem. 106:650-661, 2008; Bicker and Schratt, J Cell Mol Med., 12:1466-1476, 2008; Smalheiser and Lugli, Neuromolecular Med. 11:133-140, 2009; Rajasethupathy, Neuron. 63:714-716, 2009; Kye, RNA 13:1224-1234, 2007; Yu et al., Exp Cell Res. 314:2618-2633, 2008; Cougot, et al., J Neurosci. 28:13793-13804, 2008; Kawahara, Brain Nerve. 60:1437-1444, 2008; Schratt G. Rev Neurosci. 2009; 10:842-849; Pichardo-Casas et al. Brain Research. 1436:20-33, 2012).

Expression and concentrations of miRNAs are regulated by various physiological and pathological signals. Changes in expression of some miRNAs were found in neurons of Alzheimer's and other neurodegenerative disease patients (Hebert and De Strooper, Trends Neurosci. 32:199-206, 2009; Saba et al., PLoS One. 2008; 3:e3652; Kocerha et al., Neuromolecular Med. 2009; 11:162-172; Sethi and Lukiw, Neurosci Lett. 2009, 459:100-104; Zeng, Mol Pharmacol. 75:259-264, 2009; Cogswell et al., Journal of Alzheimer's Disease. 14: 27-41, 2008; Schaefer et al., J. Exp. Med. 204:1553-1558, 2007; Hebert, Proc Natl Acad Sci USA 2008; 105:6415-6420; Wang et al., J Neurosci. 2008, 28:1213-1223; Nelson et al., Brain Pathol. 2008; 18:130-138; Lukiw, Neuroreport. 2007; 18:297-300).

Due to their small size, miRNAs can cross the blood-brain, placental and kidney barriers. miRNA release can be activated by pathology, e.g. malignancy (Pigati et al., PLoS ONE, 2010, e13515). Analysis of cell/tissue-specific miR-NAs in bodily fluids was proposed for detection of in vivo cell death (U.S. Patent Pub. No 20090081640; Laterza et al., Clin Chem. 2009, 55:1977-1983).

Cognitive function testing and brain imaging, which are currently used as main methods for diagnosis of neurodegenerative diseases such as AD, allow only detection of later stages of disease and are not sufficiently specific. There is still a great need in the art to develop methods for early diagnosis of MCI and AD prior to occurrence of major morphological changes and massive neuronal cell death.

SUMMARY OF THE INVENTION

As specified in the Background Section above, there is a great need in a noninvasive or minimally invasive test for early detection and monitoring of Alzheimer's Disease (AD), Mild Cognitive Impairment (MCI), and preceding asymptomatic stages, as well as other neurodegenerative diseases. The present invention addresses this need by providing novel, highly sensitive and noninvasive or minimally invasive diagnostic and monitoring methods based on quantification of synapse and/or neurite miRNAs in bodily fluids. The methods of the present invention allow diagnosis and monitoring of pre-MCI, MCI, AD, and other neurodegenerative diseases prior to occurrence of major morphological changes and massive neuronal cell death and thus have numerous clinical implications. For example, the use of the methods of the present invention can lead to enhanced effectiveness of currently available treatments for neurodegenerative diseases as such treatments could be administered at significantly earlier stages of the diseases. The use of the methods of the present invention can also allow development of new effective therapeutic and/or preventive treatments and can decrease costs and increase efficiency of clinical trials associated with such development (e.g., by simplifying and enhancing certainty in patient selection and stratification, and/or by simplifying and increasing the efficiency of the methods for evaluating drug effect).

In one aspect, the present invention provides a method for detection of pre-MCI or MCI in a subject, which method comprises:

a. measuring the level of at least one synapse or neurite miRNA in a bodily fluid sample collected from the subject;

b. comparing the level of said miRNA in the bodily fluid sample collected from the subject with an age-matched control level of said miRNA, and c. (i) identifying the subject as being afflicted with pre-MCI or MCI when the level of said miRNA in the bodily fluid sample collected from the subject is increased as compared to the age-matched control or (ii) identifying the subject as not being afflicted with pre-MCI or MCI when the level of said miRNA in the bodily fluid sample collected from the subject is not increased as compared to the age-matched control.

In a related aspect, the invention provides a method for detection of pre-MCI or MCI in a subject, which method comprises:

a. measuring the level of a synapse or neurite miRNA in a bodily fluid sample collected from the subject;

b. measuring the level of a normalizer miRNA in the same bodily fluid sample collected from the subject;

c. calculating the ratio of the levels of the miRNAs measured in steps (a) and (b);

d. comparing the ratio of the levels of the miRNAs calculated in step (c) with a corresponding age-matched control ratio, and e. (i) identifying the subject as being afflicted with pre-MCI or MCI when the ratio of the levels of the miRNAs calculated in step (c) is higher than the corresponding age-matched control ratio or (ii) identifying the subject as not being afflicted with pre-MCI or MCI when ratio of the levels of the miRNAs calculated in step (c) is not higher than the corresponding age-matched control ratio.

In another aspect, the invention provides a method for predicting likelihood of progression from pre-MCI to MCI in a subject, which method comprises:

a. measuring the level of at least one synapse or neurite miRNA in two or more bodily fluid samples collected from the subject, wherein the samples have been obtained at spaced apart time points;

b. comparing the level of said miRNA in each of the bodily fluid samples collected from the subject with an age-matched control level of the said miRNA, and c. predicting that the disease in the subject will progress from pre-MCI to MCI if the level of said miRNA is increased compared to the age-matched control in two or more consequently obtained bodily fluid samples collected from the subject.

In one embodiment, the bodily fluid samples can be obtained several months apart, e.g., 1, 3, 6, 12, or 24 months apart, preferably 3-6 months apart.

In a related aspect, the invention provides a method for predicting likelihood of progression from pre-MCI to MCI in a subject, which method comprises:

a. measuring the level a synapse or neurite miRNA in two or more bodily fluid samples collected from the subject, wherein the samples have been obtained at spaced apart time points;

b. measuring the level of a normalizer miRNA in each of the same bodily fluid samples collected from the subject;

c. calculating the ratio of the levels of the miRNAs measured in steps (a) and (b) for each of the bodily fluid samples collected from the subject;

d. comparing the ratio of the levels of the miRNAs calculated in step (c) for each of the bodily fluid samples collected from the subject with a corresponding age-matched control ratio, and e. predicting that the disease in the subject will progress from pre-MCI to MCI if the ratio of the levels of the miRNAs calculated in step (c) is higher than the corresponding age-matched control ratio in two or more consequently obtained bodily fluid samples collected from the subject.

The age-matched control level or age-matched control ratio of the miRNA used in the above methods can be, for example, a predetermined standard (e.g., an art-accepted level or ratio determined using age-matched population with normal cognitive functions).

In a separate aspect, the invention provides a method for detection of brain aging in a subject, which method comprises:

a. measuring the level of at least one synapse or neurite miRNA in a bodily fluid sample collected from the subject;

b. comparing the level of said miRNA in the bodily fluid sample collected from the subject with (i) a control level of said miRNA obtained from the same subject in the past or with (ii) a predetermined young age standard, and c. identifying the subject as being subject to brain aging when the level of said miRNA in the bodily fluid sample collected from the subject is increased as compared to the control (i) or as compared to the predetermined young age standard (ii).

In a related aspect, the invention provides a method for detection of brain aging in a subject, which method comprises:

a. measuring the level of a synapse or neurite miRNA in a bodily fluid sample collected from the subject;

b. measuring the level of a normalizer miRNA in the same bodily fluid sample collected from the subject;

c. calculating the ratio of the levels of the miRNAs measured in steps (a) and (b);

d. comparing the ratio of the levels of the miRNAs calculated in step (c) with (i) a corresponding control ratio obtained from the same subject in the past or with (ii) a predetermined young age standard ratio, and e. identifying the subject as being subject to brain aging when the ratio of the levels of the miRNAs calculated in step (c) is higher than the corresponding control ratio (i) or as compared to the predetermined young age standard ratio (ii).

The predetermined young age standard used in the above two methods can be, for example, an art-accepted level or ratio determined using a relevant young population (e.g., 10-20 y.o., 20-30 y.o, 30-40 y.o., 20-50 y.o.) with normal cognitive functions.

In a further aspect, the invention provides a method for determining the effectiveness of pre-MCI or MCI treatment in a subject, which method comprises:

a. measuring the level of at least one synapse or neurite miRNA in one or more bodily fluid samples collected from the subject obtained prior to initiation of the treatment;

b. measuring the level of said miRNA in one or more bodily fluid samples collected from the subject obtained in the course of or following the treatment;

c. comparing the levels of the miRNA measured in steps (a) and (b), and d. (i) determining that the treatment is effective if the level of the miRNA has decreased in the course of or following the treatment; (ii) determining that the treatment is not effective if the level of miRNA has not decreased in the course of or following the treatment.

In a related aspect, the invention provides a method for determining the effectiveness of pre-MCI or MCI treatment in a subject, which method comprises:

a. measuring the level of at least one synapse or neurite miRNA in one or more bodily fluid samples collected from the subject obtained prior to initiation of the treatment;

b. measuring the level of a normalizer miRNA in the same bodily fluid sample(s) from the subject obtained prior to initiation of the treatment;

c. calculating the ratio of the levels of the miRNAs measured in steps (a) and (b) for each of the bodily fluid samples collected from the subject obtained prior to initiation of the treatment;

d. measuring the level of the same synapse or neurite miRNA in one or more bodily fluid samples collected from the subject obtained in the course of or following the treatment;

e. measuring the level of a normalizer miRNA in the same bodily fluid sample(s) from the subject obtained in the course of or following the treatment;

f. calculating the ratio of the levels of the miRNAs measured in steps (d) and (e) for each of the bodily fluid samples collected from the subject obtained in the course of or following the treatment;

g. comparing the ratio of the levels of the miRNAs calculated in steps (c) and (f), and h. (i) determining that the treatment is effective if the ratio of the levels of the miRNAs calculated in step (f) is lower than the ratio of the levels of the miRNAs calculated in step (c); (ii) determining that the treatment is not effective if the ratio of the levels of the miRNAs calculated in step (f) is not lower than the ratio of the levels of the miRNAs calculated in step (c).

In a separate aspect, the invention provides a method for determining the effectiveness of a treatment to delay brain aging in a subject, which method comprises:

a. measuring the level of at least one synapse or neurite miRNA in one or more bodily fluid samples collected from the subject obtained prior to initiation of the treatment;

b. measuring the level of said miRNA in one or more bodily fluid samples collected from the subject obtained in the course of or following the treatment;

c. comparing the levels of the miRNA measured in steps (a) and (b), and d. (i) determining that the treatment is effective if the level of the miRNA has decreased in the course of or following the treatment; (ii) determining that the treatment is not effective if the level of miRNA has not decreased in the course of or following the treatment.

In a related aspect, the invention provides a method for determining the effectiveness of a treatment to delay brain aging in a subject, which method comprises:

a. measuring the level of at least one synapse or neurite miRNA in one or more bodily fluid samples collected from the subject obtained prior to initiation of the treatment;

b. measuring the level of a normalizer miRNA in the same bodily fluid sample(s) from the subject obtained prior to initiation of the treatment;

c. calculating the ratio of the levels of the miRNAs measured in steps (a) and (b) for each of the bodily fluid samples collected from the subject obtained prior to initiation of the treatment;

d. measuring the level of the same synapse or neurite miRNA in one or more bodily fluid samples collected from the subject obtained in the course of or following the treatment;

e. measuring the level of a normalizer miRNA in the same bodily fluid sample(s) from the subject obtained in the course of or following the treatment;

f. calculating the ratio of the levels of the miRNAs measured in steps (d) and (e) for each of the bodily fluid samples collected from the subject obtained in the course of or following the treatment;

g. comparing the ratio of the levels of the miRNAs calculated in steps (c) and (f), and h. (i) determining that the treatment is effective if the ratio of the levels of the miRNAs calculated in step (f) is lower than the ratio of the levels of the miRNAs calculated in step (c); (ii) determining that the treatment is not effective if the ratio of the levels of the miRNAs calculated in step (f) is not lower than the ratio of the levels of the miRNAs calculated in step (c).

In one embodiment of the above methods for determining treatment effectiveness, the samples can be obtained, e.g., every 1 week, 2 weeks, 1 month, 3 months, 6 months, 12 months, or 24 months during or following the treatment.

In an additional aspect, the invention provides a method for identifying a compound useful for slowing down the progression or treating pre-MCI or MCI, which method comprises:

a. measuring the level of at least one synapse or neurite miRNA in one or more bodily fluid samples collected from a subject having pre-MCI or MCI, wherein said bodily fluid sample(s) is obtained prior to test compound administration;

b. measuring the level of said miRNA in one or more bodily fluid samples collected from the subject obtained following administration of a test compound;

c. comparing the levels of the miRNA measured in steps (a) and (b), and d. (i) identifying that the test compound is useful for slowing down the progression or treating pre-MCI or MCI if the level of the miRNA has decreased after the compound administration; (ii) identifying that the test compound is not useful for slowing down the progression or treating pre-MCI or MCI if the level of miRNA has not decreased after the compound administration.

In a related aspect, the invention provides a method for identifying a compound useful for slowing down the progression or treating pre-MCI or MCI, which method comprises:

a. measuring the level of at least one synapse or neurite miRNA in one or more bodily fluid samples collected from a subject having pre-MCI or MCI, wherein said bodily fluid sample(s) is obtained prior to test compound administration;

b. measuring the level of a normalizer miRNA in the same bodily fluid sample(s) from the subject obtained prior to test compound administration;

c. calculating the ratio of the levels of the miRNAs measured in steps (a) and (b) for each of the bodily fluid samples collected from the subject obtained prior to test compound administration;

d. measuring the level of the same synapse or neurite miRNA in one or more bodily fluid samples collected from the subject obtained following administration of a test compound;

e. measuring the level of a normalizer miRNA in the same bodily fluid sample(s) from the subject obtained following administration of the test compound;

f. calculating the ratio of the levels of the miRNAs measured in steps (d) and (e) for each of the bodily fluid samples collected from the subject obtained following administration of the test compound;

g. comparing the ratio of the levels of the miRNAs calculated in steps (c) and (f), and h. (i) identifying that the test compound is useful for slowing down the progression or treating pre-MCI or MCI if the ratio of the levels of the miRNAs calculated in step (f) is lower than the ratio of the levels of the miRNAs calculated in step (c); (ii) identifying that the test compound is not useful for slowing down the progression or treating pre-MCI or MCI if the ratio of the levels of the miRNAs calculated in step (f) is not lower than the ratio of the levels of the miRNAs calculated in step (c).

In a separate aspect, the invention provides a method for identifying a compound useful for delaying brain aging, which method comprises:

a. measuring the level of at least one synapse or neurite miRNA in one or more bodily fluid samples collected from a subject, wherein said bodily fluid sample(s) is obtained prior to test compound administration;

b. measuring the level of said miRNA in one or more bodily fluid samples collected from the subject obtained following administration of a test compound;

c. comparing the levels of the miRNA measured in steps (a) and (b), and d. (i) identifying that the test compound is useful for delaying brain aging if the level of the miRNA has decreased after the compound administration; (ii) identifying that the test compound is not useful for delaying brain aging if the level of miRNA has not decreased after the compound administration.

In a related aspect, the invention provides a method for identifying a compound useful for delaying brain aging, which method comprises:

a. measuring the level of at least one synapse or neurite miRNA in one or more bodily fluid samples collected from a subject, wherein said bodily fluid sample(s) is obtained prior to test compound administration;

b. measuring the level of a normalizer miRNA in the same bodily fluid sample(s) from the subject obtained prior to test compound administration;

c. calculating the ratio of the levels of the miRNAs measured in steps (a) and (b) for each of the bodily fluid samples collected from the subject obtained prior to test compound administration;

d. measuring the level of the same synapse or neurite miRNA in one or more bodily fluid samples collected from the subject obtained following administration of a test compound;

e. measuring the level of a normalizer miRNA in the same bodily fluid sample(s) from the subject obtained following administration of the test compound;

f. calculating the ratio of the levels of the miRNAs measured in steps (d) and (e) for each of the bodily fluid samples collected from the subject obtained following administration of the test compound;

g. comparing the ratio of the levels of the miRNAs calculated in steps (c) and (f), and h. (i) identifying that the test compound is useful for delaying brain aging if the ratio of the levels of the miRNAs calculated in step (f) is lower than the ratio of the levels of the miRNAs calculated in step (c); (ii) identifying that the test compound is not useful for delaying brain aging if the ratio of the levels of the miRNAs calculated in step (f) is not lower than the ratio of the levels of the miRNAs calculated in step (c).

The above test compound screening methods can also comprise a step of administering the test compound to the subject.

In a separate aspect, the invention provides a method for predicting progression from MCI to dementia stage of AD in a subject which had been diagnosed with MCI, which method comprises:

a. measuring the level of miR-451 in a bodily fluid sample collected from the subject;

b. measuring the level of at least one synapse or neurite miRNA in the same bodily fluid sample;

c. calculating the ratio of the levels of the miRNAs measured in steps (a) and (b);

d. comparing the ratio of the levels of the miRNAs calculated in step (c) with a corresponding age-matched control ratio, and e. determining that the disease in the subject will progress from MCI to dementia stage of AD if the ratio of the levels of the miRNAs calculated in step (c) is higher than the corresponding age-matched control ratio.

In a separate aspect, the invention provides a method for predicting progression from MCI to dementia stage of AD in a subject which had been diagnosed with MCI, which method comprises:

a. measuring the level of at least one of miR-7, miR-125b, and miR-16 in a bodily fluid sample collected from the subject;

b. measuring the level of a normalizer miRNA in the same bodily fluid sample;

c. calculating the ratio of the levels of the miRNAs measured in steps (a) and (b);

d. comparing the ratio of the levels of the miRNAs calculated in step (c) with a corresponding age-matched control ratio, and e. determining that the disease in the subject will progress from MCI to dementia stage of AD if at least one ratio calculated in step (c) is higher than the corresponding age-matched control ratio.

In a related aspect, the invention provides a method for predicting progression from MCI to dementia stage of AD in a subject which had been diagnosed with MCI, which method comprises combination of two biomarker/normalizer miRNA ratios, namely the ratio of miR-451 to synapse or neurite miRNA and the ratio of miR-7, 125b, or miR-16 to a normalizer miRNA, in one test. The disease in the subject will be expected to progress from MCI to dementia stage of AD if both ratios are higher than respective age-matched control ratios.

In a separate aspect, the invention provides a method for monitoring progression from MCI to dementia stage of AD in a subject which had been diagnosed with MCI, which method comprises:

a. measuring the level of miRNA-451 in bodily fluid samples collected from the subject, wherein the samples have been collected at spaced apart time points;

b. comparing the level of miRNA-451 in each of the bodily fluid samples from the subject with a corresponding age-matched control level, and c. determining that the disease in the subject progresses from MCI to AD if the level of miRNA-451 in each of the bodily fluid samples from the subject is higher than the corresponding age-matched control level.

In a related aspect, the invention provides a method for monitoring progression from MCI to dementia stage of AD in a subject which had been diagnosed with MCI, which method comprises:

a. measuring the level of miR-451 in bodily fluid samples collected from the subject, wherein the samples have been collected at spaced apart time points;

b. measuring the level of at least one synapse or neurite miRNA in each of the same bodily fluid samples collected from the subject;

c. calculating the ratio of the levels of the miRNAs measured in steps (a) and (b) for each of the bodily fluid samples collected from the subject;

d. comparing the ratio of the levels of the mRNAs calculated in step (c) for each of the bodily fluid samples collected from the subject with a corresponding age-matched control ratio, and e. determining that the disease in the subject progresses from MCI to dementia stage of AD if the ratio of the miRNAs calculated in step (c) is higher than the corresponding age-matched control ratio for each of the bodily fluid samples collected from the subject.

In a separate aspect, the invention provides a method for monitoring progression from MCI to dementia stage of AD in a subject which had been diagnosed with MCI, which method comprises:

a. measuring the level of at least one of miR-7, 125b, and miR-16 in bodily fluid samples collected from the subject, wherein the samples have been collected at spaced apart time points;

b. measuring the level of a normalizer miRNA in each of the same bodily fluid samples collected from the subject;

c. calculating the ratio of the levels of the miRNAs measured in steps (a) and (b) for each of the bodily fluid samples collected from the subject;

d. comparing the ratio of the levels of the mRNAs calculated in step (c) for each of the bodily fluid samples collected from the subject with a corresponding age-matched control ratio, and e. determining that the disease in the subject progresses from MCI to dementia stage of AD if at least one ratio calculated in step (c) is higher than the corresponding age-matched control ratio for each of the bodily fluid samples collected from the subject.

In a related aspect, the invention provides a method for monitoring progression from MCI to dementia stage of AD in a subject which had been diagnosed with MCI, which method comprises combining two biomarker/normalizer miRNA ratios, namely (i) the ratio of miR-451 to synapse or neurite miRNA and (ii) the ratio of at least one of miR-7, miR-125b, and miR-16 to a normalizer miRNA (e.g., miR-491-5p or the average of two or more normalizers selected from the group consisting of miR-9, miR-127, miR-181a, miR-370, and miR-491-5p), in one test. The disease in the subject will be expected to progress from MCI to AD dementia if both ratios (i) and (ii) are higher than the corresponding age-matched control ratio for each of the bodily fluid samples collected from the subject.

In one embodiment of the above methods, the bodily fluid samples can be collected several months apart, e.g., 1, 3, 6, 12, or 24 months apart, preferably 3-6 months apart.

Non-limiting examples of synapse or neurite miRNAs useful in the methods of the present invention include, e.g., miR-7, miR-25, miR-26a, miR-26b, miR-98, miR-124, miR-125a, miR-125b, miR-128, miR-132, miR-134, miR-137, miR-138, miR-146, miR-154, miR-182, miR-183, miR-200b, miR-200c, miR-218, miR-292-5p, miR-297, miR-322, miR-323-3p, miR-329, miR-325, miR-337, miR-339, miR-345, miR-350, miR-351, miR-369-3, miR-369-5p, miR-381, miR-382, miR-409-3p, miR-425, miR-429, miR-433-5p, miR-446, miR-467, miR-483-3p, miR-485-5p, miR-487b, miR-494, miR-495, miR-496, miR-541, miR-543, miR-656, miR-668, miR-874, miR-889, miR-935, and miR-939.

Preferred examples of synapse or neurite miRNAs useful in the pre-MCI and MCI diagnostic, prognostic and screening methods of the present invention include miR-128, miR-132, miR-874, miR-134, miR-323-3p, miR-382, miR-7, and miR-125b.

Preferred examples of synapse or neurite miRNAs useful in the diagnostic, prognostic and screening methods related to brain aging include miR-128, miR-132, miR-874, miR-134, miR-323-3p, and miR-382.

To increase accuracy in the methods of the invention, it is preferable to use levels of two or more synapse or neurite miRNAs. It is further preferable to verify changes in synapse or neurite miRNA levels in two or more consecutively collected bodily fluid samples.

The normalizer miRNAs useful in the methods of the invention include brain-enriched normalizer miRNAs as well as miRNAs which are expressed in numerous tissues but are not significantly expressed in brain (e.g., miR-10b or miR-141). The methods of the invention encompass the use of single normalizers (e.g., miR-491-5p, miR-370, etc.) as well as the average of two or more normalizers (e.g., two or more normalizers selected from the group consisting of miR-9, miR-127, miR-181a, miR-370, and miR-491-5p).

Brain-enriched normalizer miRNAs useful in the methods of the invention include, for example, neuronal body miR- NAs; miRNAs, which are mainly expressed in brain areas not involved in a pathology being assessed; miRNAs, which are mainly expressed in glial cells; and brain-enriched miRNAs, which expression, secretion or both are downregulated in a pathology being assessed.

Non-limiting examples of brain-enriched normalizer miRNAs useful in the methods of the invention include, e.g., miR-9, miR-181a, miR-127, miR-370, and miR-491-5p, which can be used alone or in combination.

In one specific embodiment (applicable to each of the methods of the present invention), the synapse or neurite miRNA is selected from the group consisting of miR-128, miR-132, and miR-874 (collectively "miR-132 family"), and the normalizer miRNA is selected from the group consisting of miR-491-5p, miR-9, miR-181a, and miR-141.

In another specific embodiment (applicable to each of the methods of the present invention), the synapse or neurite miRNA is selected from the group consisting of miR-134, miR-323-3p, and miR-382 (collectively "miR-134 family"), and the normalizer miRNA is miR-370 or miR-127.

In another specific embodiment (applicable to all methods of the invention, except for methods related to brain aging), the synapse or neurite miRNA is miR-7, and the normalizer miRNA is miR-9, miR-27, miR-181a, miR-370, miR-491-5p, or the average of plasma concentrations of all these normalizers.

In another specific embodiment (applicable to all methods of the invention, except for methods related to brain aging), the synapse or neurite miRNA is miR-125b, and the normalizer miRNA is miR-9, miR-181a, miR-370, miR-491-5p, or the average of plasma concentrations of all these normalizers.

Subjects used in the methods of the present invention include, e.g., humans, veterinary animals and experimental animal models of neurodegenerative diseases or other neuronal pathologies. For diagnostic, prognostic and treatment monitoring methods of the invention, the subject is preferably a human. For screening methods, the subject is preferably an experimental animal.

Non-limiting examples of bodily fluids which can be used in the methods of the invention include, e.g., blood plasma or serum, urine, and saliva. In some embodiments, miRNA is purified from the bodily fluid sample.

In some embodiments, the methods of the invention comprise (e.g., as an initial step) the step of collecting a bodily fluid sample from the subject.

In the methods of the invention, the level of miRNA can be determined using any suitable technique, for example, hybridization, RT-PCR, or sequencing.

In some embodiments, the methods of the invention can further comprise the step of reducing or eliminating degradation of the miRNA.

In some embodiments, the diagnostic methods of the invention can further comprise the step of administering a therapeutic or preventive treatment to the subject that has been diagnosed as having the condition or as being at risk of progression to a more severe condition.

In some embodiments, the diagnostic methods of the invention can further comprise the step of recruiting the subject in a clinical trial.

In conjunction with the above diagnostic and screening methods, the present invention also provides various kits comprising one or more primer and/or probe sets specific for the detection of target miRNA. Such kits can further include primer and/or probe sets specific for the detection of normalizer miRNA. Non-limiting examples of primer or probe combinations in kits are as follows:

1. Primers or probes specific for at least one miRNA selected from the group consisting of miR-7, miR-125b, and miR-16 (optionally, further comprising primers or probes specific for at least one normalizer miRNA selected from the group consisting of miR-491-5p, miR-9, miR-127, miR-181a, and miR-370).

2. Primers or probes specific for miR-451 (optionally, further comprising primers or probes specific for at least one miRNA selected from the group consisting of miR-7, miR-25, miR-26a, miR-26b, miR-98, miR-124, miR-125a, miR-125b, miR-128, miR-132, miR-134, miR-137, miR-138, miR-146, miR-154, miR-182, miR-183, miR-200b, miR-200c, miR-218, miR-292-5p, miR-297, miR-322, miR-323-3p, miR-329, miR-325, miR-337, miR-339, miR-345, miR-350, miR-351, miR-369-3, miR-369-5p, miR-381, miR-382, miR-409-3p, miR-425, miR-429, miR-433-5p, miR-446, miR-467, miR-483-3p, miR-485-5p, miR-487b, miR-494, miR-495, miR-496, miR-541, miR-543, miR-656, miR-668, miR-874, miR-889, miR-935, and miR-939).

3. Primers or probes specific for at least two miRNAs selected from the group consisting of miR-7, miR-25, miR-26a, miR-26b, miR-98, miR-124, miR-125a, miR-125b, miR-128, miR-132, miR-134, miR-137, miR-138, miR-146, miR-154, miR-182, miR-183, miR-200b, miR-200c, miR-218, miR-292-5p, miR-297, miR-322, miR-323-3p, miR-329, miR-325, miR-337, miR-339, miR-345, miR-350, miR-351, miR-369-3, miR-369-5p, miR-381, miR-382, miR-409-3p, miR-425, miR-429, miR-433-5p, miR-446, miR-467, miR-483-3p, miR-485-5p, miR-487b, miR-494, miR-495, miR-496, miR-541, miR-543, miR-656, miR-668, miR-874, miR-889, miR-935, and miR-939 (optionally, further comprising primers or probes specific for at least one normalizer miRNA selected from the group consisting of miR-10b, miR-141, miR-9, miR-127, miR-181a, miR-370, and miR-491-5p).

4. Primers or probes specific for at least one miRNA selected from the group consisting of miR-128, miR-132, miR-874, miR-134, miR-323-3p, miR-382, miR-7, and miR-125b (optionally, further comprising primers or probes specific for at least one normalizer miRNA selected from the group consisting of miR-10b, miR-141, miR-9, miR-127, miR-181a, miR-370, and miR-491-5p).

5. Primers or probes specific for at least one miRNA selected from the group consisting of miR-128, miR-132, and miR-874 (optionally, further comprising primers or probes specific for at least one normalizer miRNA selected from the group consisting of miR-491-5p, miR-9, miR-181a, and miR-141).

6. Primers or probes specific for at least one miRNA selected from the group consisting of miR-134, miR-323-3p, and miR-382 (optionally, further comprising primers or probes specific for at least one normalizer of miR-370 or miR-127).

7. Primers or probes specific for miR-7 (optionally, further comprising primers or probes specific for at least one normalizer miRNA selected from the group consisting of miR-9, miR-27, miR-181a, miR-370, and miR-491-5p).

8. Primers or probes specific for miR-125b (optionally, further comprising primers or probes specific for at least one normalizer miRNA selected from the group consisting of miR-9, miR-181a, miR-370, and miR-491-5p).

Such kits can be useful for direct miRNA detection in bodily fluid samples isolated from patients or can be used on purified RNA samples.

BRIEF DESCRIPTION OF THE DRAWINGS

FIGS. 3A-3C are graphs showing comparison of miRNA concentrations in plasma of MCI patients (MCI) and age-matched controls (AMC). Concentrations of miR-7 (A), miR-128 (B) and miR-134 (C) were normalized per miR-181a.

FIGS. 12A-12G are graphs showing comparison of miRNA concentrations in plasma of MCI and AD patients and age-matched controls. Concentrations of miR-7 (A), miR-128 (B), miR-132 (C), miR-134 (D), miR323-3p (E), miR-382 (F), and miR-874 (G) were normalized per miR-181a.

▨—MCI free patients, as diagnosed by cognitive function testing, who were also determined negative by the plasma miRNA test; ▦—MCI free patients, who were determined positive by the plasma miRNA test; ▢—patients with clinical symptoms of MCI, who were determined negative by the plasma miRNA test; ■—patients with clinical symptoms of MCI, who were determined positive by the plasma miRNA test. miRNA isolated from the sample collected from Patient 1 at time point 0 did not pass quality control (QC) because of strong inhibition of RT-PCR; no analysis was performed for this sample.

FIGS. 20A-20G are graphs showing comparison of miR-451 concentrations in plasma of MCI (MCI) and AD patients (AD) and age-matched controls (AMC). Concentrations of miR-451 were normalized per miR-141 (A), miR-9 (B), miR-181a (C), miR-370 (D), miR-491-5p (E), the average of 5 normalizers miR-9, miR-127-3p, miR-181a, miR-370, and miR-491-5p (F), and the average (AVER) of all 15 miRNA (see Example 3) analyzed in the study (G) and presented in relative units (ordinate axis).

Figure 21A:
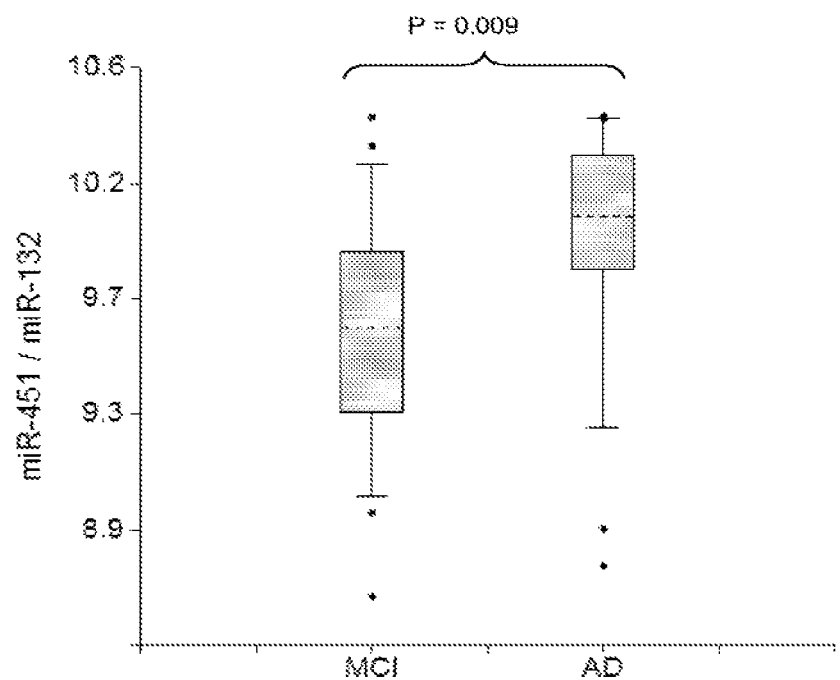
Figure 21B:
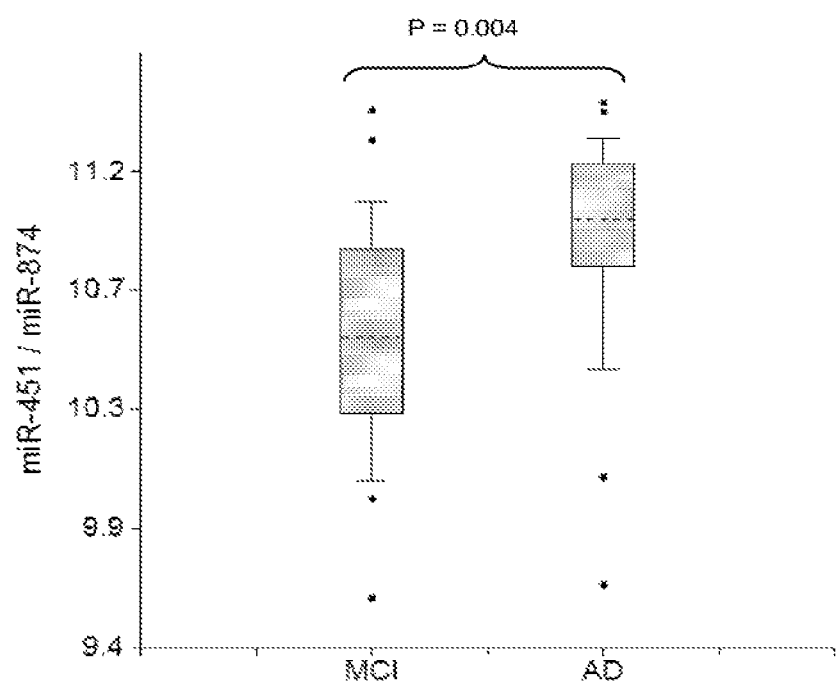
Figure 22A:
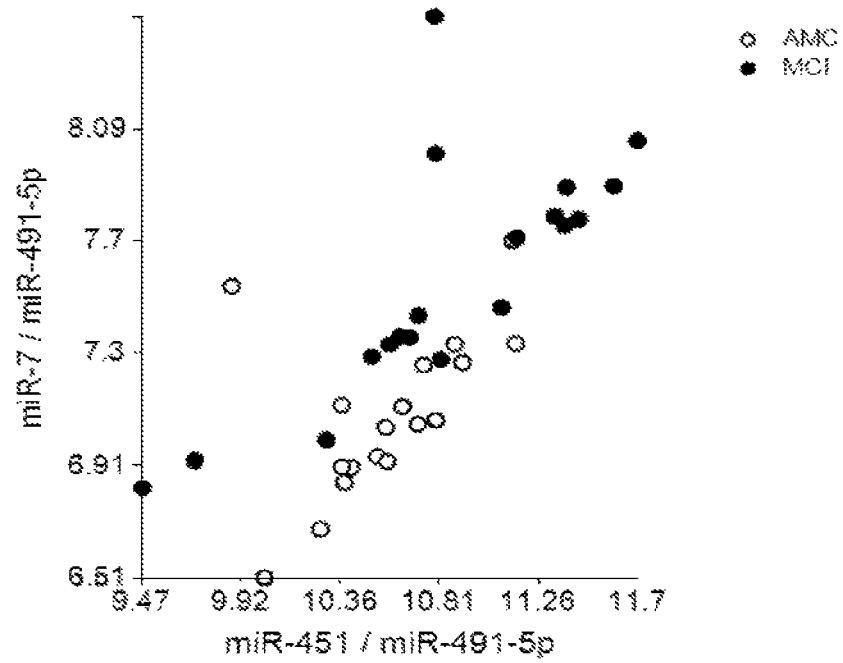
Figure 22B:
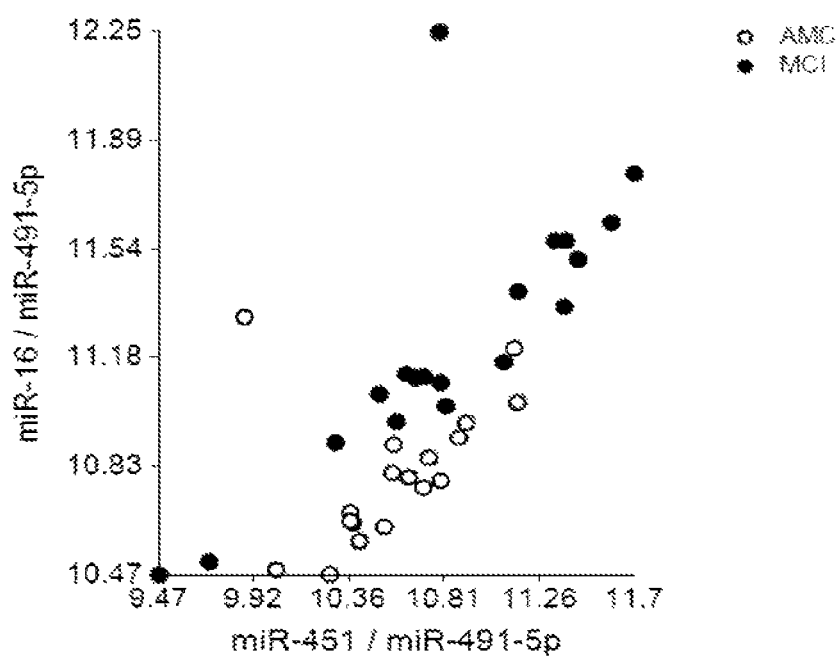
Figure 22C:
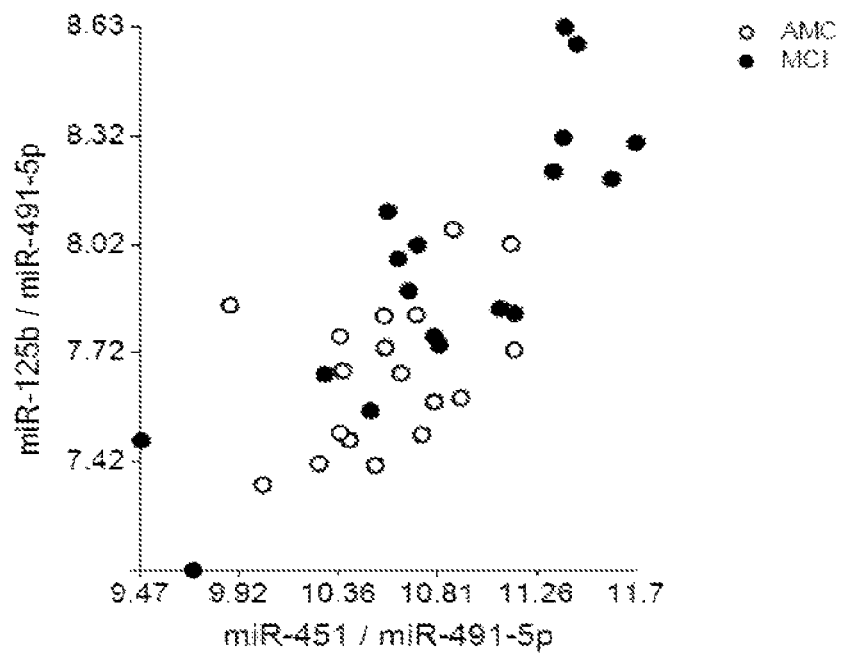
Figure 22D:
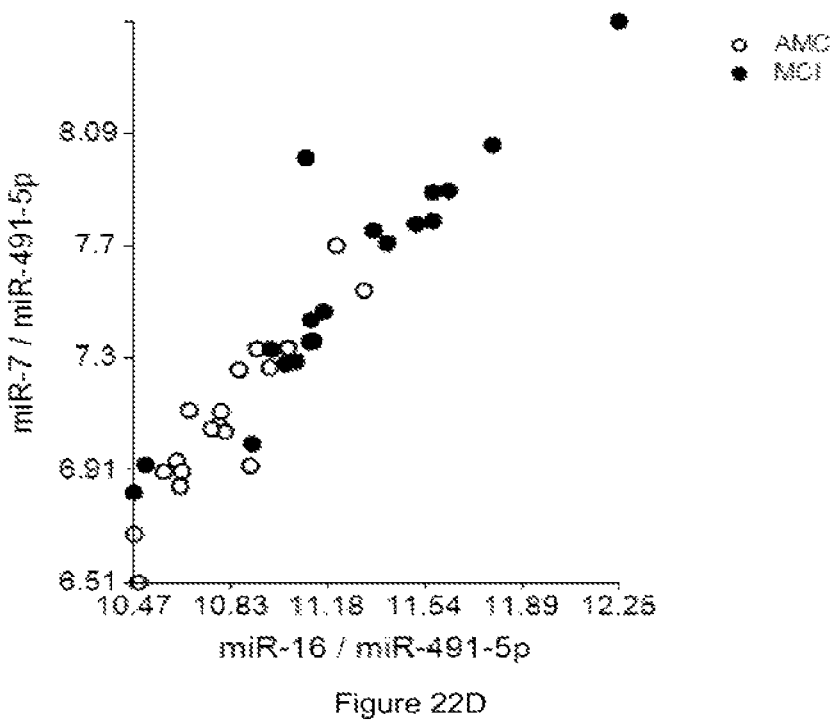
Figure 22E:
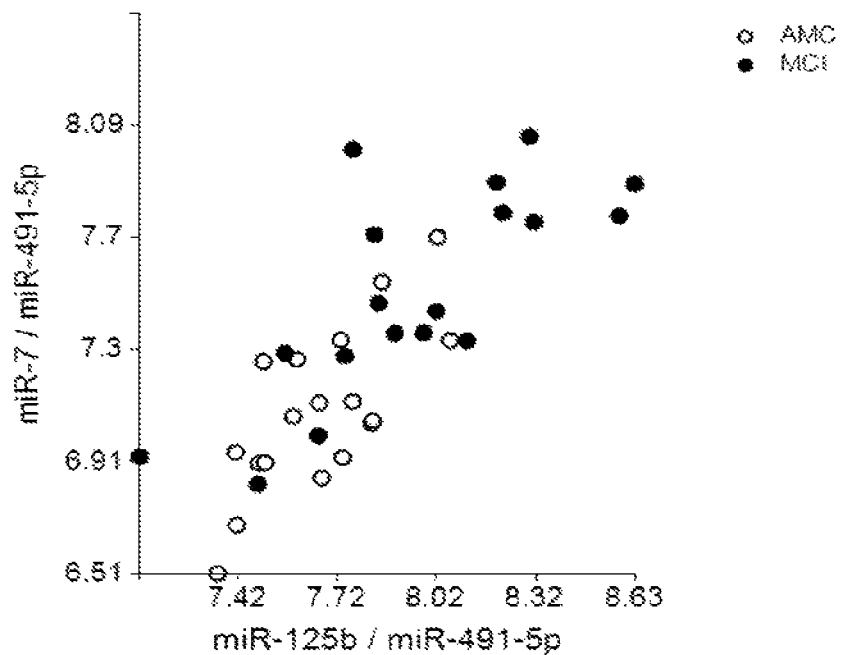
Figure 22F:
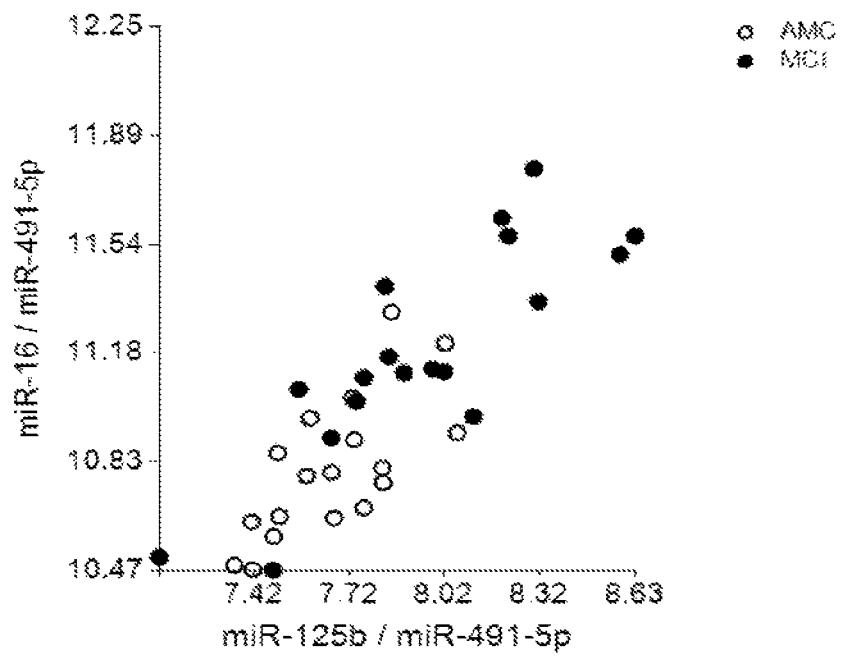
Figures 23A, 23B:
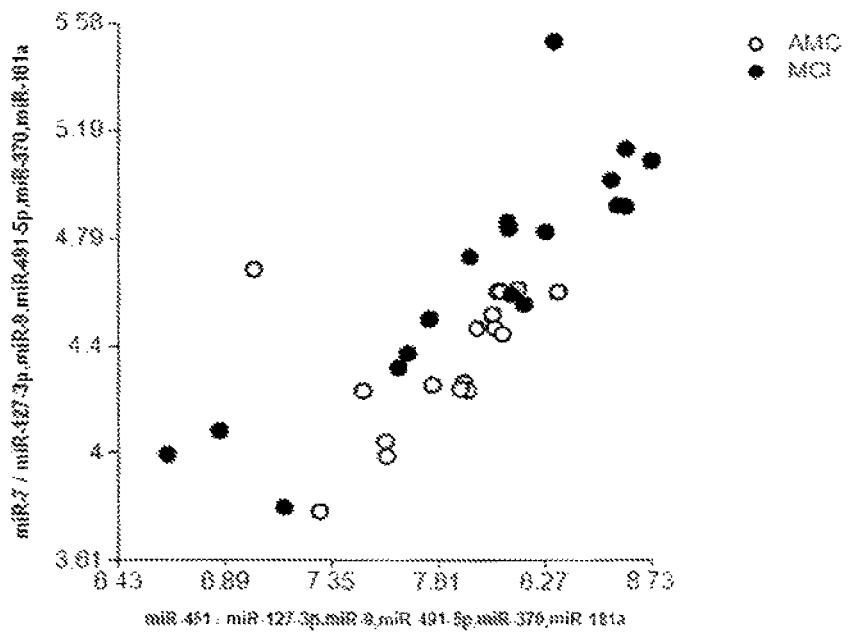
Figure 23C:
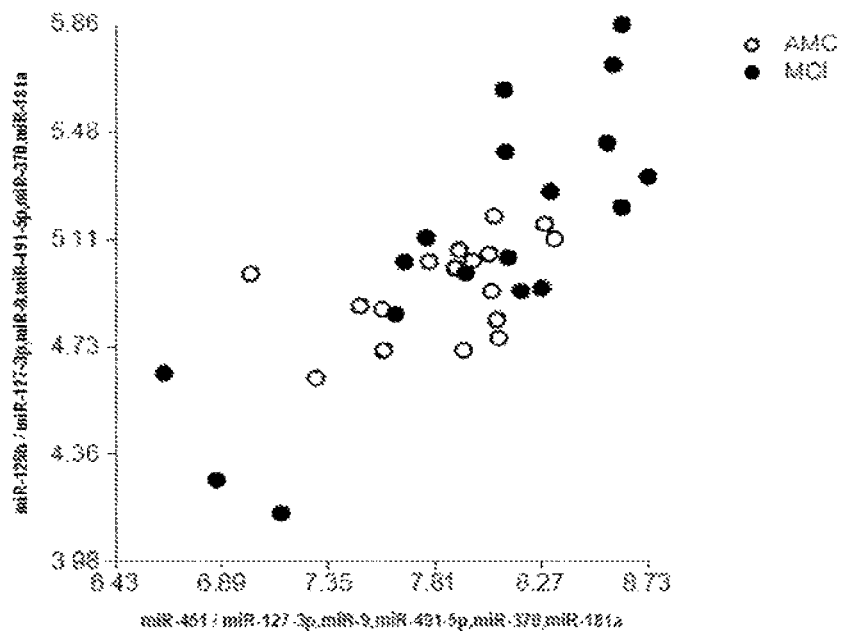
Figure 23D:
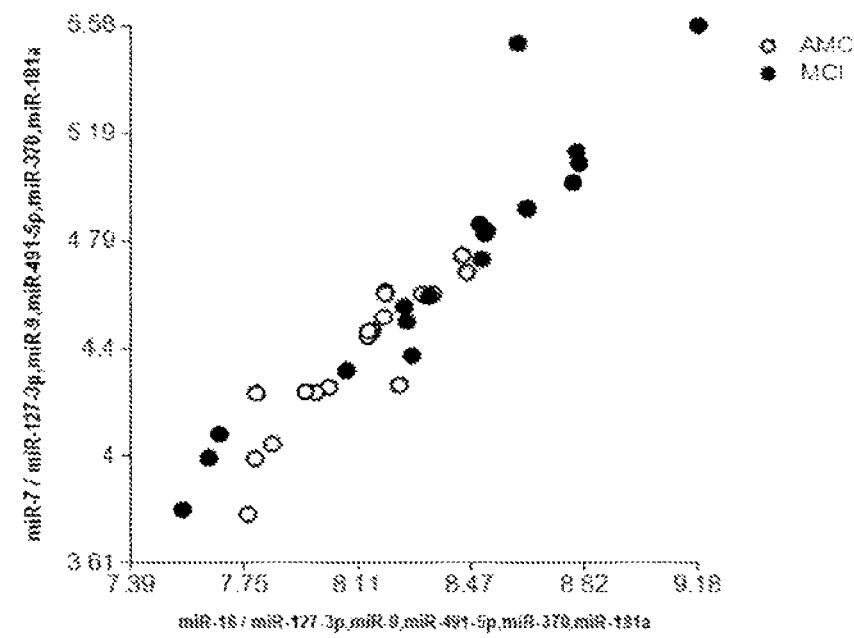
Figure 23E:
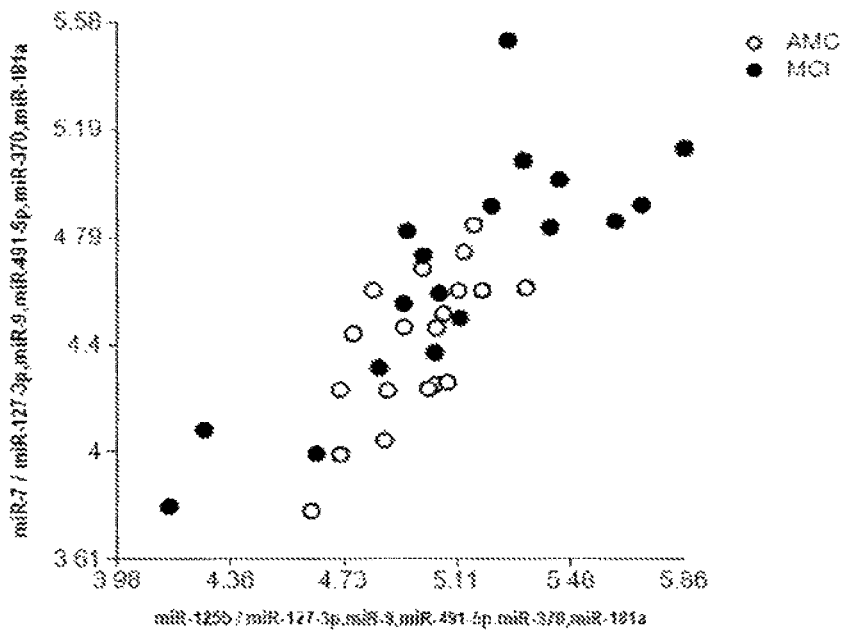
Figure 23F:
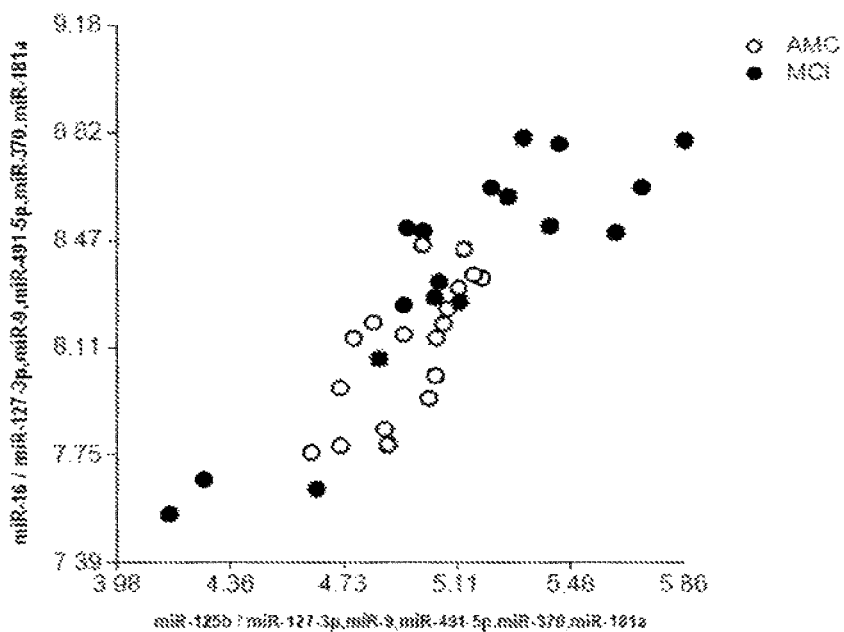

FIGS. 21A-21B are graphs showing the ratio of miR-451 and neurite/synapse miR-132 (A) or miR-874 (B) concentrations in plasma of MCI and AD patients.

FIGS. 22A-22F are graphs showing comparison of two miRNA concentrations in plasma of MCI patients (MCI) and age-matched controls (AMC). All concentrations are normalized per miR-451-5p and presented in relative units (log scale). A: miR-7 and miR-451; B: miR-16 and miR-451; C: miR-125b and miR-451; D: miR-7 and miR-16; E: miR-7 and miR-125b; F: miR-16 and miR-125b.

FIGS. 23A-23F are graphs showing comparison of two miRNA concentrations in plasma of MCI patients (MCI) and age-matched controls (AMC). All concentrations are normalized per the average of 5 normalizers (miR-9, miR-127, miR-181a, miR-370, and miR-491-5p) and presented in relative units (log scale). A: miR-7 and miR-451; B: miR-16 and miR-451; C: miR-125b and miR-451; D: miR-7 and miR-16; E: miR-7 and miR-125b; F: miR-16 and miR-125b.

FIG. 24 compares data presented in FIG. 21, FIG. 14 and FIG. 20. In columns "MCI compared to AD" the grey cells indicate clinically diagnosed MCI patients, whose plasma miR-451/miR-132 and miR-451/miR-874 ratios are in the range characteristic of AD dementia patients. In columns "MCI compared to AMC" the grey cells indicate patients, whose plasma concentrations of miR-7, miR-16, and miR-451 normalized per miR-491-5p differentiate them from aged-matched controls and other MCI patients. Both approaches reveal the same MCI patient, which validates their capability to predict MCI-dementia progression.

DETAILED DESCRIPTION OF THE INVENTION

The present invention is based on the inventors' realization that since neurite (axon and/or dendrite and/or spine) destruction and synapse loss as well as some metabolic events precede neuronal death in the course of development of AD (MCI and a preceding period) and other neurodegenerative diseases, methods based on detection of those phenomena could be used for earlier disease diagnosis than the ones based on detecting cell death. Moreover, since such a test(s) will reflect important events in the pathology development, it could be used for disease and treatment monitoring.

The instant invention is further based on the inventors' discovery that levels of synapse and/or neurite miRNAs increase in bodily fluids of patients with Mild Cognitive Impairment (MCI) compared to respective age-matched controls reflecting excessive destruction of neurites and/or loss of synapses.

Within the meaning of the present invention, the term "synapse and/or neurite miRNA" refers to miRNA which (i) is "brain-enriched", i.e., is present in increased amounts (e.g., at least 5-times higher concentrations) in the brain, as compared to other organs that can be a source of significant amounts of miRNA in a bodily fluid being tested and (ii) is present in a synapse and/or neurite (i.e., axon and/or dendrite and/or spine). Brain enrichment of potential miRNA biomarker is important for screening and primary diagnosis purposes, because many miRNA that are expressed in neurons are also expressed in other tissue and cell types. As a result, changes in such miRNA plasma concentrations may reflect pathology of other organs. On the other hand, when a disease, e.g. MCI, has already been detected miRNA, which are expressed in neurons but are not brain-enriched, can be used for differential diagnosis, prognosis of the disease outcome and monitoring, especially in combination with brain-enriched miRNA biomarker and normalizer. For example, since some synapse and/or neurite miRNAs are much more effectively secreted from abnormal cells during neuronal pathology development, such synapse and/or neurite miRNAs can be also tested as potential biomarkers in the methods of the present invention even if they are not brain-enriched. To be useful in the methods of the present invention, such synapse and/or neurite miRNAs should be detectable in bodily fluids as a result of their release from neurons (e.g., due to secretion, neurite/synapse destruction or neuronal death).

The present invention provides novel highly sensitive and noninvasive or minimally invasive methods for diagnosing Mild Cognitive Impairment (MCI) and various neurodegenerative pathologies it can progress to (e.g., Alzheimer's Disease (AD)) in a subject, said methods comprising determining the level in a bodily fluid sample from the subject (e.g., blood plasma or serum, urine, saliva, or other bodily fluids) of one or more synapse and/or neurite miRNA.

The diagnostic methods of the invention make possible early diagnosis of MCI and preceding stages of AD, other neurodegenerative diseases and other neurodegenerative disorders, e.g., prior to occurrence of major morphological changes and/or massive neuronal cell death associated with such diseases and disorders.

Furthermore, analysis of synapse and/or neurite miRNAs significantly enhances the sensitivity of the miRNA detection as compared to detecting neuronal body miRNAs which are not present or depleted in synapses and neurites, because the amount of synapses and neurites in the brain is $10^3$ times higher than the amount of neurons. This approach also provides detailed and comprehensive information for monitoring disease development and treatment effectiveness, since various specific events in neurons (e.g., changes in miRNA profile, their secretion, neurite degradation, synapse loss, and finally neuronal death) can be detected and quantitated.

Although on a smaller scale, similar processes are characteristic of normal aging and can be detected and monitored using the same approach. Experimental data described in the Examples, below, demonstrate that with appropriate normalization plasma concentration of miR-128, miR-132, miR-874, miR-134, miR-323-3p, and miR-382 is 40%-60% higher in elder control group (76-86 years old) than in "young age" group control (20-50 years old). Respective numbers for MCI patients are significantly higher (200%-500% increase of biomarker miRNA concentration in plasma when compared to the "young age" controls).

Differences in levels of synapse and/or neurite miRNAs in bodily fluids of subjects having MCI, pre-MCI, or other neurodegenerative disorders as compared to age-matched healthy individuals detectable by the methods of the present invention may be due to (i) disease-associated destruction of neurites and/or synapses, (ii) disease-associated changes in expression or metabolism of these miRNAs, (iii) disease-associated changes in transport and intracellular distribution of these miRNAs, (iv) disease-associated changes in secretion of these miRNAs (Rabinowits et al. Clin Lung Cancer, 2009, 10:42-46; e.g., miR-451, miR-1246—see Pigati et al., PLoS ONE, 2010, e13515), (v) disease-associated changes in the blood/brain barrier permeability, as well as other causes.

Since miRNA concentration levels in bodily fluids depend on many factors, data normalization becomes a very important issue. Several approaches can be used for the data normalization: (i) normalization per spiked non-human miRNA (e.g., ath-miR-159a) provides information on miRNA yield during extraction and potential RT-PCR inhibition; (ii) normalization per ubiquitous miRNA (e.g., miR-16), for which a limitation can be disease-related changes in its expression, secretion and so on; (iii) normalization per miRNA, which is expressed in numerous tissues but is under-expressed in brain (e.g. miR-10b, miR-141); (iv) normalization per brain-enriched miRNA, which should compensate such factors as changes in blood supply, blood/brain barrier permeability, and others. The latter approach could be especially productive when: (1) miRNA biomarker is enriched in neurites and/or synapses and miRNA normalizer is present in glial cells mainly, e.g. miR-127 (Wu et al. 2009; Mol. Therapy, 17: 2058-2066); (2) miRNA biomarker is located in neurites or synapses and miRNA normalizer is specific for neuronal body; in this case in early stages of AD miRNA biomarker will be preferably released due to axon, neurite, spine and synapse destruction, and, for example, brain-enriched miR-9 which is located mainly in the perinuclear area of neurons could be used as a normalizer (Truettner et al. 2011. J. Cerebral Blood Flow & Metabolism, epub. April 20), (3) miRNA biomarker is located in hippocampus, which is afflicted first in AD, and miRNA normalizer is located in other brain areas; (4) expression or secretion of miRNA "normalizer" is downregulated due to AD development; thus, measurement of the biomarker/"normalizer" ratio can be useful for early MCI and AD detection. Another important advantage of using various brain-enriched miRNA as normalizers is their absence or very low expression in cells of the peripheral blood which prevents data distortion caused by hemolysis; (v) normalization per the average of several normalizers or, if many, e.g. >15, miRNA are analyzed, normalization per the average of all brain-enriched miRNA tested.

As discussed in detail in the Examples, below, for selection of best biomarker and normalizer miRNAs concentrations of many brain-enriched miRNA, including neurite/synapse ones, in plasma of MCI and AD patients and age-matched control group were analyzed by RT-PCR. Then all miRNA analyzed were tested as potential biomarkers and normalizers and combinations, which provided statistically significant differentiation between MCI patients and age-matched controls, were selected as most promising. The data have demonstrated that the best potential biomarkers are neurite/synapse miRNA and best normalizers are other brain-enriched miRNA. Two families of biomarkers and several normalizers have demonstrated the highest sensitivity (84%-92%) and specificity (84%-90%) in MCI detection, miR-132 family and miR-134 family. High correlation between members of miR-134 family can be easily explained by the fact that all members of this family, namely miR-134, miR-323-3p and miR-382, belong to the same cluster and are expressed in the same cell types. Close relationships between members of miR-132 family, namely miR-128, miR-132 and miR-874, have not been described before. It is also interesting that miR-132 and miR-134 biomarker families give better results with different normalizers. miR-132 family works better than miR-134 family with normalizers miR-491-5p, miR-181a, miR-9, and miR-141. On the other hand, miR-134 family demonstrates better results than miR-132 family with normalizers miR-370 and miR-127.

As disclosed herein, retrospective longitudinal study of MCI development in elderly patients with normal cognitive function at enrollment demonstrated that the increase in plasma miRNA biomarker is detectable in asymptomatic disease stage, preceding MCI clinical manifestation by 1 to 5 years.

Since MCI/AD progression and normal aging share certain common processes, e.g. neurite and synapse destruction and ultimately neuronal death, the present inventors analyzed whether normal aging could also be detected using the same combinations of miRNA biomarkers and normalizers. miRNA in plasma samples from two groups of cognitively normal subjects, Group 1 (21-50 years old) and Group 2 (76-86 years old) were compared. The analysis showed that median concentrations of neurite/synapse miR-132 and miR-134 families were 40-80% higher in the plasma of Group 2 subjects compared to Group 1 ($p<0.05$ to $p<0.001$).

Other promising biomarkers, such as miR-7 and miR-125b, detect smaller subpopulations of MCI patients (about 60% sensitivity) but with high specificity (86%-93%). These miRNA do not detect age-related brain changes, which means that the increase in their plasma concentrations during MCI and AD development is due to less common processes, maybe, those characteristic of AD.

During progression from MCI to the dementia stage of AD the biomarker/normalizer ratio in bodily fluids is changing due to various factors. First, since numerous synapse and neurites are destroyed during early asymptomatic stage of MCI progression, during the later stages of AD there are fewer synapse and neurites and the total amount of excreted synapse/neurite miRNA decreases. Second, due to increased neuronal cell death during the later stages of AD, concentration of neuronal body miRNA in bodily fluids increases. Third, as disease progresses, new brain areas and glial cells become involved in the pathology with disease progression, which lead to further increase in concentration of respective miRNA normalizers in bodily fluids. The phenomena described above can be used to monitor MCI-dementia transition during AD development.

An increase in the level of miR-451, whose secretion from pathologic cells is significantly higher, is statistically significant in the plasma of AD patients when compared to the plasma of MCI patients. The ratios of miR-451 to miRNA of miR-132 and miR-134 families as well as to other brain-enriched miRNA ensure the best differentiation of AD from MCI. However, in about 40-50% of MCI cases these parameters overlap with numbers obtained for AD patients. It is likely that these patients will progress from MCI to the AD dementia. When compared with the age-matched controls after normalization per various miRNA, miR-7, 125b and miR-16 detect the same MCI cases that were characterized as AD by miR-451 analysis, which indicates that both approaches can be used for predicting MCI progression to dementia.

Since different brain areas are involved in various neurodegenerative diseases leading to development of dementia (Geldmacher & Whitehouse, Neurology. 1997, 48:S2-9; Levy & Chelune, J Geriatr Psychiatry Neurol. 2007 20:227-238; Gong & Lippa, Am J Alzheimer's Dis Other Demen, 2010, 25:547-555) and due to different miRNA expression profile in various brain areas (Landgraf et al., Cell. 2007, 129:1401-1414; The miR-Ontology Data Base: http://ferrolab.dmi.unict.it/miro/), analysis of neurite and/or synapse miRNA profile in bodily fluids can be used for differentiation of pre-MCI and MCI that will result in AD dementia or dementia caused by other neurodegenerative diseases.

The methods of the present invention can be used to diagnose pre-MCI and MCI and predict and/or monitor a progression from pre-MCI and MCI to various more severe neurodegenerative diseases such as, e.g., Alzheimer's disease (AD), Parkinson's disease (PD), Lewy Body dementia, Huntington's disease (HD), frontotemporal dementia (FTD), vascular dementia, HIV Associated Neurocognitive Disorders (HAND), mixed dementia, etc.

Non-limiting examples of brain-enriched miRNAs useful in the methods of the present invention include, e.g., 7, 9, 96, 98, 99a, 103, 107, 124a, 125a, 125b, 127, 128a, 132, 134, 137, 138, 149, 153, 154, 181a, 181b, 181c, 182, 183, 204, 212, 213, 218, 219, 221, 222, 299-3p, 299-5p, 323-3p, 324-5p, 328, 329, 330, 331, 335, 337, 338, 342, 346, 369-3p, 369-5p, 370, 379, 381, 382, 383, 409-3p, 411, 425, 432, 433-5p, 485-3p, 485-5p, 487b, 488, 491-5p, 494, 495, 496, 504, 539, 541, 543, 584, 656, 668, 758, 874, 889, 935, 939, 1193, 1197, 9*.

Neurite and/or synapse miRNAs useful in the methods of the present invention include, without limitation, miR-7, miR-25, miR-26a, miR-26b, miR-98, miR-124, miR-125a, miR-125b, miR-128, miR-132, miR-134, miR-137, miR-138, miR-146, miR-154, miR-182, miR-183, miR-200b, miR-200c, miR-218, miR-292-5p, miR-297, miR-322, miR-323-3p, miR-329, miR-325, miR-337, miR-339, miR-345, miR-350, miR-351, miR-369-3, miR-369-5p, miR-381, miR-382, miR-409-3p, miR-425, miR-429, miR-433-5p, miR-446, miR-467, miR-483-3p, miR-485-5p, miR-487b, miR-494, miR-495, miR-496, miR-541, miR-543, miR-656, miR-668, miR-874, miR-889, miR-935, and miR-939 (see Schratt et al., Nature 439:283-289, 2006; Lugli et al., J Neurochem. 106:650-661, 2008; Bicker and Schratt, J Cell Mol Med. 12:1466-1476, 2008; Smalheiser and Lugli, Neuromolecular Med. 11:133-140, 2009; Rajasethupathy, Neuron, 63:714-716, 2009; Kye, RNA, 13:1224-1234, 2007; Yu, et al., Exp Cell Res. 314:2618-2633, 2008; Cougot et al., J Neurosci. 28:13793-13804, 2008; Kawahara, Brain Nerve, 60:1437-1444, 2008; http://ferrolab.dmi.unict.it/miro/). Additional miRNAs useful in the methods of the invention can be identified, for example, based on their enrichment in neurons (and in certain regions of the brain depending on a disease) and intracellular localization in axons and/or dendrites and/or spines and/or synapses. If urine samples are selected for conducting diagnostic methods of the invention, preferred miRNAs for detection would be those miRNAs which are not significantly expressed in cells of the urinary system. Similarly, if blood samples (e.g., serum or plasma) are used for conducting diagnostic methods of the invention, preferred miRNAs for detection would be those miRNAs which are not expressed or are present at very low levels in blood cells.

The methods of the instant invention are based on measurement of levels of certain miRNAs in bodily fluids. The use of bodily fluids that can be collected by non-invasive or minimally invasive techniques (e.g., as opposed to detection in the brain or CSF) allows for a cost effective and minimally invasive or noninvasive diagnostic procedure. Preferred bodily fluids for use in the methods of the invention are blood plasma, serum, urine, and saliva. However, any other bodily fluid can also be used.

Examples of useful methods for measuring miRNA level in bodily fluids include hybridization with selective probes (e.g., using Northern blotting, bead-based flow-cytometry, oligonucleotide microchip [microarray], or solution hybridization assays such as Ambion mirVana miRNA Detection Kit), polymerase chain reaction (PCR)-based detection (e.g., stem-loop reverse transcription-polymerase chain reaction [RT-PCR], quantitative RT-PCR based array method [qPCR-array]), or direct sequencing by one of the next generation sequencing technologies (e.g., Helicos small RNA sequencing, miRNA BeadArray (Illumina), Roche 454 (FLX-Titanium), and ABI SOLiD). For review of additional applicable techniques see, e.g., Chen et al., BMC Genomics, 2009, 10:407; Kong et al., J Cell Physiol. 2009; 218:22-25.

In some embodiments, miRNAs are purified prior to quantification. miRNAs can be isolated and purified from bodily fluids by various methods, including the use of commercial kits (e.g., miRNeasy kit [Qiagen], MirVana RNA isolation kit [Ambion/ABI], miRACLE [Agilent], High Pure miRNA isolation kit [Roche], and miRNA Purification kit [Norgen Biotek Corp.]), Trizol extraction (see Example 1, below), concentration and purification on anion-exchangers, magnetic beads covered by RNA-binding substances, or adsorption of certain miRNA on complementary oligonucleotides.

In some embodiments, miRNA degradation in bodily fluid samples and/or during miRNA purification is reduced or eliminated. Useful methods for reducing or eliminating miRNA degradation include, without limitation, adding RNase inhibitors (e.g., RNasin Plus [Promega], SUPERase-In [ABI] etc.), use of guanidine chloride, guanidine isothiocyanate, N-lauroylsarcosine, sodium dodecylsulphate (SDS), or a combination thereof. Reducing miRNA degradation in bodily fluid samples is particularly important when sample storage and transportation is required prior to miRNA quantification.

To account for possible losses of a given miRNA during purification, potential RT-PCR inhibition, miRNA contaminants derived from dying or damaged blood or urine cells during sample isolation and treatment, variations in kidney filtration, etc., various additional methods of experimental data normalization can be employed. For example, the following normalization methods can be used in the present invention:

a) Concentration of a target miRNA can be normalized to one of the ubiquitous miRNAs (e.g., miR-16), small nucleolar RNAs (snoRNAs), U6 small nuclear RNA (U6 RNA), and others).

b) Synthetic small RNA (e.g., non-human miRNA) oligonucleotides can be synthesized and used as controls for losses during purification and RT-PCR inhibition (by adding them to bodily fluid samples before RNA purification).

c) To account for variations in kidney filtration (when working with urine samples), miRNA concentration in urine can be normalized on creatinine and/or albumin level.

The following approach for selecting miRNA biomarkers for early detection of MCI and AD was developed in the current invention:

1. In addition to known neurite/synapse-enriched miRNAs other brain-enriched miRNAs were included in the preliminary study and analyzed in plasma from AD and MCI patients and compared to age-matched controls.

2. Data for each miRNA were normalized per all other individual miRNAs and miRNA biomarkers and normalizers most promising for MCI detection were selected.

3. These miRNAs were used for a larger study which included plasma samples from younger and age-matched donors, MCI and AD patients.

4. Finally, the retrospective longitudinal study was performed using plasma collected from individuals originally enrolled when they had no symptoms of MCI or AD and then followed for several years. Later some donors developed MCI, some developed AD, and some remained AD and MCI free.

5. In addition to miRNAs enriched in brain, miR-451, which is secreted much more effectively from pathologic cells, was also included in study.

In conjunction with the above diagnostic and screening methods, the present invention provides various kits comprising one or more primer and/or probe sets specific for the detection of target miRNA. Such kits can further include primer and/or probe sets specific for the detection of normalizer miRNA. Non-limiting examples of primer or probe combinations in kits are as follows:

1. Primers or probes specific for at least one miRNA selected from the group consisting of miR-7, miR-125b, and miR-16 (optionally, further comprising primers or probes specific for at least one normalizer miRNA selected from the group consisting of miR-491-5p, miR-9, miR-127, miR-181a, and miR-370).

2. Primers or probes specific for miR-451 (optionally, further comprising primers or probes specific for at least one miRNA selected from the group consisting of miR-7, miR-25, miR-26a, miR-26b, miR-98, miR-124, miR-125a, miR-125b, miR-128, miR-132, miR-134, miR-137, miR-138, miR-146, miR-154, miR-182, miR-183, miR-200b, miR-200c, miR-218, miR-292-5p, miR-297, miR-322, miR-323-3p, miR-329, miR-325, miR-337, miR-339, miR-345, miR-350, miR-351, miR-369-3, miR-369-5p, miR-381, miR-382, miR-409-3p, miR-425, miR-429, miR-433-5p, miR-446, miR-467, miR-483-3p, miR-485-5p, miR-487b, miR-494, miR-495, miR-496, miR-541, miR-543, miR-656, miR-668, miR-874, miR-889, miR-935, and miR-939).

3. Primers or probes specific for at least two miRNAs selected from the group consisting of miR-7, miR-25, miR-26a, miR-26b, miR-98, miR-124, miR-125a, miR-125b, miR-128, miR-132, miR-134, miR-137, miR-138, miR-146, miR-154, miR-182, miR-183, miR-200b, miR-200c, miR-218, miR-292-5p, miR-297, miR-322, miR-323-3p, miR-329, miR-325, miR-337, miR-339, miR-345, miR-350, miR-351, miR-369-3, miR-369-5p, miR-381, miR-382, miR-409-3p, miR-425, miR-429, miR-433-5p, miR-446, miR-467, miR-483-3p, miR-485-5p, miR-487b, miR-494, miR-495, miR-496, miR-541, miR-543, miR-656, miR-668, miR-874, miR-889, miR-935, and miR-939 (optionally, further comprising primers or probes specific for at least one normalizer miRNA selected from the group consisting of miR-10b, miR-141, miR-9, miR-127, miR-181a, miR-370, and miR-491-5p).

4. Primers or probes specific for at least one miRNA selected from the group consisting of miR-128, miR-132, miR-874, miR-134, miR-323-3p, miR-382, miR-7, and miR-125b (optionally, further comprising primers or probes specific for at least one normalizer miRNA selected from the group consisting of miR-10b, miR-141, miR-9, miR-127, miR-181a, miR-370, and miR-491-5p).

5. Primers or probes specific for at least one miRNA selected from the group consisting of miR-128, miR-132, and miR-874 (optionally, further comprising primers or probes specific for at least one normalizer miRNA selected from the group consisting of miR-491-5p, miR-9, miR-181a, and miR-141).

6. Primers or probes specific for at least one miRNA selected from the group consisting of miR-134, miR-323-3p, and miR-382 (optionally, further comprising primers or probes specific for at least one normalizer of miR-370 or miR-127).

7. Primers or probes specific for miR-7 (optionally, further comprising primers or probes specific for at least one normalizer miRNA selected from the group consisting of miR-9, miR-27, miR-181a, miR-370, and miR-491-5p).

8. Primers or probes specific for miR-125b (optionally, further comprising primers or probes specific for at least one normalizer miRNA selected from the group consisting of miR-9, miR-181a, miR-370, and miR-491-5p).

Such kits can be useful for direct miRNA detection in bodily fluid samples isolated from patients or can be used on purified RNA samples.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs). Alternatively (or in addition), a kit can include reagents for performing a hybridization assay. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include miRNA isolation or purification means as well as positive and negative controls. A kit can also include a notice associated therewith in a form prescribed by a governmental agency regulating the manufacture, use or sale of diagnostic kits. Detailed instructions for use, storage and trouble shooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

Definitions

The term "Alzheimer's Disease" or "AD" as used herein refers to post-MCI AD phases characterized by dementia.

The term "pre-Mild Cognitive Impairment" or "pre-MCI" refers to asymptomatic, preclinical phase of AD and other neurodegenerative diseases leading to dementia (Jack et al., Alzheimer's and Dementia. 2011, Epub April 19).

The term "neuronal cell body" refers to the portion of a nerve cell that contains the nucleus surrounded by the cytoplasm and the plasma membrane but does not incorporate the dendrites or axons.

The term "neurite" as used herein refers to any projection from the cell body of a neuron. This projection can be an axon, a dendrite, or a spine.

The term "axon" refers to a long, slender projection of a neuron that conducts electrical impulses away from the neuron's cell body or soma. Axons are distinguished from dendrites by several features, including shape (dendrites often taper while axons usually maintain a constant radius), length (dendrites are restricted to a small region around the cell body while axons can be much longer), and function (dendrites usually receive signals while axons usually transmit them). Axons and dendrites make contact with other cells (usually other neurons but sometimes muscle or gland cells) at junctions called synapses.

The term "dendrite" refers to a branched projection of a neuron that acts to conduct the electrochemical stimulation received from other neural cells to the cell body of the neuron from which the dendrites project.

The terms "spine" or "dendritic spine" refer to a small membranous protrusion from a neuron's dendrite that typically receives input from a single synapse of an axon. Dendritic spines serve as a storage site for synaptic strength and help transmit electrical signals to the neuronal cell body. Most spines have a bulbous head (the spine head), and a thin neck that connects the head of the spine to the shaft of the dendrite. The dendrites of a single neuron can contain hundreds to thousands of spines. In addition to spines providing an anatomical substrate for memory storage and synaptic transmission, they may also serve to increase the number of possible contacts between neurons.

The term "synapse" refers to specialized junctions, through which neurons signal to each other and to non-neuronal cells such as those in muscles or glands. A typical neuron gives rise to several thousand synapses. Most synapses connect axons to dendrites, but there are also other types of connections, including axon-to-cell-body, axon-to-axon, and dendrite-to-dendrite. In the brain, each neuron forms synapses with many others, and, likewise, each receives synaptic inputs from many others. As a result, the output of a neuron may depend on the input of many others, each of which may have a different degree of influence, depending on the strength of its synapse with that neuron. There are two major types of synapses, chemical synapses and electrical synapses. In electrical synapses, cells approach within about 3.5 nm of each other, rather than the 20 to 40 nm distance that separates cells at chemical synapses. In chemical synapses, the postsynaptic potential is caused by the opening of ion channels by chemical transmitters, while in electrical synapses it is caused by direct electrical coupling between both neurons. Electrical synapses are therefore faster than chemical synapses.

Within the meaning of the present invention, the term "synapse and/or neurite miRNA" refers to miRNA which (i) is "brain-enriched", i.e., is present in increased amounts (e.g., at least 5-times higher concentrations) in the brain, as compared to other organs that can be a source of significant amounts of miRNA in a bodily fluid being tested and (ii) is present in a synapse and/or neurite (i.e., axon and/or dendrite and/or spine).

Since some synapse and/or neurite miRNAs are much more effectively secreted from abnormal cells during neuronal pathology development, such synapse and/or neurite miRNAs can be also tested as potential biomarkers in the methods of the present invention even if they are not brain-enriched. To be useful in the methods of the present invention, such synapse and/or neurite miRNAs should be detectable in bodily fluids as a result of their release from neurons (e.g., due to secretion, neurite/synapse destruction or neuronal death).

The term "normalizer miRNA" as used herein refers to miRNA which is used for normalization of neurite/synapse miRNA concentration to account for various factors that affect appearance and stability of neurite/synapse miRNA in plasma.

The term "neuronal body miRNA" as used herein refers to miRNA which (i) is "brain-enriched", i.e., is present in increased amounts (e.g., at least 5-times higher concentrations) in the brain, as compared to other organs that can be a source of significant amounts of miRNA in a bodily fluid being tested and (ii) is absent from or present insignificantly lower concentrations in neurites or synapses than in neuronal cell bodies.

The terms "neuronal pathology" and "pathological changes in neurons" are used herein to refer to metabolic and/or structural changes in neurons associated with neurite and/or synapse dysfunction and/or neurite destruction and/or synapse loss.

The term "associated with" is used to encompass any correlation, co-occurrence and any cause-and-effect relationship.

The term "development of a neuronal pathology" is used herein to refer to any negative change in the extent/severity of a metabolic and/or structural change in individual neurons and/or any increase in the number of neurons affected. The phrase "improvement of a neuronal pathology" and similar terms refer to any positive change in the extent/severity of a metabolic and/or structural change in individual neurons and/or any decrease in the number of neurons affected.

As used herein, the term "small RNA" refers generally to a heterogeneous group of non-coding RNAs with a variety of regulatory functions including chromatin architecture/epigenetic memory, transcription, RNA splicing, RNA editing, mRNA translation, and RNA turnover. The diagnostic methods of the present invention rely on detecting neurite and/or synapse small RNAs, which can be detected in bodily fluids, such as, for example, microRNAs (miRNAs), Brain Cytoplasmic RNAs BC1/BC200, etc. There are other classes of less characterized small RNAs which can be also useful in the methods of the present invention (reviewed in Kim, Mol. Cells, 2005, 19: 1-15).

The terms "microRNA" or "miRNA" as used herein refer to a class of small approximately 22 nt long non-coding RNA molecules. They play important roles in the regulation of target genes by binding to complementary regions of messenger transcripts (mRNA) to repress their translation or regulate degradation (Griffiths-Jones Nucleic Acids Research, 2006, 34, Database issue: D140-D144). Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). Examples of neurite and/or synapse miRNAs useful in the methods of the present invention include, without limitation, miR-7, miR-25, miR-26a, miR-26b, miR-98, miR-124, miR-125a, miR-125b, miR-128, miR-132, miR-134, miR-137, miR-138, miR-146, miR-154, miR-182, miR-183, miR-200b, miR-200c, miR-218, miR-292-5p, miR-297, miR-322, miR-323-3p, miR-329, miR-325, miR-337, miR-339, miR-345, miR-350, miR-351, miR-369-3, miR-369-5p, miR-381, miR-382, miR-409-3p, miR-425, miR-429, miR-433-5p, miR-446, miR-467, miR-483-3p, miR-485-5p, miR-487b, miR-494, miR-495, miR-496, miR-541, miR-543, miR-656, miR-668, miR-874, miR-889, miR-935, and miR-939. Information on most currently known miRNAs can be found in the miRNA database miRBase (available at the world wide web at mirbase.org). See also Burside et al., BMC Genomics 9:185 (2008); Williams et al., BMC Genomics 8:172 (2007); Landgraf et al., Cell 129:1401 (2007).

The term "miRNA array" refers to a multiplex technology used in molecular biology and in medicine. It consists of an arrayed series of multiple (e.g., thousands) microscopic spots of oligonucleotides, each containing a specific sequence (probe) complementary to a particular target miRNA. After probe-target hybridization under high-stringency conditions the resulting hybrids are usually detected and quantified by quantifying fluorophore-, silver-, or chemiluminescence-labeled targets to determine relative abundance of miRNA. In the methods of the present invention, both custom-made and commercially available miRNA arrays can be used. Examples of useful commercially available miRNA arrays (based on various methods of target labeling, hybrid detection and analysis) include arrays produced by Agilent, Illumina, Invitrogen, Febit, and LC Sciences.

The term "next generation sequencing technologies" broadly refers to sequencing methods which generate multiple sequencing reactions in parallel. This allows vastly increased throughput and yield of data. Non-limiting examples of commonly used next generation sequencing platforms include Helicos small RNA sequencing, miRNA BeadArray (Illumina), Roche 454 (FLX-Titanium), and ABI SOLiD.

An "individual" or "subject" or "animal", as used herein, refers to humans, veterinary animals (e.g., cats, dogs, cows, horses, sheep, pigs, etc.) and experimental animal models of neurodegenerative diseases or other neuronal pathologies. In a preferred embodiment, the subject is a human.

The term "urinary tract" refers to the organs and ducts, which participate in the secretion and elimination of urine from the body.

The term "purified" as used herein refers to material that has been isolated under conditions that reduce or eliminate the presence of unrelated materials, i.e., contaminants, including native materials from which the material is obtained. For example, RNA purification includes elimination of proteins, lipids, salts and other unrelated compounds present in bodily fluids. Besides, for some methods of analysis a purified miRNA is preferably substantially free of other RNA oligonucleotides contained in bodily fluid samples (e.g., rRNA and mRNA fragments, ubiquitous miR-NAs, which are expressed at high levels in almost all tissues [e.g., miR-16], etc.). As used herein, the term "substantially free" is used operationally, in the context of analytical testing of the material. Preferably, purified material substantially free of contaminants is at least 50% pure; more preferably, at least 90% pure, and still more preferably at least 99% pure. Purity can be evaluated by chromatography, gel electrophoresis, composition analysis, biological assay, and other methods known in the art.

As used herein, the term "similarly processed" refers to samples (e.g., bodily fluid samples or purified RNAs) which have been obtained using the same protocol.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, NY: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Comparison of Different Methods Used for miRNA Purification from Serum or Plasma There are many commercial kits for miRNA isolation, including the miRNeasy kit (Qiagen), the MirVana RNA isolation kit (Ambion/ABI), miRACLE (Agilent), High Pure miRNA isolation kit (Roche), and miRNA Purification kit (Norgen Biotek Corp.). Besides, the in-house techniques based on the use of Trizol (Invitrogen) can be used. In this technique (Invitrogen's protocol), after Trizol LS deproteinization, RNA is precipitated with isopropyl alcohol or additionally purified on silica columns. In some experiments, purified RNA is treated with RNAse-free DNAse (Qiagen, ABI, Invitrogen or other).

miRNA preparations obtained by different methods were compared using RT-PCR. Using Trizol LS (Invitrogen's protocol) and the MirVana RNA isolation kit (Ambion/ABI protocol) miRNA was purified from plasma and serum samples obtained from the same 5 healthy donors. $10^7$ copies of Arabidopsis thaliana miR-159a (ath-miR-159a) were spiked per 1 ml plasma or serum after addition of guanidine-containing solution for evaluation of miRNA yield. Two techniques, one based on MirVana Paris kit (Ambion/ABI), and another based on Trizol (Invitrogen) deproteinization, and subsequent purification on silica columns, were compared. After RNA purification concentrations of spiked miRNA and human endogenous miR-9, miR-16, and miR-134 in final preps were measured by RT-PCR. Both MirVana Paris kit and the Trizol/silica filtration-based technique were effective in miRNA isolation and were used in future experiments. Although all analyzed miRNA were detectable in serum and plasma and both sample types are suitable for miRNA testing, the final PCR Ct values were about 2 cycles lower for plasma, and the latter was used in subsequent experiments. Based on the quantitative measurement of spiked ath-miR-159a, average yield of miRNA from plasma was about 70%.

A similar analysis was performed using plasma samples and the miRNeasy kit (Qiagen). A synthetic non-human miRNA was spiked after guanidine addition for calculating miRNA yield.

Example 2: Selection of miRNA for Testing

Tested miRNAs were initially selected based on literature data on their enrichment in brain compartments and presence in neurites (i.e., axons and/or dendrites and/or spines) and/or synapses (Hua et al., BMC Genomics 2009, 10:214; Liang et al., BMC Genomics. 2007, 8:166; Landgraf et al., Cell. 2007, 129:1401-1414; Lee et al., RNA. 2008, 14:35-42; Schratt et al., Nature. 439:283-289, 2006; Lugli et al., J Neurochem. 106:650-661, 2008; Bicker and Schratt, J Cell Mol Med., 12:1466-1476, 2008; Smalheiser and Lugli, Neuromolecular Med. 11:133-140, 2009; Rajasethupathy, Neuron. 63:714-716, 2009; Kye, RNA 13:1224-1234, 2007; Yu et al., Exp Cell Res. 314:2618-2633, 2008; Cougot, et al., J Neurosci. 28:13793-13804, 2008; Kawahara, Brain Nerve. 60:1437-1444, 2008; Schratt G. Rev Neurosci. 2009; 10:842-849; Pichardo-Casas et al. Brain Research. 1436:20-33, 2012) as well as on their suggested involvement in neurite- and synapse-associated processes (The miR-Ontology Data Base: http://ferrolab.dmi.unict.it/miro/). For normalization, in addition to spiked miRNA, ubiquitous miRNA, such as miR-16, as well as miRNA expressed in numerous tissues but not in the brain, such as miR-10b and miR-141, were used.

Example 3: Experimental Pre-Selection of miRNA Biomarkers and Normalizers

Plasma samples were obtained from patients diagnosed with MCI with amnestic symptoms (aMCI) (Dlugaj et al., Dement Geriatr Cogn Disord., 2010, 30:362-373; Brooks, Loewenstein, Alzheimer's Res Therapy, 2010, 2:28-36). Profiles of brain-enriched miRNAs from plasma of these patients were analyzed using RT-PCR with primers and probes for each individual miRNA (ABI). The amount of RNA equivalent to 30 μL plasma were taken in each RT reaction, and ⅕ of RT product was taken into final PCR. Thus, the amount of miRNA equivalent to 2 μL plasma was detected. The results obtained for each miRNA were normalized per each potential normalizer miRNA, converted into Relative Concentration (RC) of miRNA according to the ABI protocol ($2^{-\Delta Ct}$), and compared with miRNA profiles from age-matched controls (AMC). Practically, all miRNA analyzed were tested as potential biomarkers and normalizers and combinations, which provided statistically significant differentiation between MCI patients and age-matched controls were selected for further studies. Two conclusions are obvious from data presented below. First, the best potential biomarkers are neurite/synapse miRNA and, second, best normalizers are other brain-enriched miRNA.

When normalization per spiked non-human miRNA (ath-miR-159a) was performed, which gives relative miRNA concentration per 1 ml plasma, some plasma samples from MCI patients contained more neurite and/or synapse miR-NAs (FIG. 1, miR-7 (A) and miR-874 (B)).

At the same time concentrations of other brain-enriched miRNAs were not changed in the plasma of MCI patients (FIG. 1, miR-9 (C), miR-181a (D) and miR-491-5p (E)).

Figure 1A:
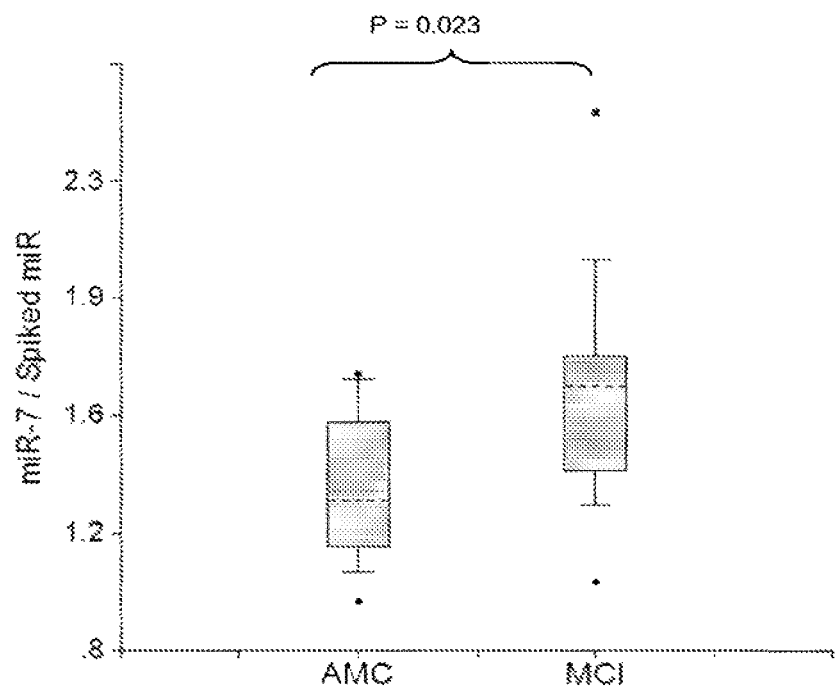
FIGS. 1A-1E are graphs showing comparison of concentrations of miR-7 (A), miR-874 (B), miR-9 (C), miR-181a (D) and miR-491-5p (E) in plasma of MCI patients (MCI) and age-matched controls (AMC). All concentrations were normalized per spiked ath-miR-159a. Here and in other box and whisker plots, the box indicates the distribution of 50% of the results and the bar above and below the box indicates 80% of the results. The points indicate assay values located outside of 80% data. Median value of the assays is indicated by the line inside the box. Normalized miRNA concentrations are presented on ordinate axis in relative units (log scale).
Figure 1B:
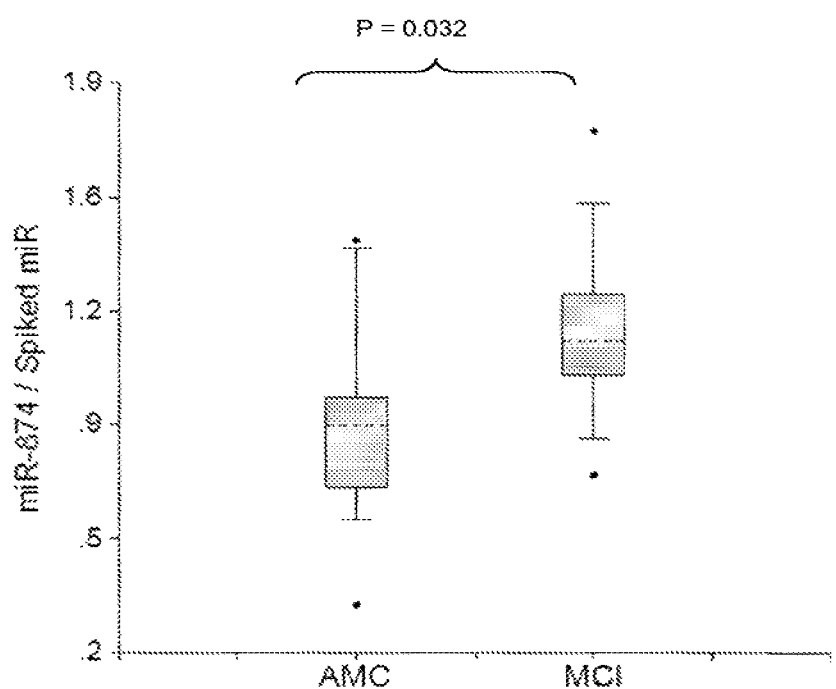
Figure 1C:
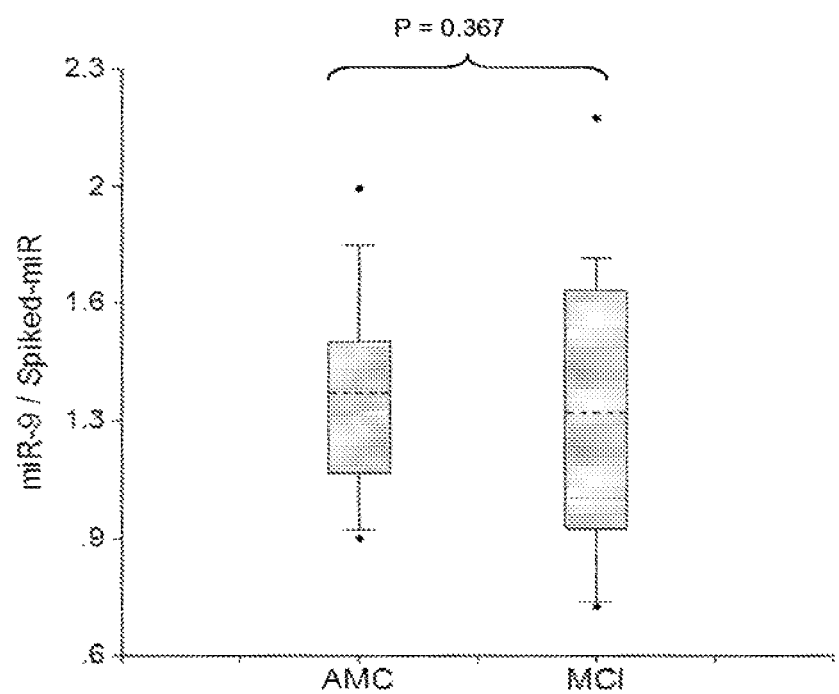
Figure 1D:
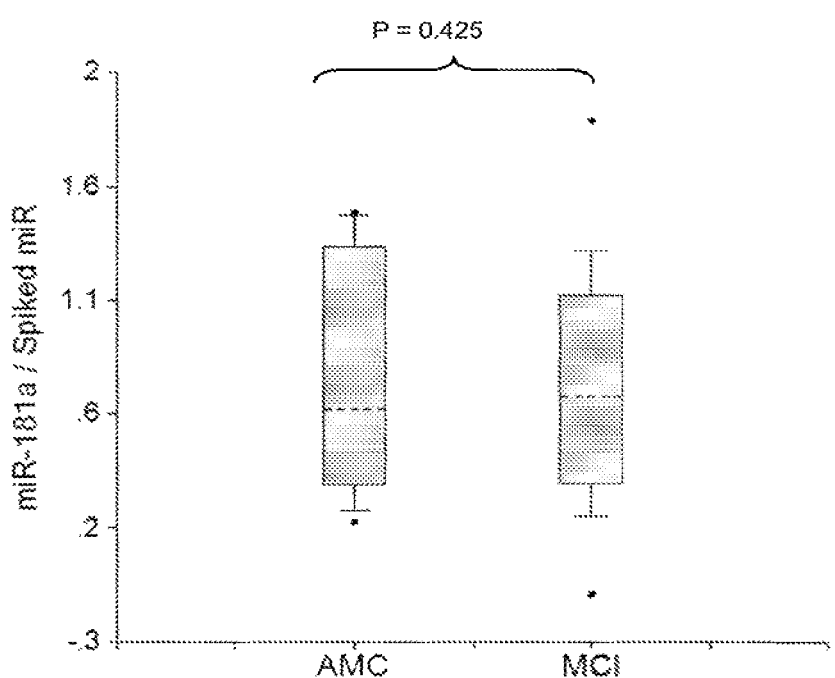
Figure 1E:
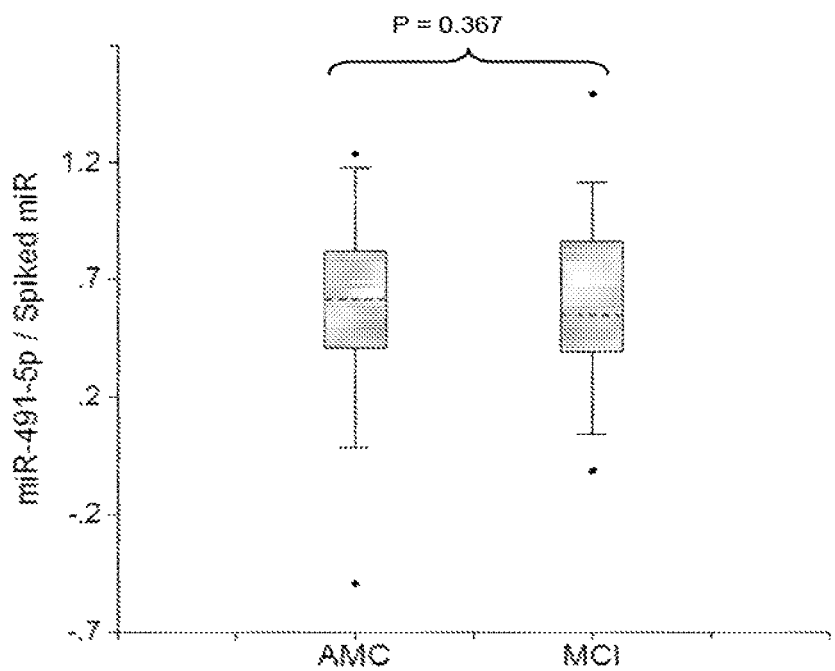
Figure 2A:
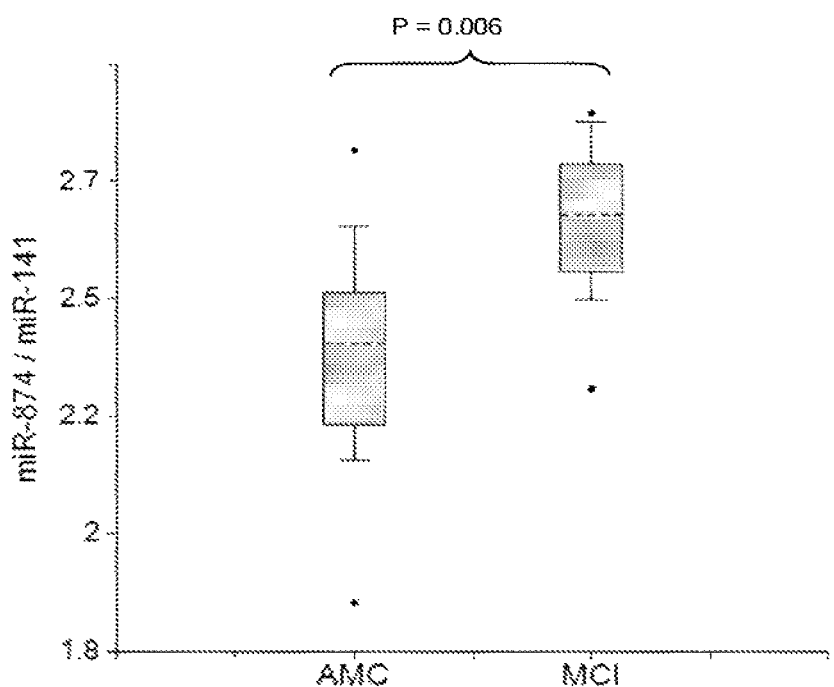
FIGS. 2A-2C are graphs showing comparison of concentrations of miR-874 (A), miR-134 (B) and miR-539 (C) in plasma of MCI patients (MCI) and age-matched controls (AMC). All concentrations were normalized per miR-141.
Figure 2B:
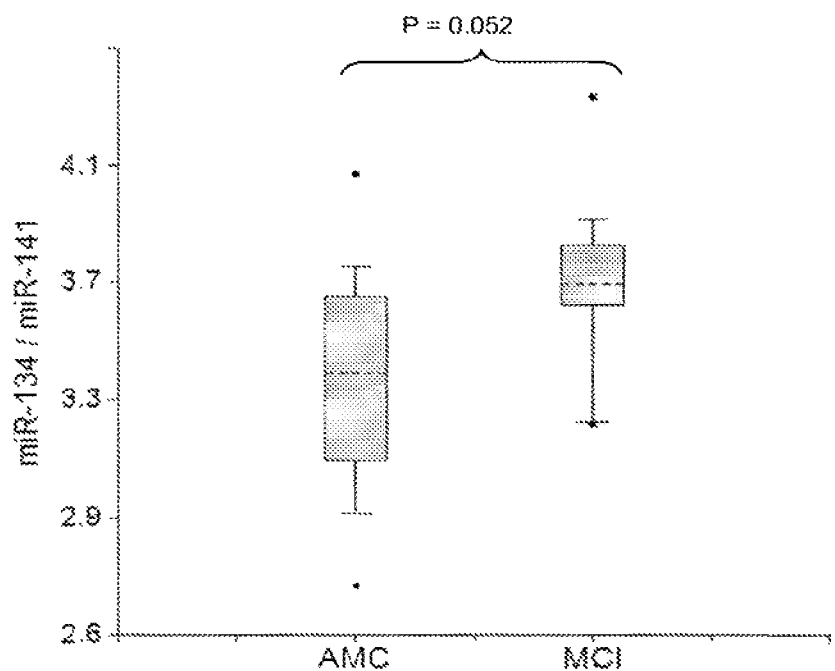
Figure 2C:
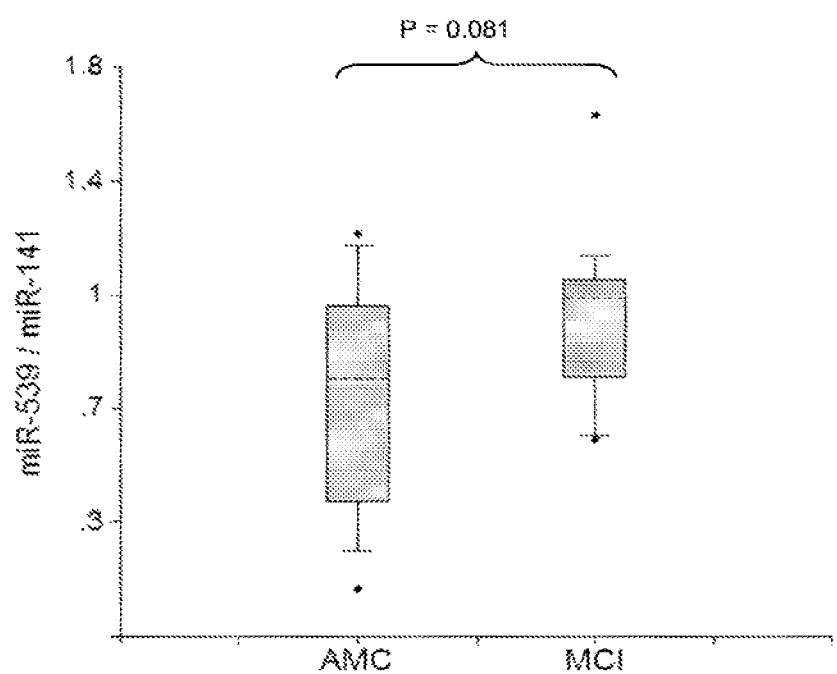
Figure 3A:
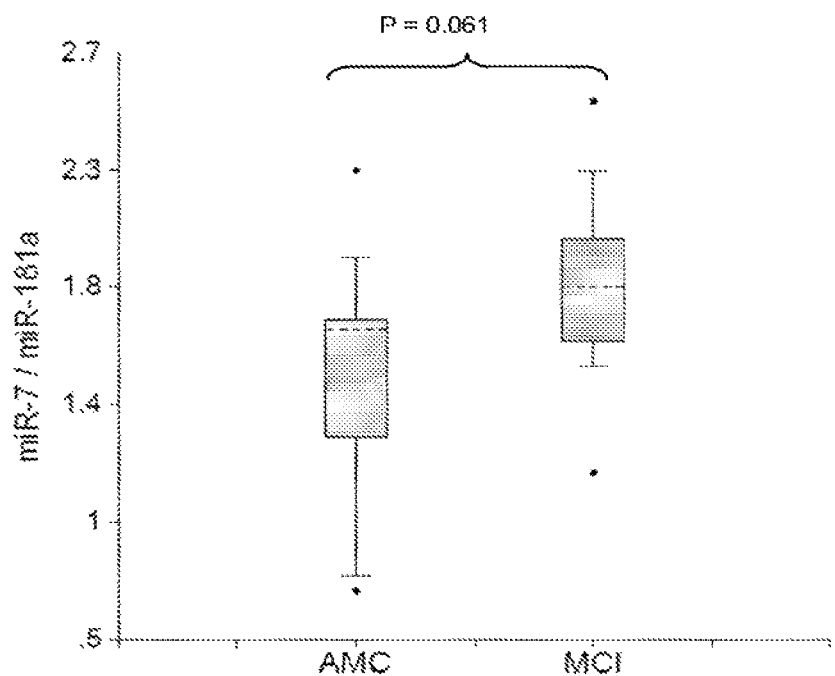
Figure 3B:
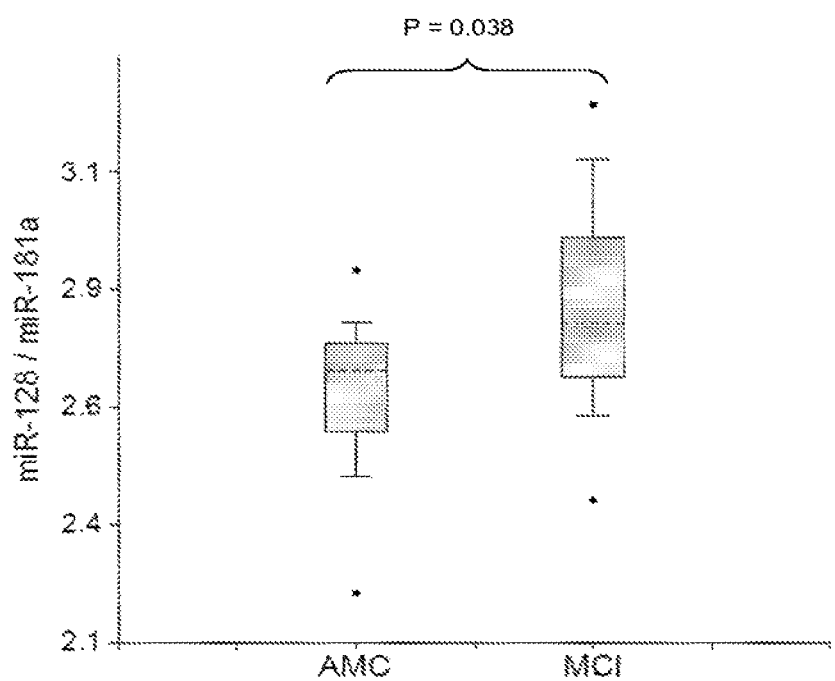
Figure 3C:
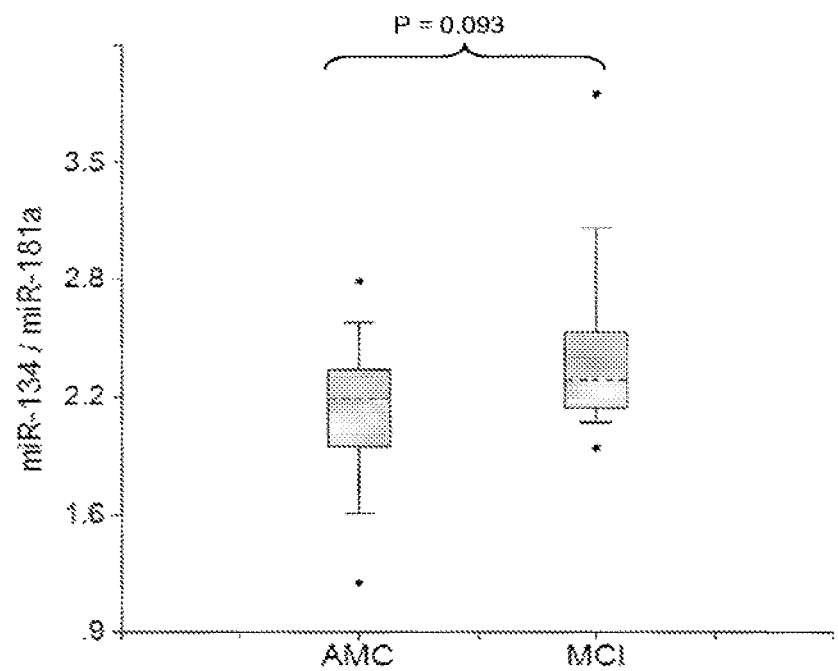
Figure 4:
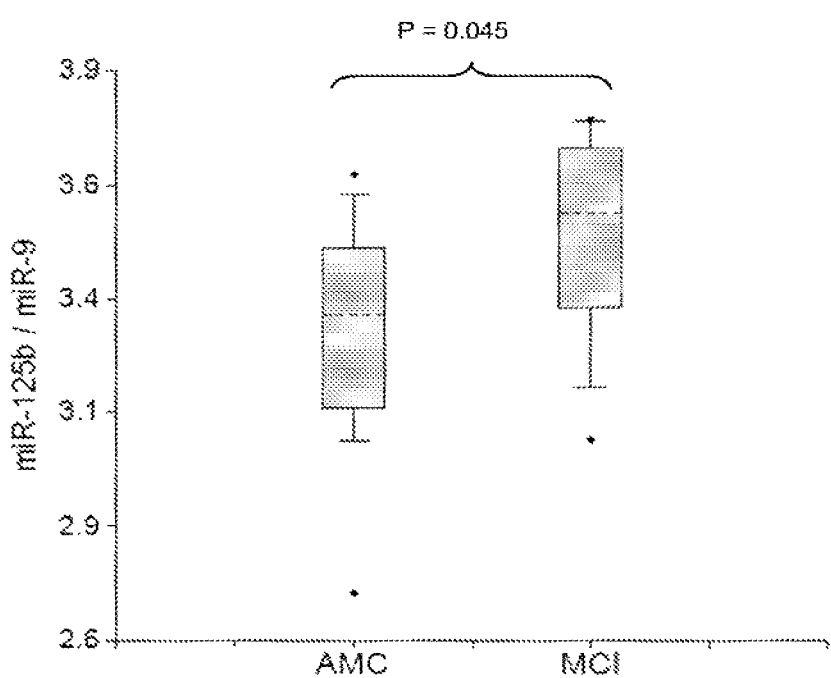
FIG. 4 is a graph showing comparison of miR-125b concentrations in plasma of MCI patients (MCI) and age-matched controls (AMC). Concentrations of miR-125b were normalized per miR-9.
Figure 5A:
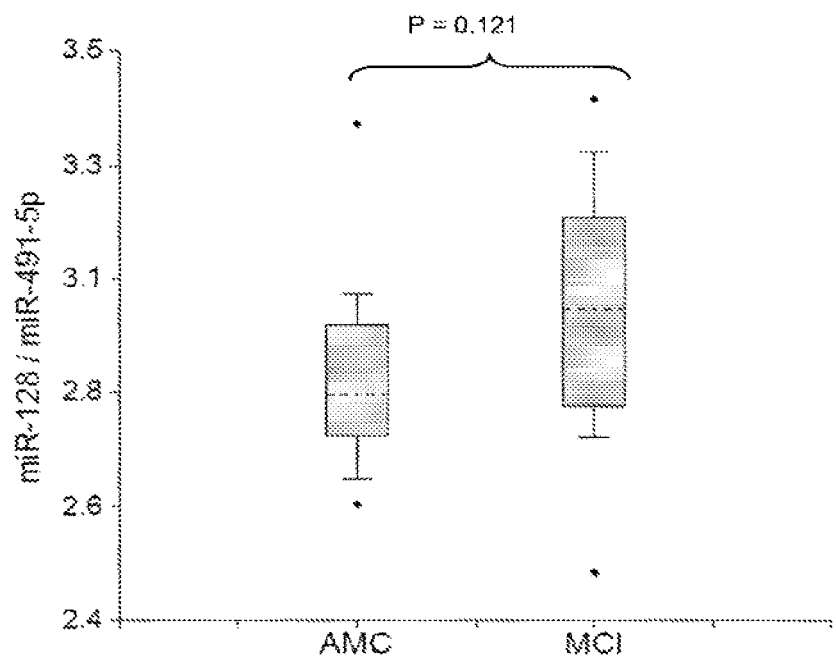
FIGS. 5A-5C are graphs showing comparison of miRNA concentrations in plasma of MCI patients (MCI) and age-matched controls (AMC). Concentrations of miR-128 (A), miR-134 (B) and miR-874 (C) were normalized per miR-491-5p.
Figure 5B:
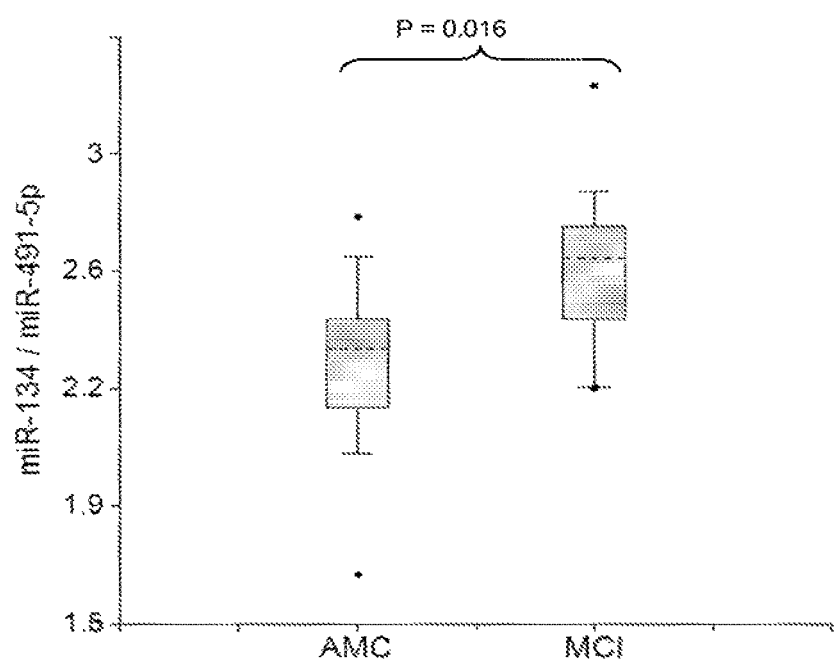
Figure 5C:
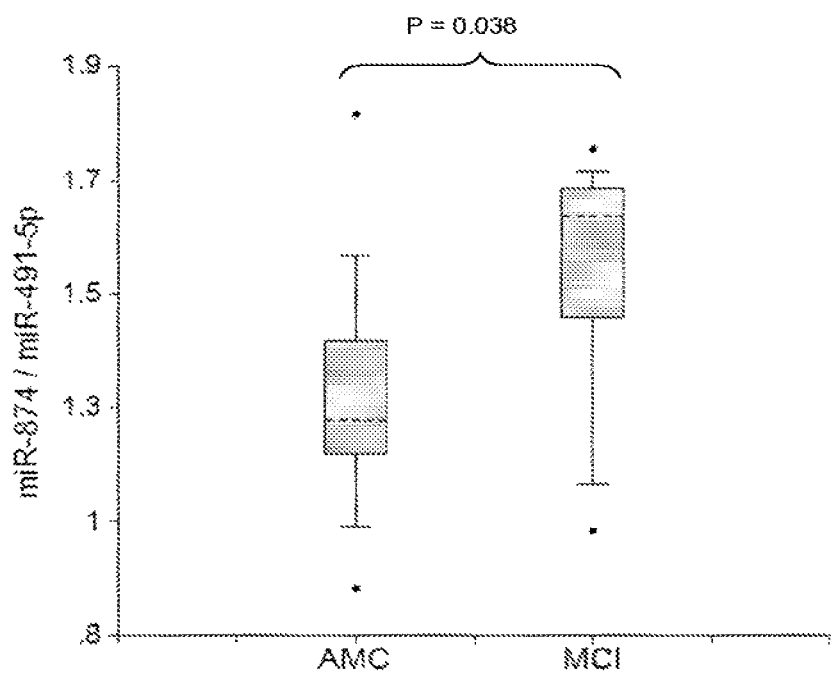
Figure 6:
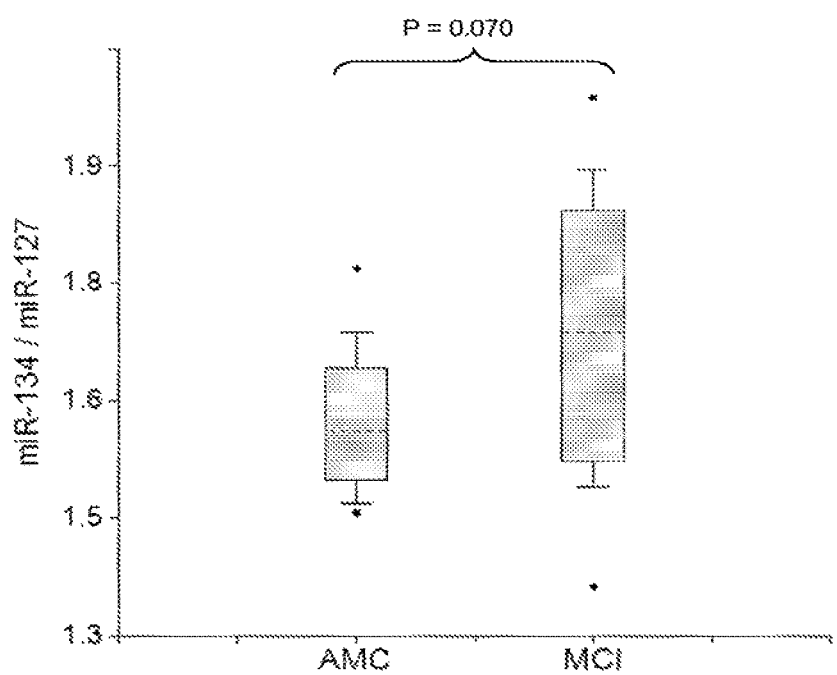
FIG. 6 is a graph showing comparison of miRNA concentrations in plasma of MCI (MCI) and age-matched controls (AMC). Concentration of miR-134 was normalized per miR-127
Figure 7A:
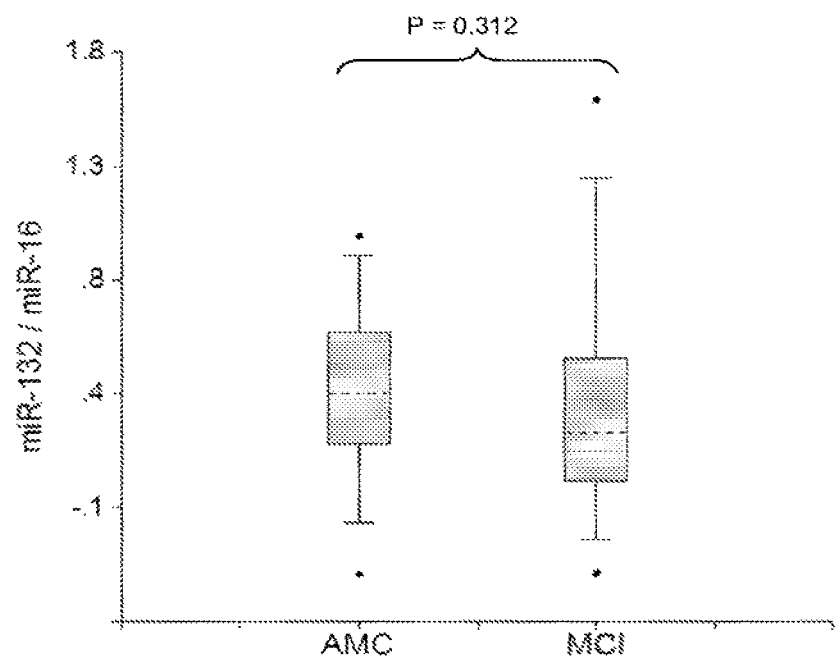
FIGS. 7A-7B are graphs showing comparison of miRNA concentrations in plasma of MCI patients (MCI) and age-matched controls (AMC). Concentrations of miR-132 (A) and miR-323-3p (B) were normalized per miR-16.
Figure 7B:
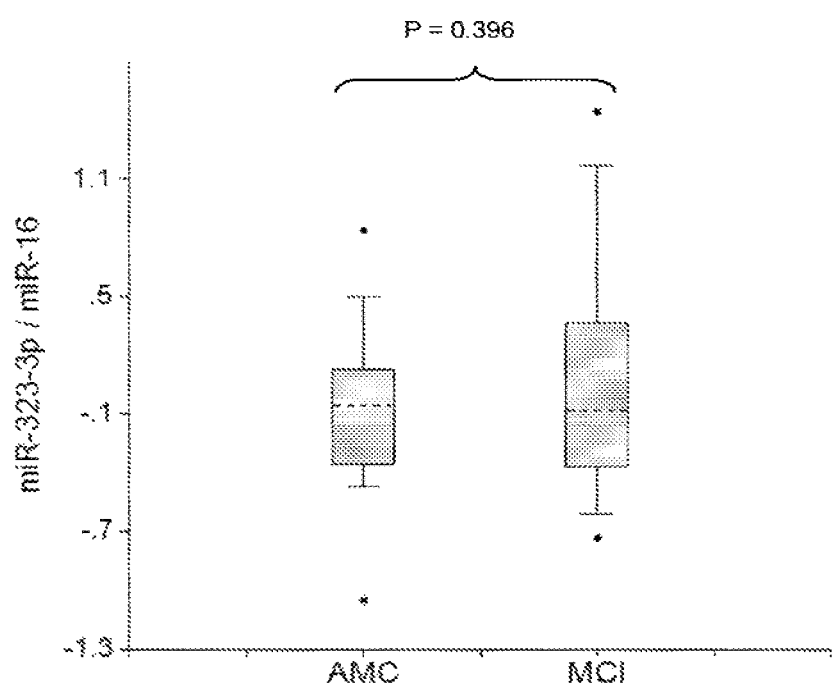
Figure 8A:
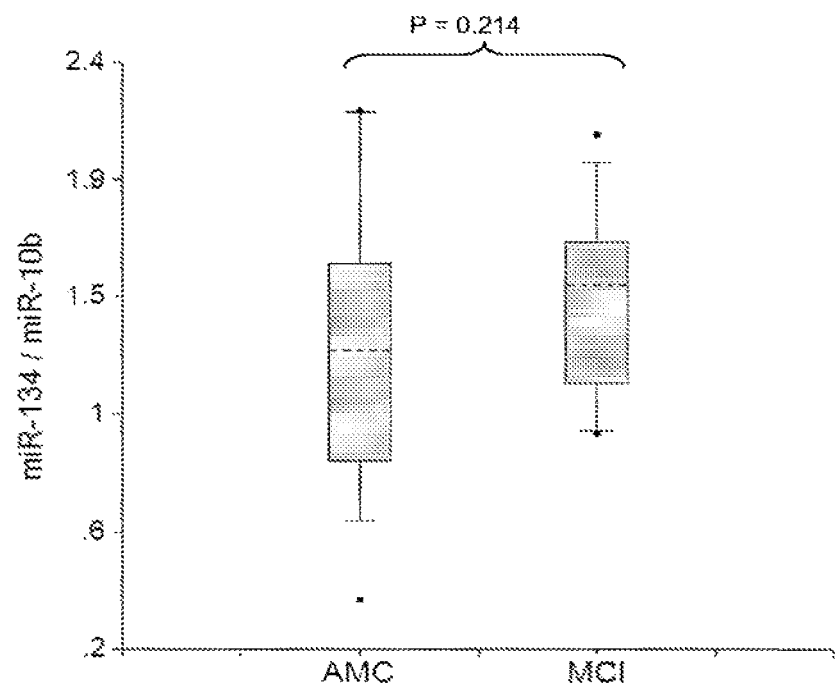
FIGS. 8A-8C are graphs showing comparison of miRNA concentrations in plasma of MCI (MCI) and age-matched controls (AMC). Concentrations of miR-134 (A), miR-874 (B), miR-539 (C) were normalized per miR-10b.
Figure 8B:
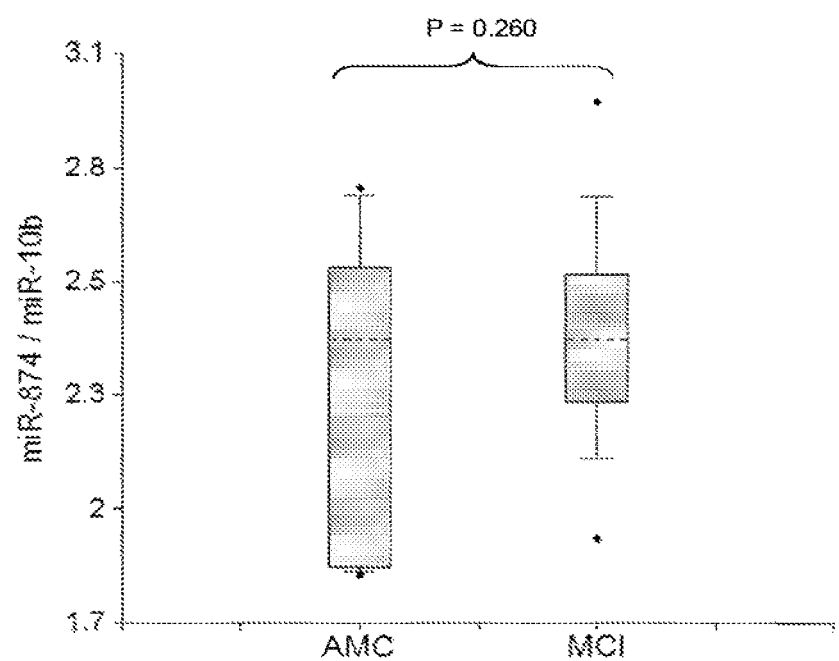
Figure 8C:
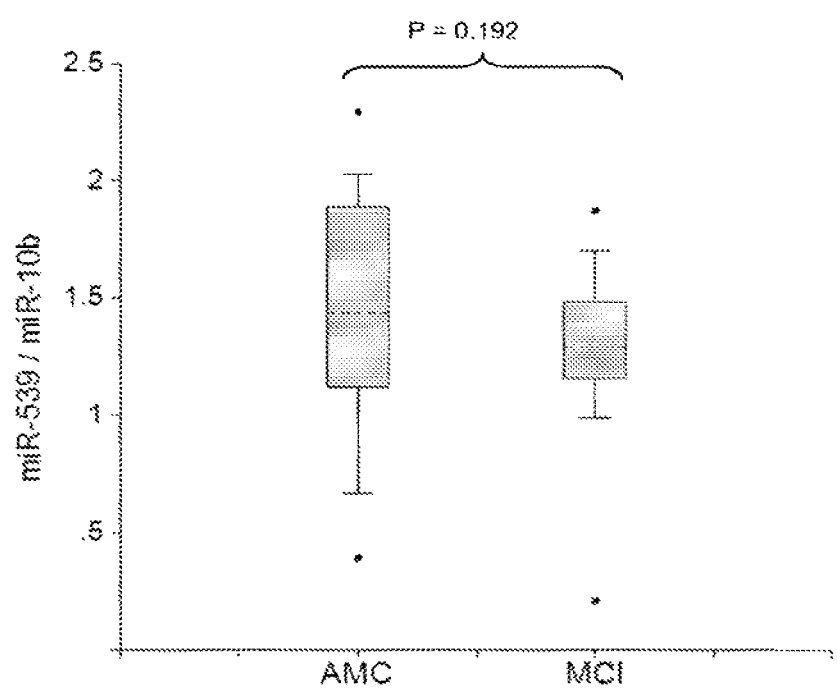
Figure 9A:
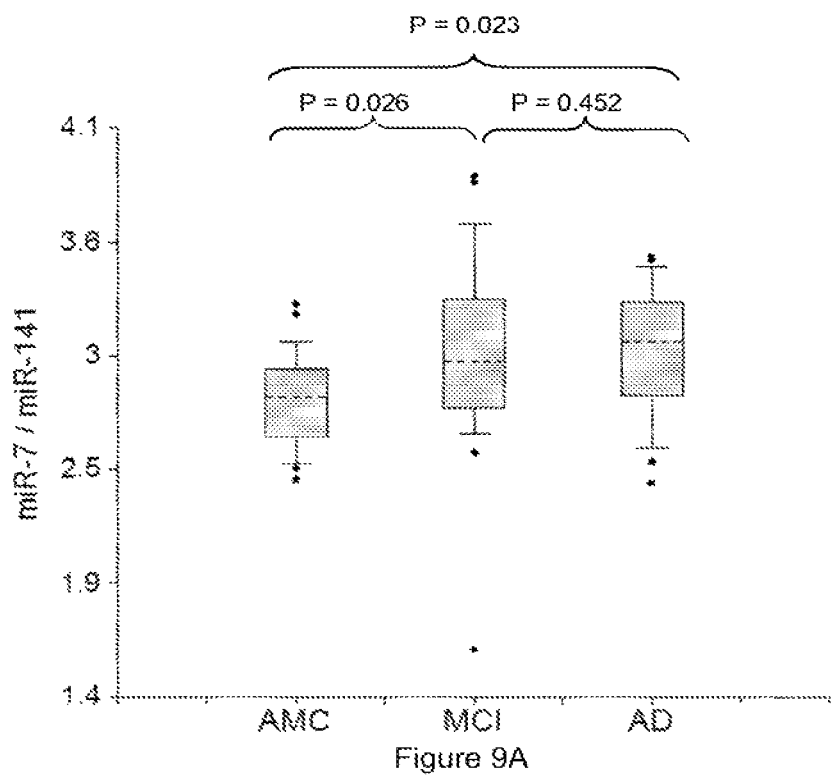
FIGS. 9A-9C are graphs showing comparison of miRNA concentrations in plasma of MCI (MCI) and AD patients (AD) and age-matched controls (AMC). Concentrations of miR-7 (A), miR-132 (B), miR-874 (C) were normalized per miR-141.
Figure 9B:
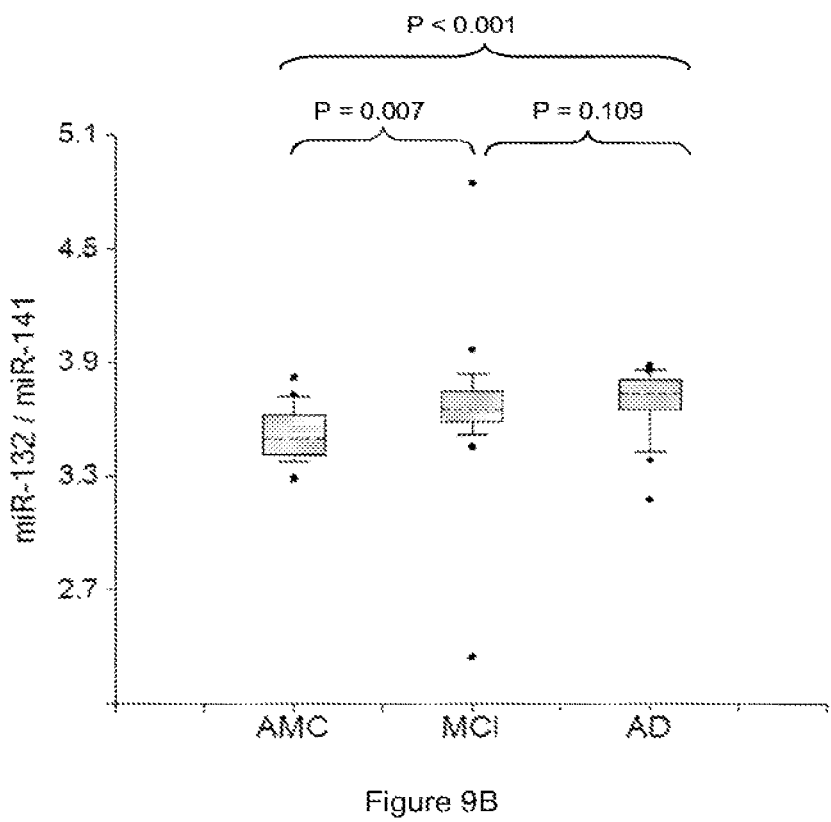
Figure 9C:
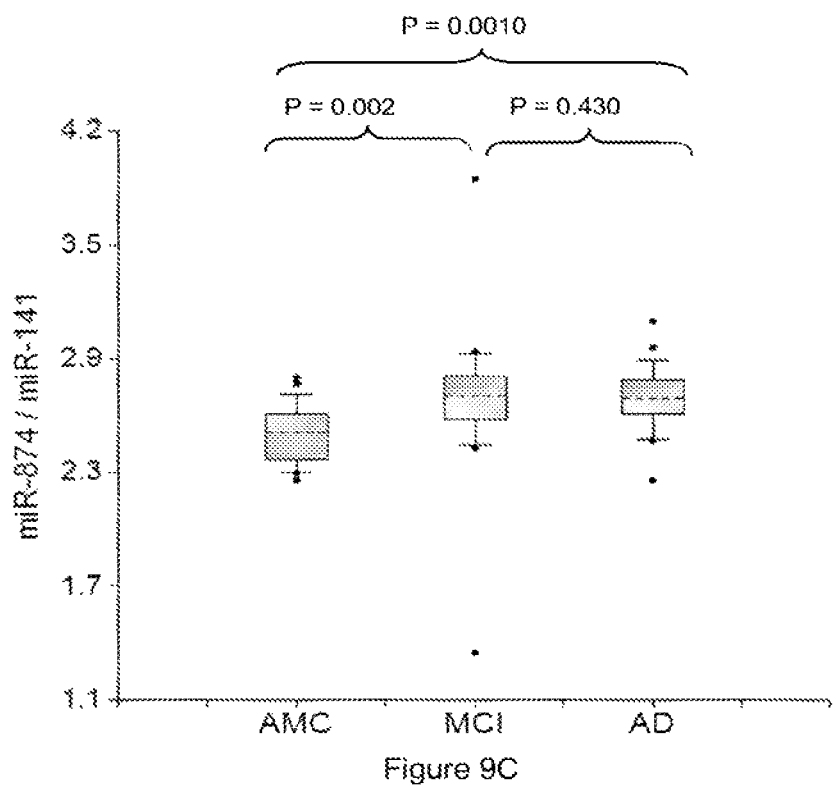
Figure 10A:
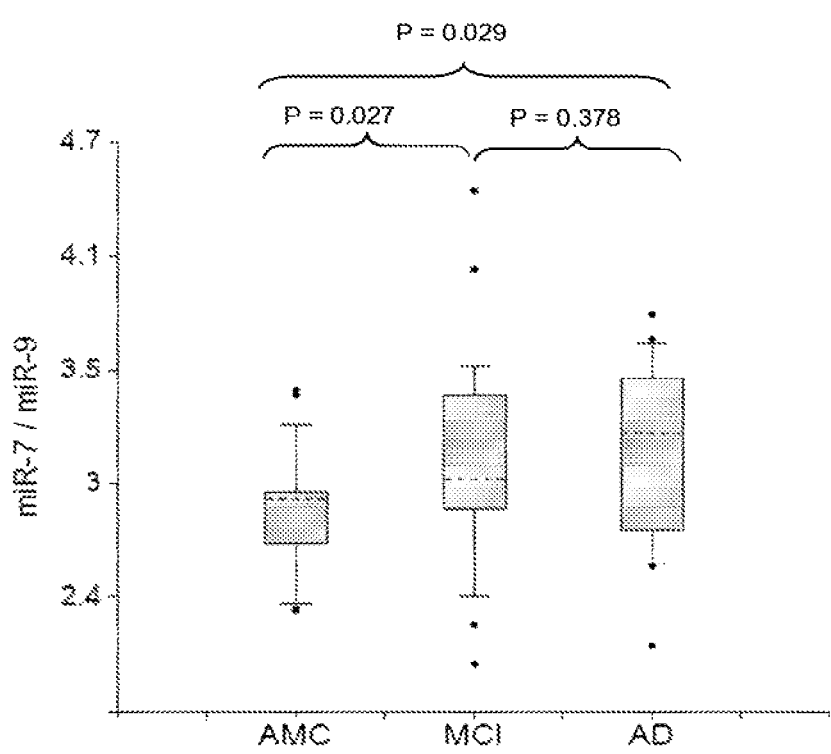
FIGS. 10A-10E are graphs showing comparison of miRNA concentrations in plasma of MCI (MCI) and AD patients (AD) and age-matched controls (AMC). Concentrations of miR-7 (A), miR-128 (B), miR-132 (C), miR382 (D), miR-874 (E) were normalized per miR-9.
Figure 10B:
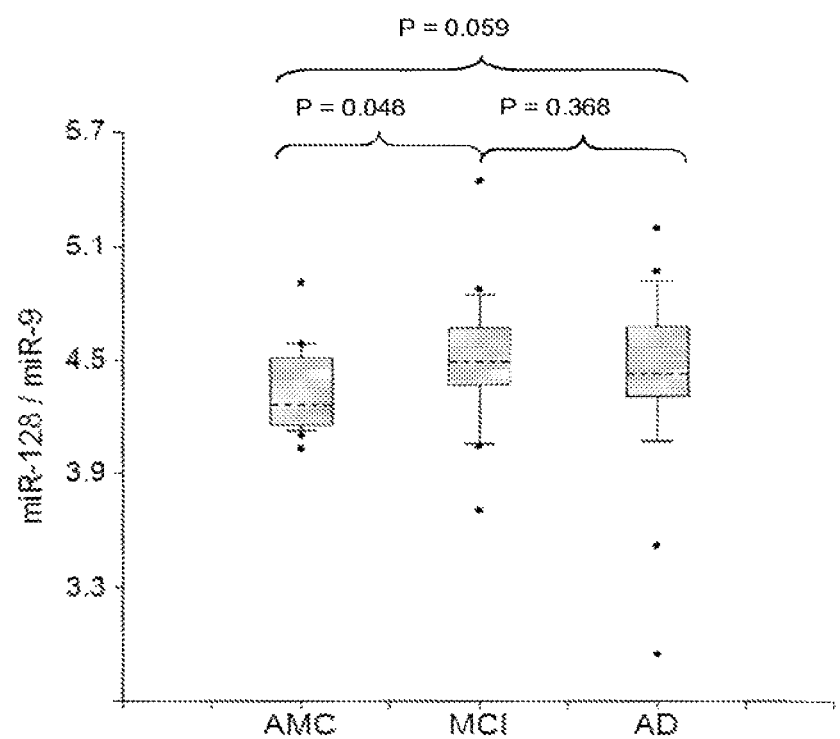
Figure 10C:
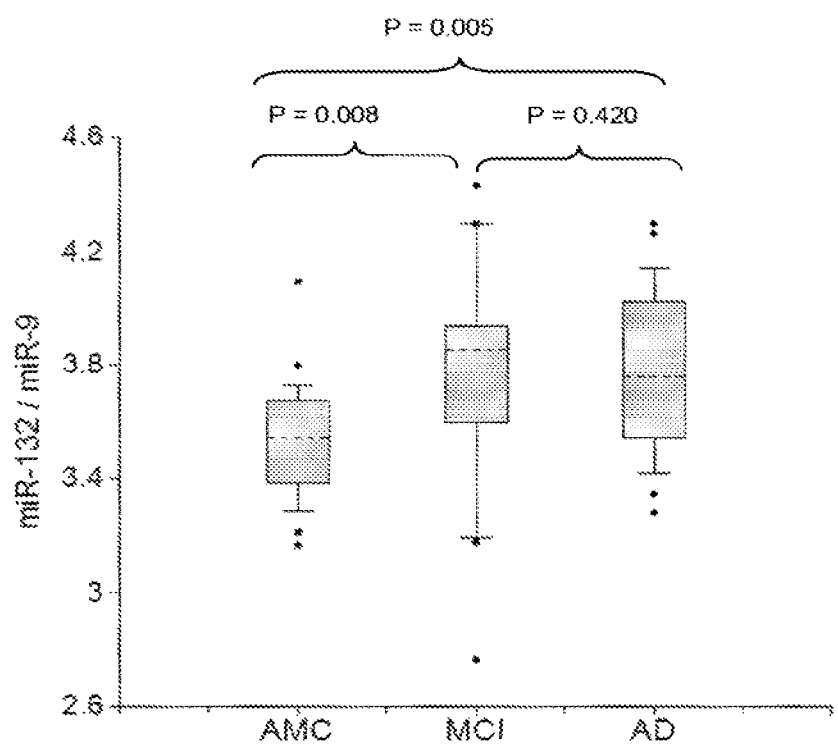
Figure 10D:
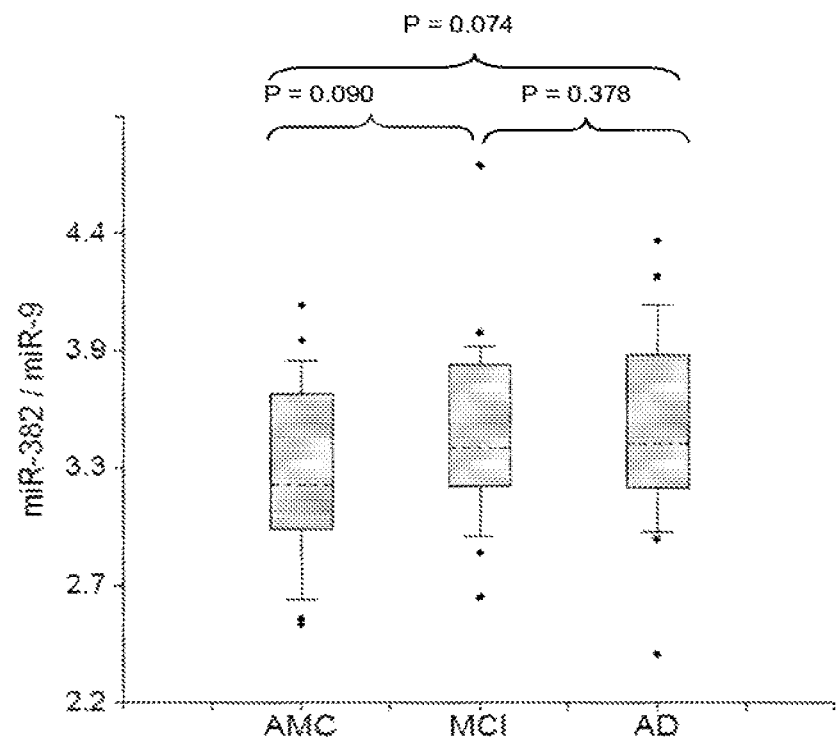
Figure 10E:
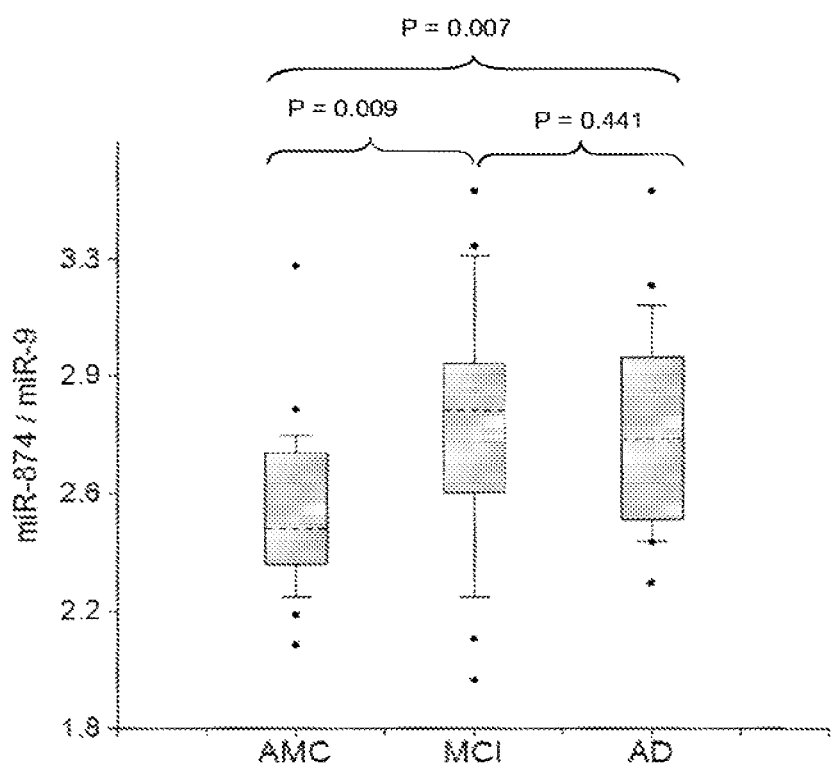
Figure 11A:
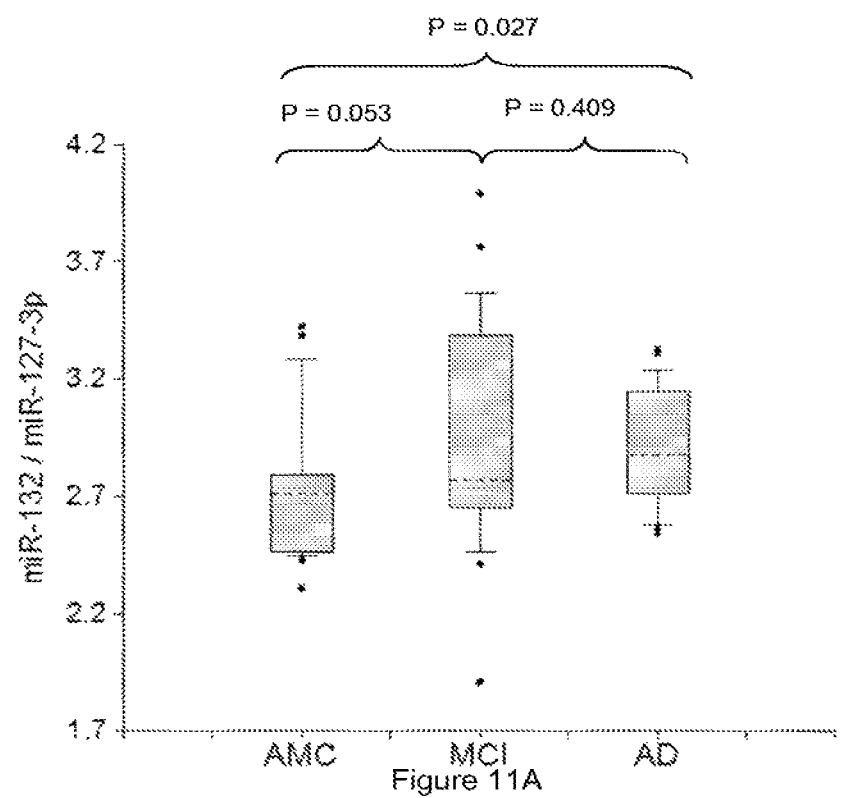
FIGS. 11A-11E are graphs showing comparison of miRNA concentrations in plasma of MCI and AD patients and age-matched controls. Concentrations of miR-132 (A), miR-134 (B), miR-323-3p (C), miR-382 (D) and miR-874 (E) were normalized per miR-127-3p.
Figure 11B:
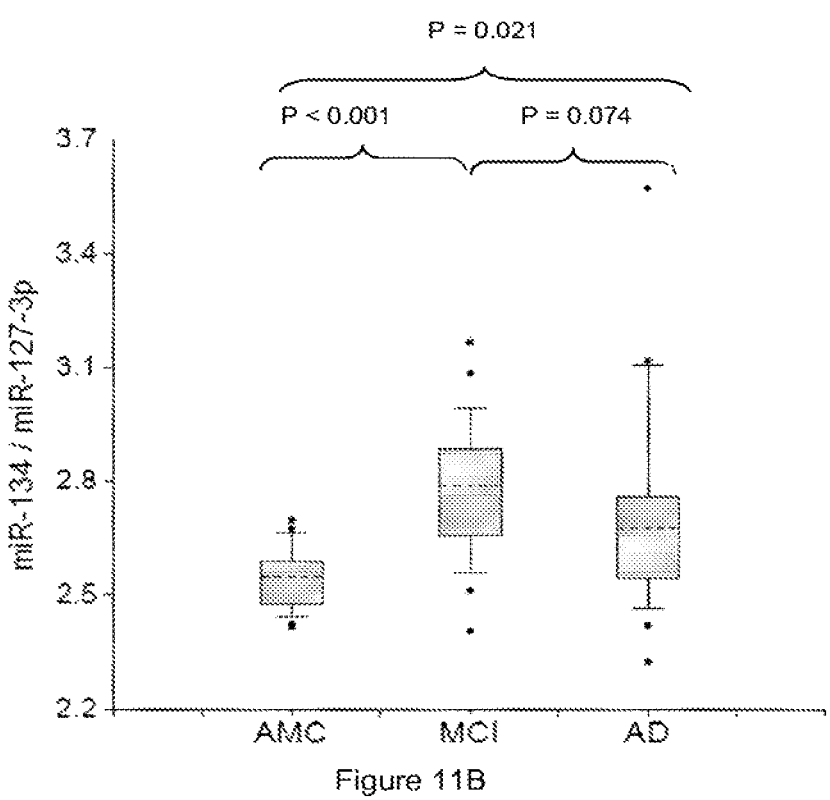
Figure 11C:
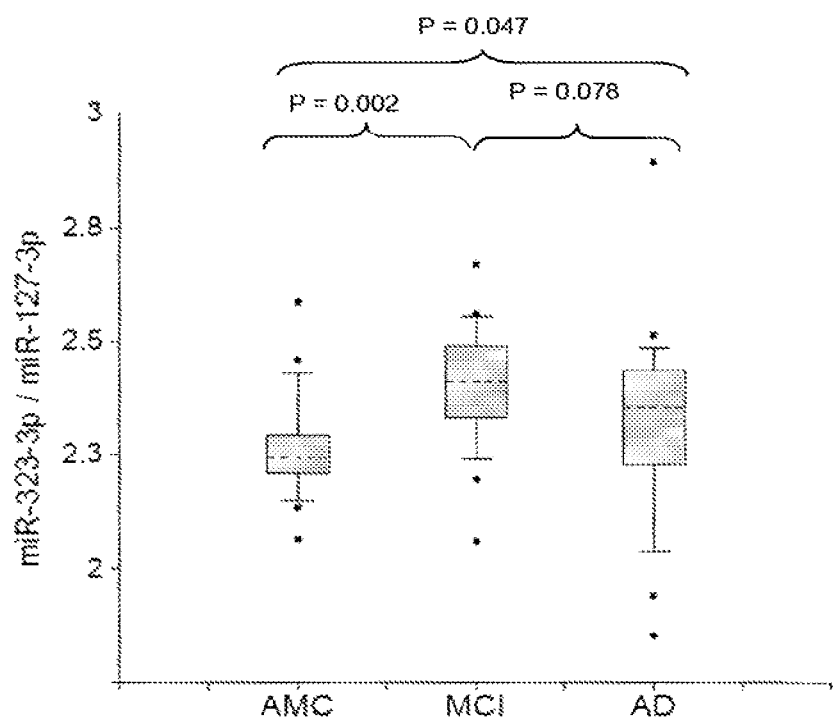
Figure 11D:
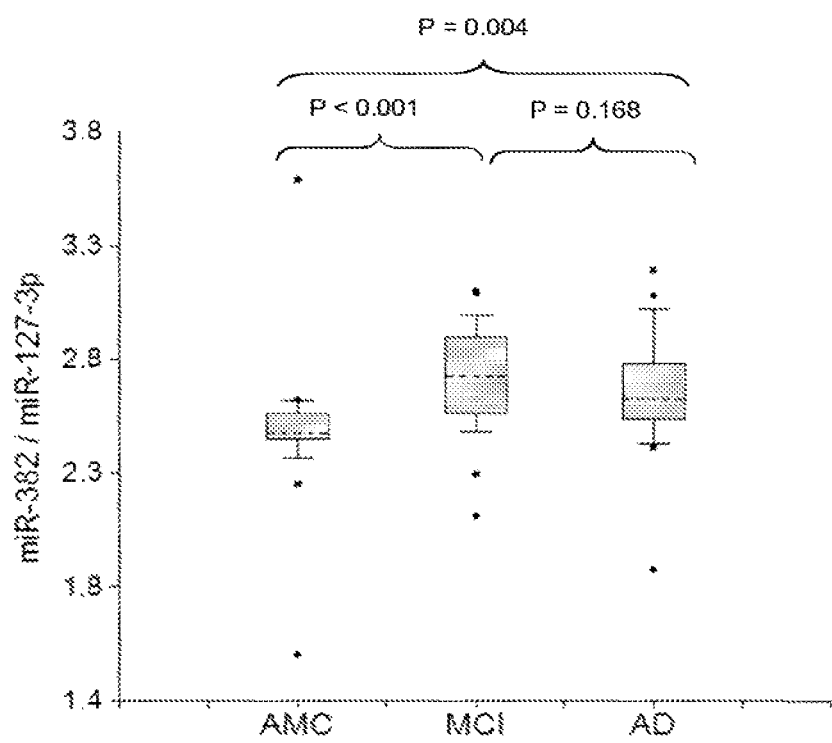
Figure 11E:
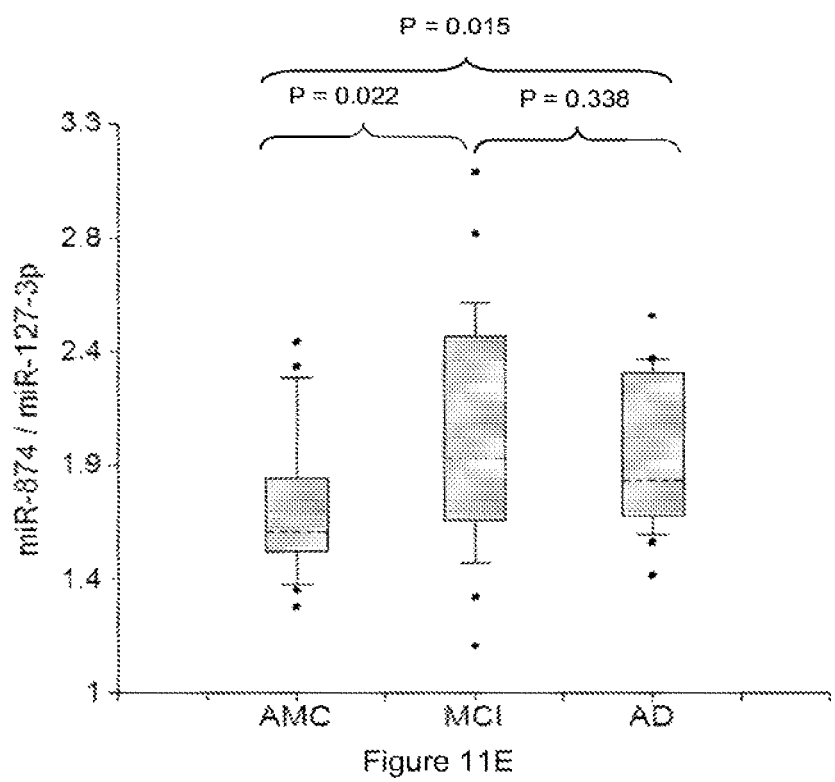
Figure 12A:
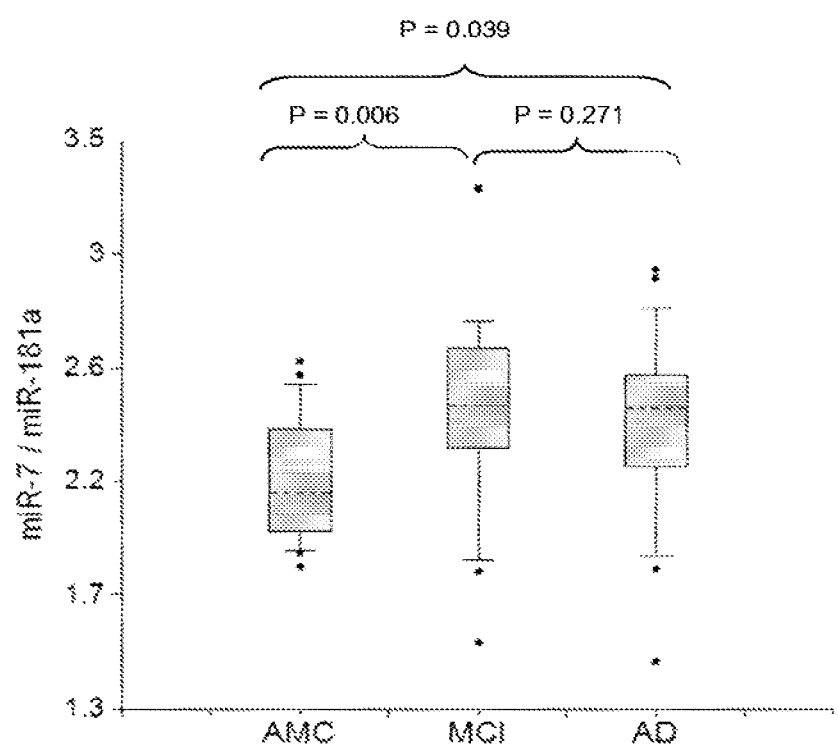
Figure 12B:
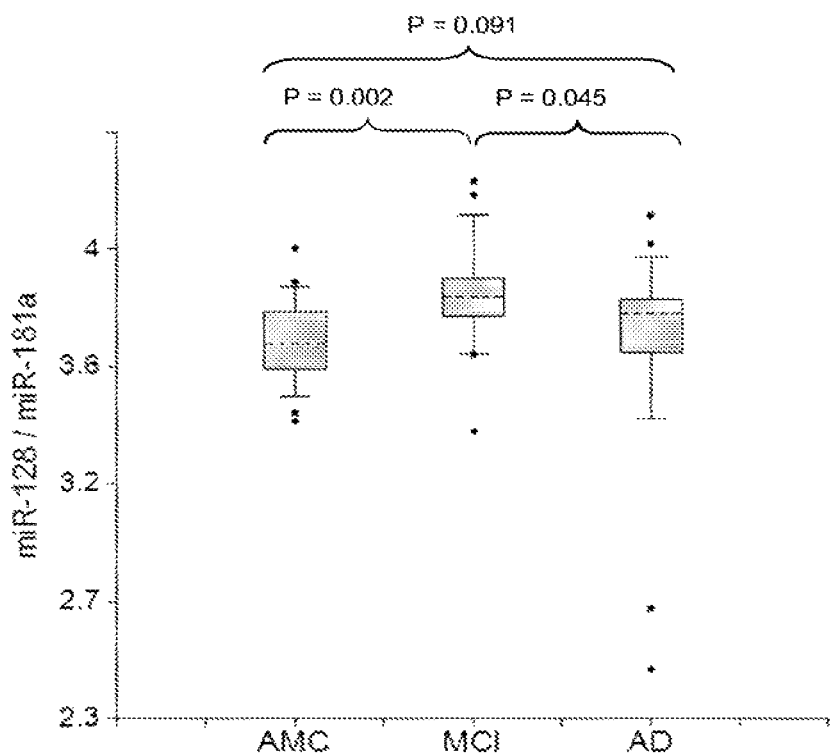
Figure 12C:
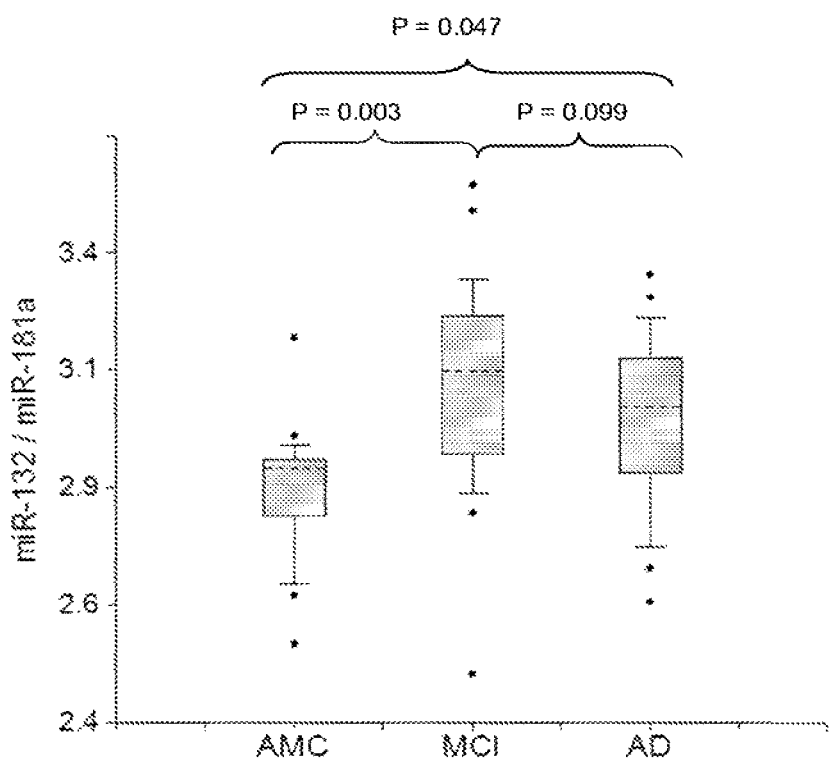
Figure 12D:
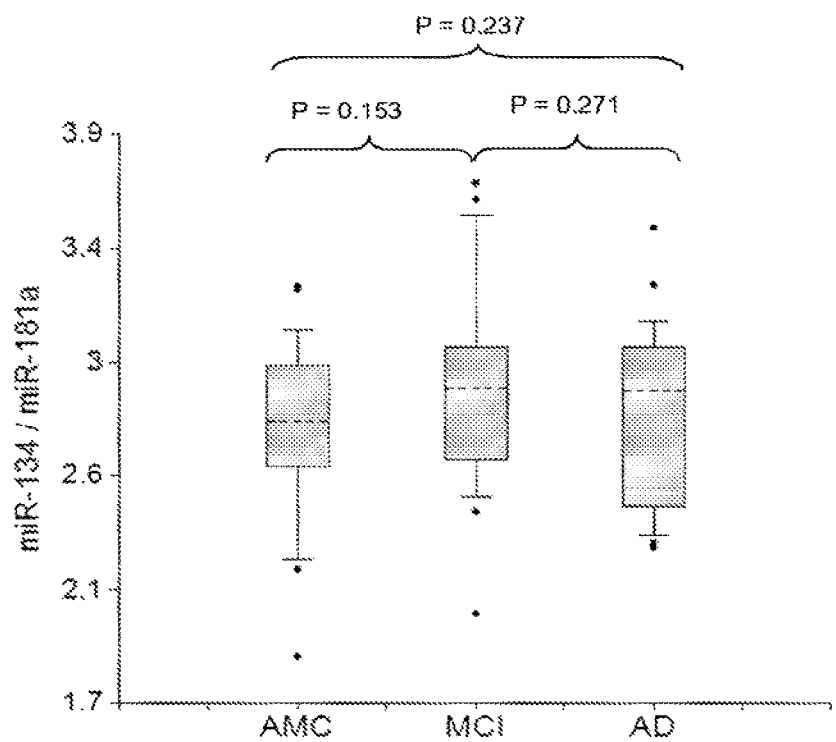
Figure 12E:
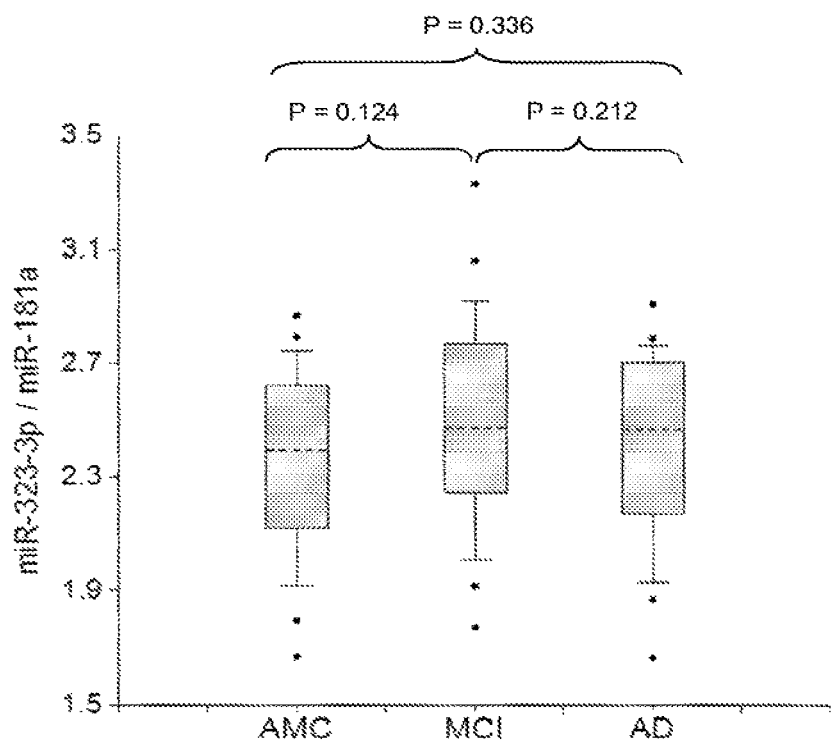
Figure 12F:
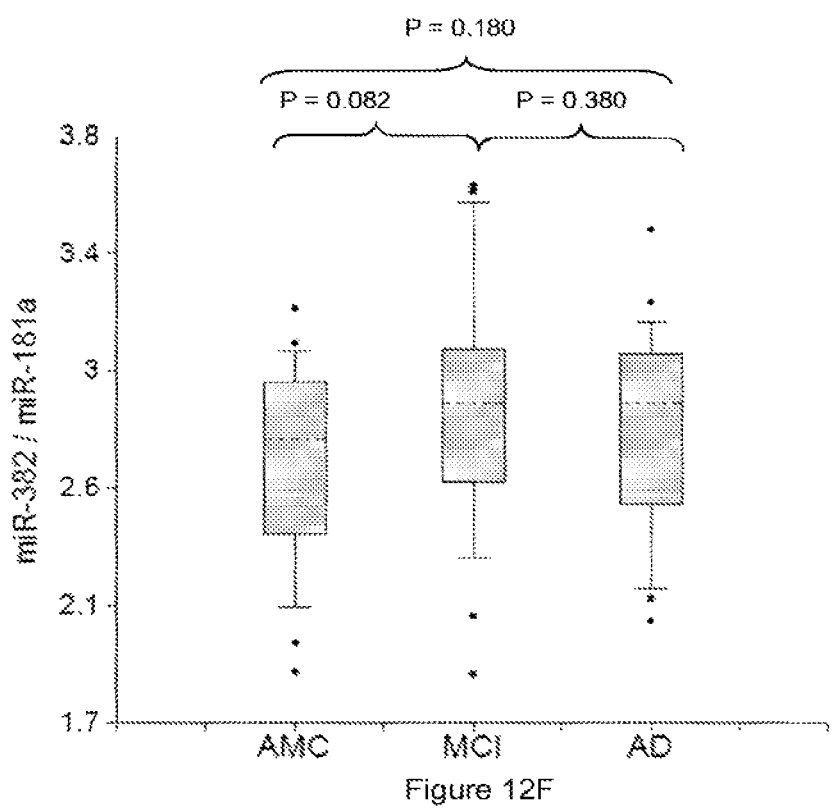
Figure 12G:
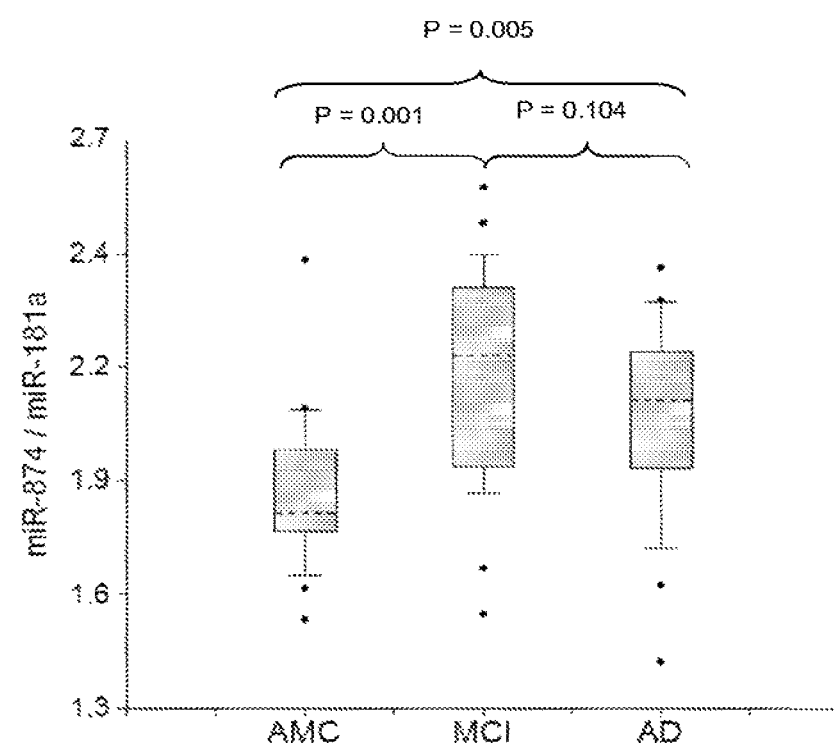
Figure 13A:
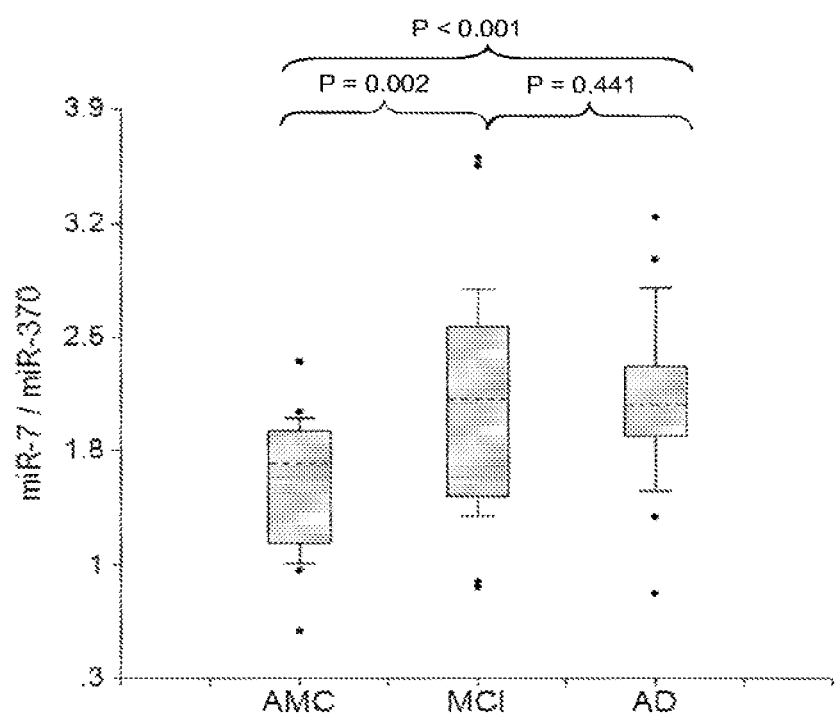
FIGS. 13A-13H are graphs showing comparison of miRNA concentrations in plasma of MCI and AD patients and age-matched controls. Concentrations of miR-7 (A), miR-125 (B), miR-128 (C), miR-132 (D), miR-134 (E), miR323-3p (F), miR-382 (G), and miR-874 (H) were normalized per miR-370.
Figure 13B:
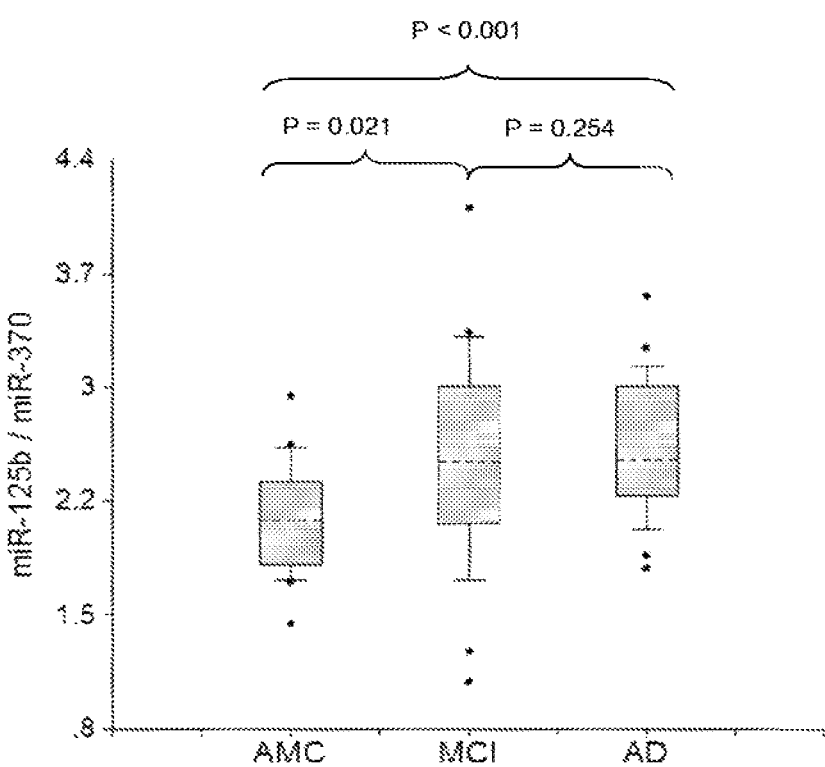
Figure 13C:
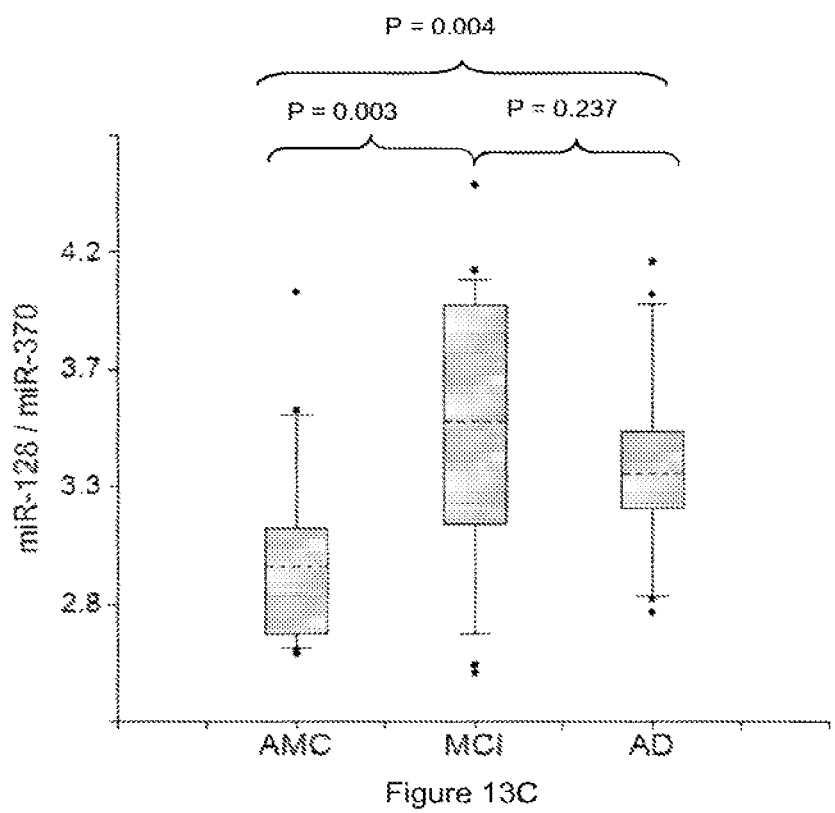
Figure 13D:
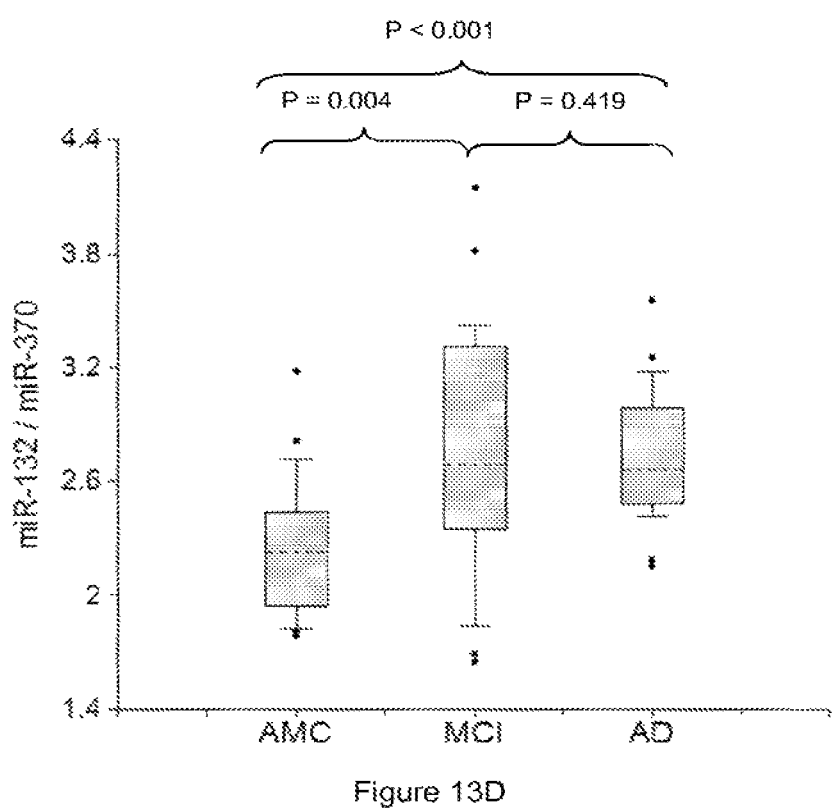
Figure 13E:
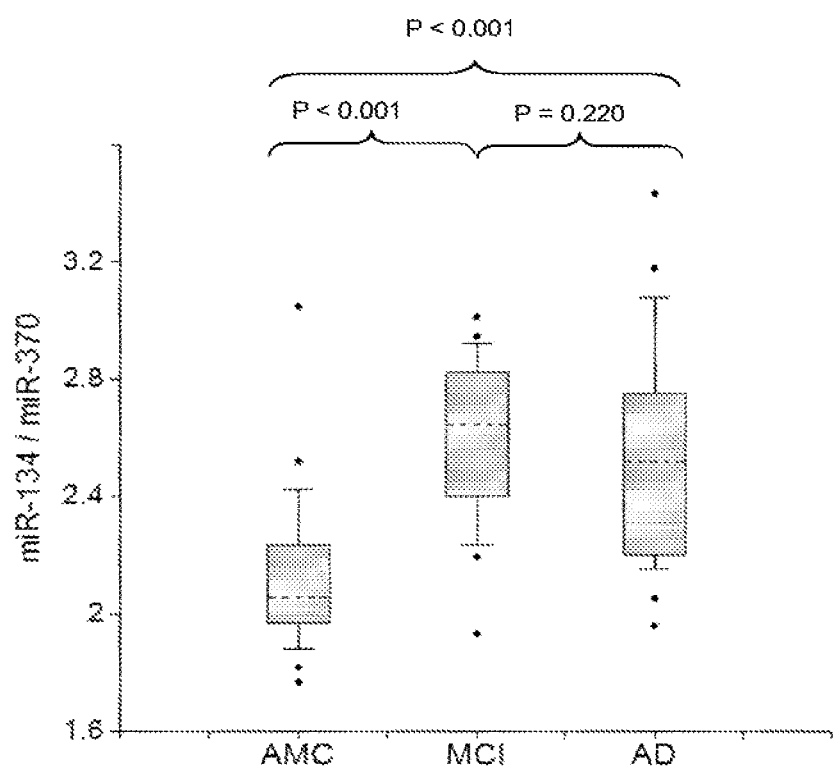
Figure 13F:
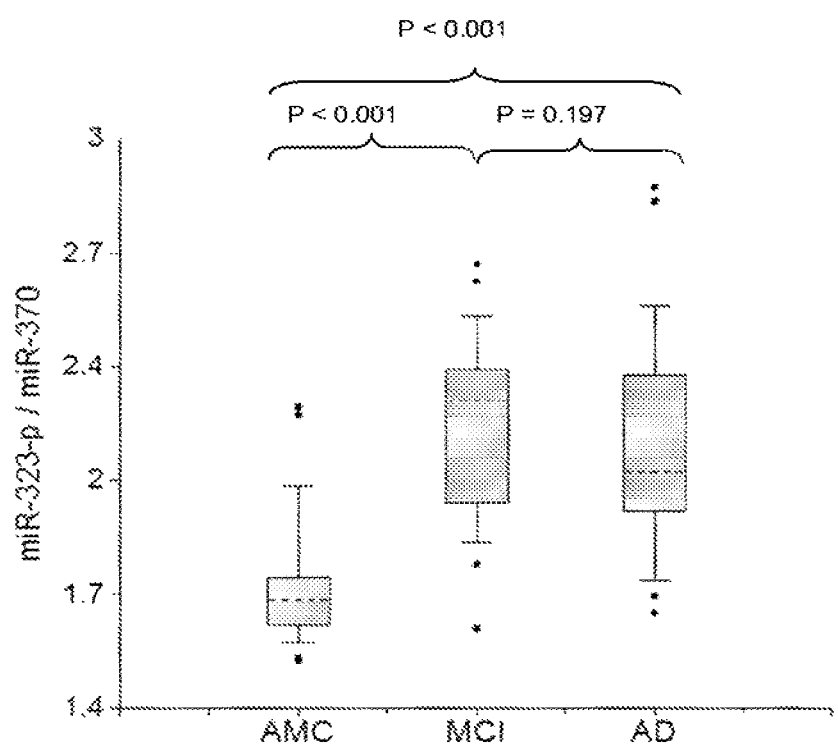
Figure 13G:
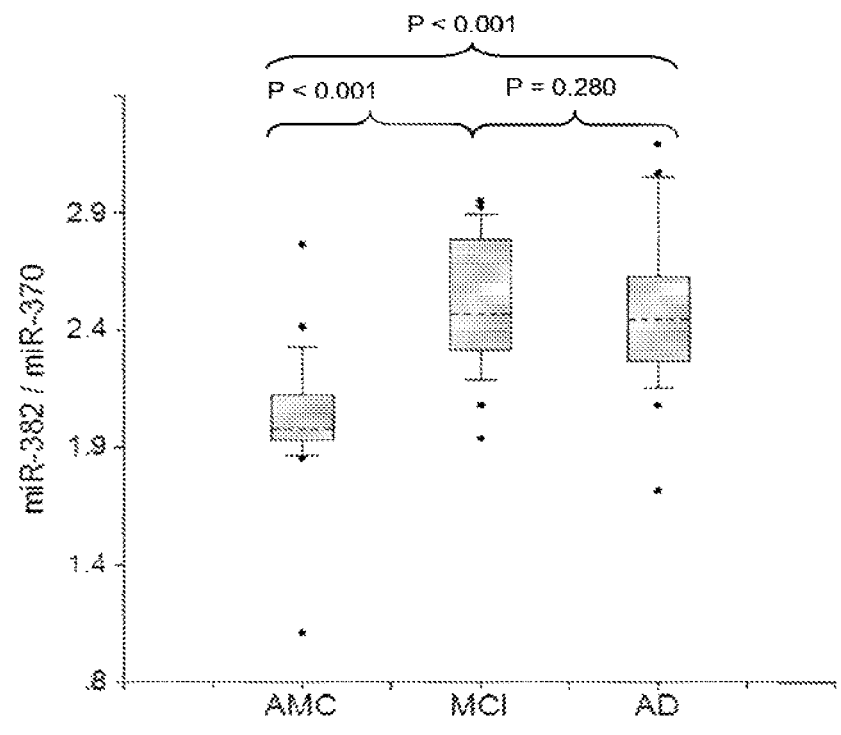
Figure 13H:
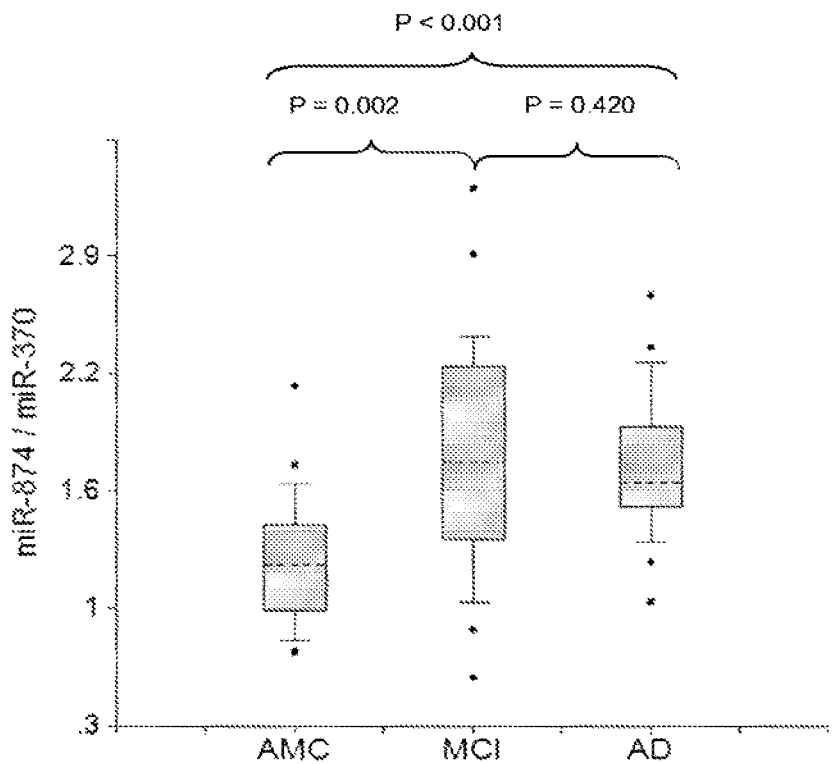
Figure 14A:
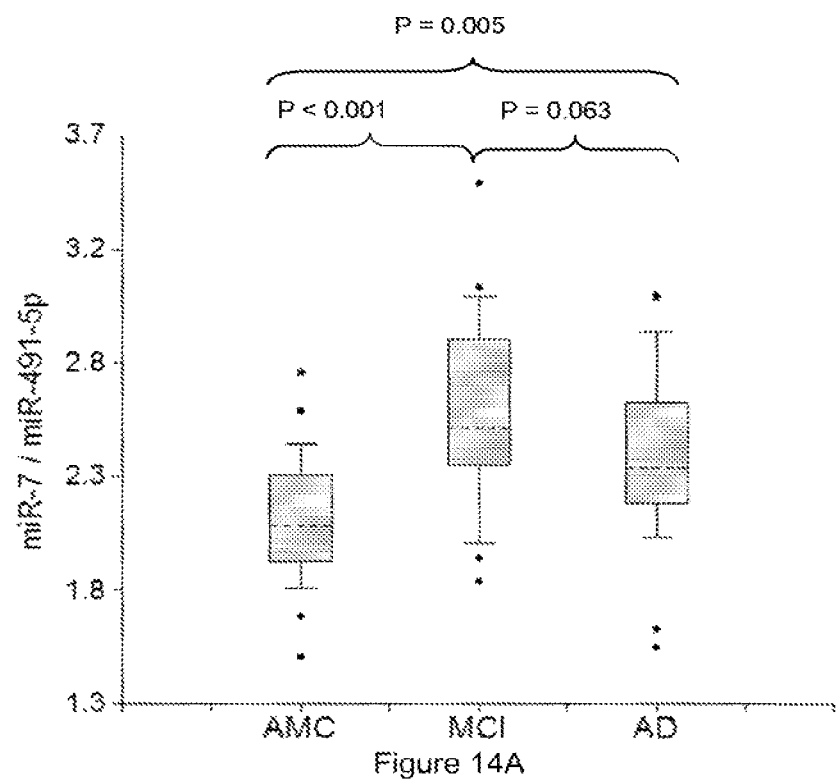
FIGS. 14A-14H are graphs showing comparison of miRNA concentrations in plasma of MCI and AD patients and age-matched controls. Concentrations of miR-7 (A), miR-125 (B), miR-128 (C), miR-132 (D), miR-134 (E), miR323-3p (F), miR-382 (G), and miR-874 (H) were normalized per miR-491-5p.
Figure 14B:
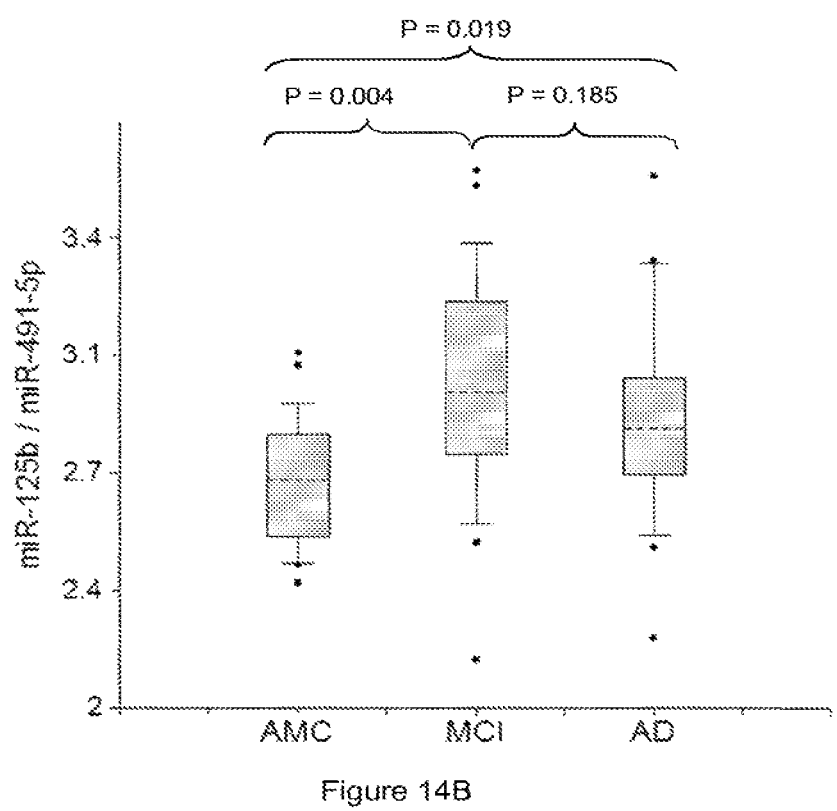
Figure 14C:
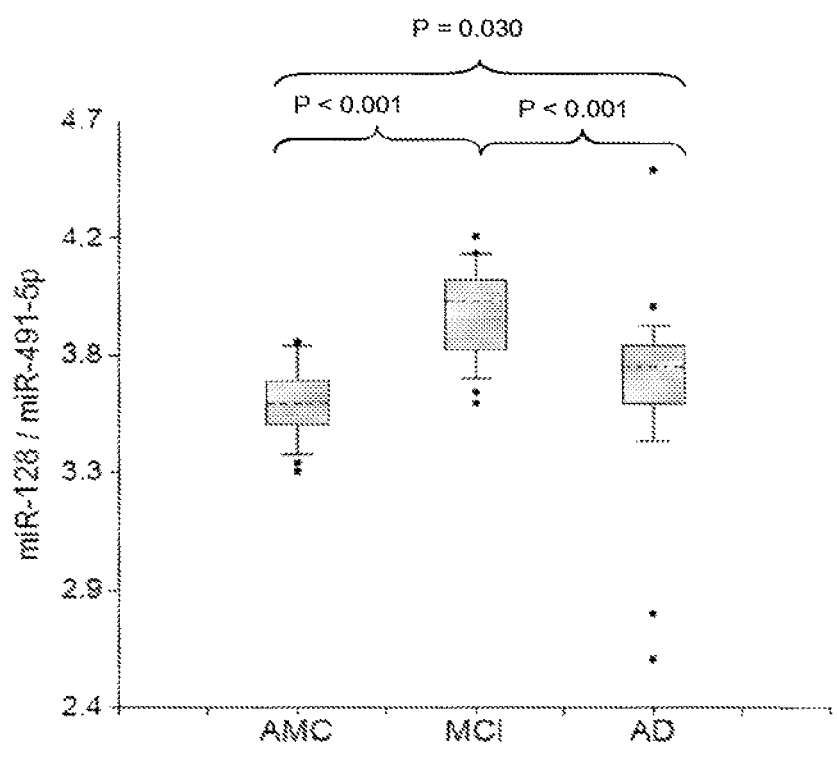
Figure 14D:
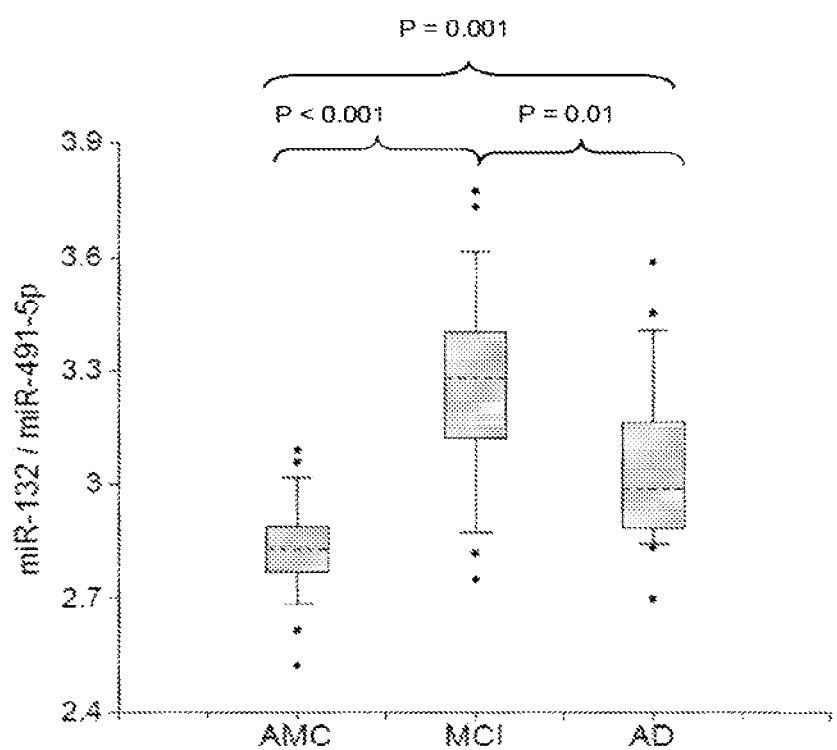
Figure 14E:
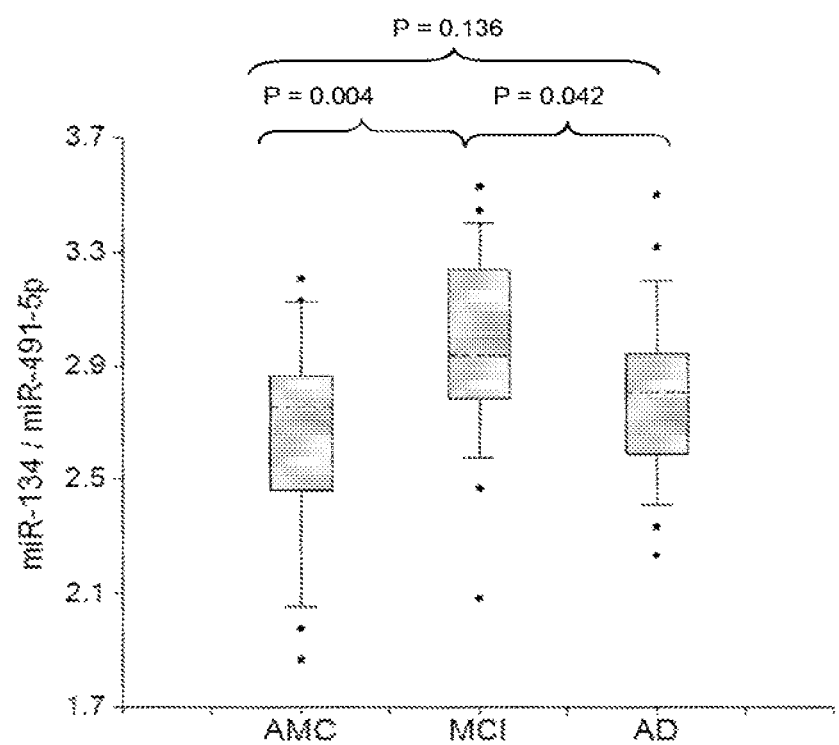
Figure 14F:
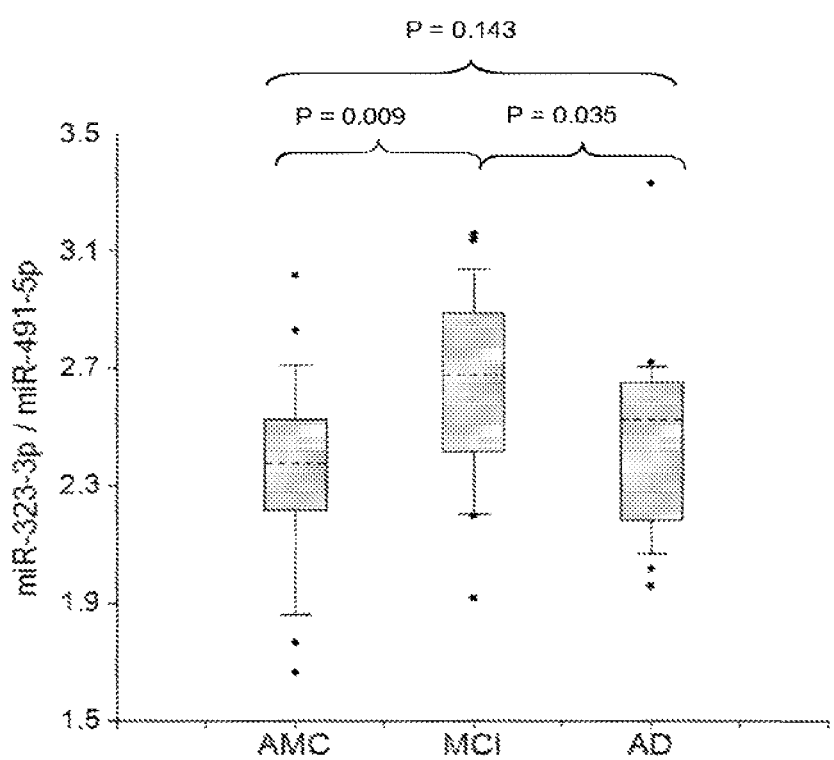
Figure 14G:
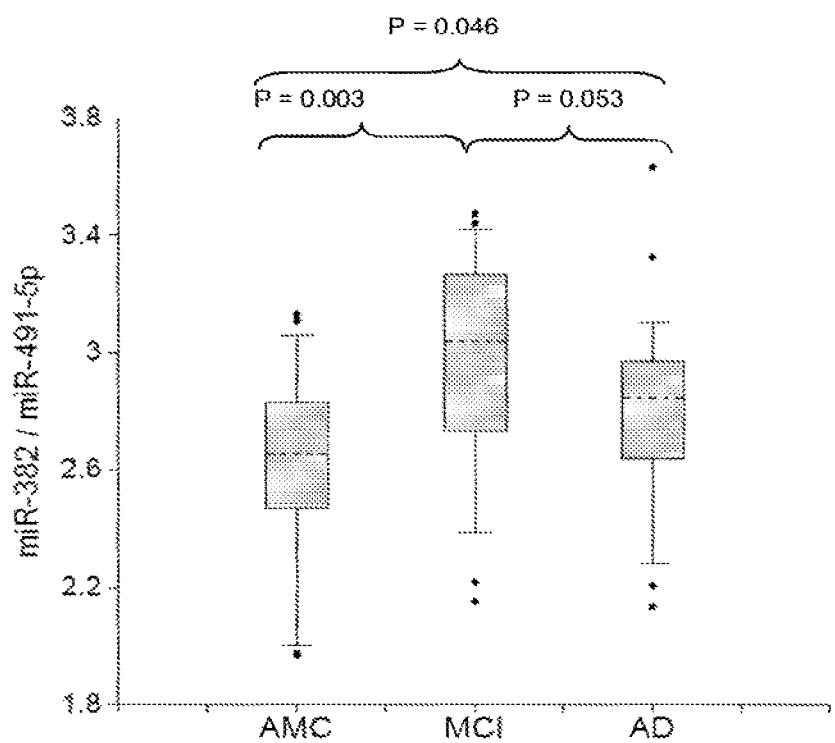
Figure 14H:
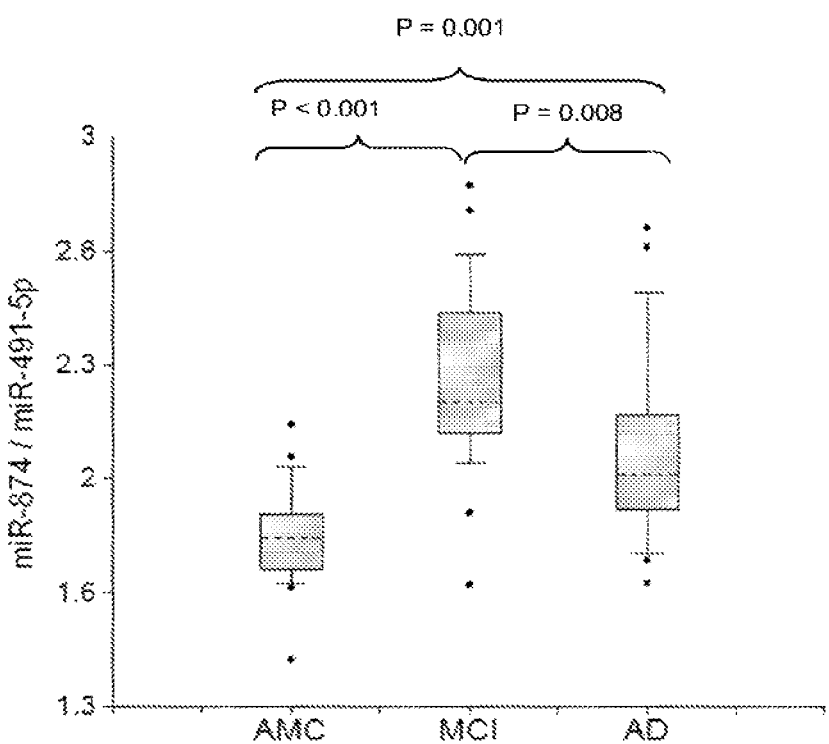

Similar results were obtained, when miRNA concentrations in plasma were normalized per miR-141 or miR-10b, which are expressed in many organs but not in the brain (FIGS. 2A-C and 8A-C). Ubiquitous miR-16 was not a good potential normalizer for differentiating MCI from AMC (FIG. 7).

At the same time, normalization of neurite/synapse miRNA concentrations in plasma per other brain-enriched miRNAs revealed several promising normalizers. Some of these normalizer miRNAs are neuronal body miRNAs, others are mainly expressed in brain areas not involved in the pathology, or in glial cells. It is also possible that some of them are downregulated in the pathology.

FIGS. 3A-C, 4, 5A-C and 6 present examples of the results obtained with various neurite/synapse miRNA concentrations in plasma of MCI and AD patients versus controls after normalization per brain-enriched miR-181a, miR-9, miR-491-5p, and miR-127, respectively. Based on data obtained 8 neurite/synapse miRNAs (miR-7, miR-125b, miR-128, miR-132, miR-134, miR-323-3p, miR-382, and miR-874) were selected as the most promising biomarkers and 7 miRNAs (miR-9, miR-127, miR-141, miR-181a, miR-370, and miR-491-5p) were selected as potential normalizers.

Example 4: MCI Detection by Analysis of miRNAs in Plasma

Plasma from amnestic MCI patients, AD patients and age-matched controls (AMC), 20 in each group, were used in the study. RNA was isolated from two 200 μl aliquots of plasma samples by the Trizol-silica method according to an Asuragen procedure. Single target TaqMan® miRNA qRT-PCR assays (Applied Biosystems) were run using 2 μl plasma equivalents in triplicate in a reaction volume of 10 μl for final PCR for measuring concentration of a neurite/synapse miRNA biomarker as well as levels of normalizer miRNA selected as described in Example 3. miR-451 was also included in the study due to its presence in neurons, significantly higher secretion from abnormal cells (Pigati et al., PLoSOne, 2010, 5:e13515) and up-regulation in brain of fetuses with anencephaly (Zhang et al., Int. J. Biochem. Cell Biol. 2010; 42:367-374).

Data presented in FIGS. 9-14 demonstrate the 2-5 times increase in median concentrations of neurite/synapse miR-NAs (miR-7, miR-125b, miR-128, miR-132, miR-134, miR-323-3p, miR-382, miR-874) in plasma of MCI and AD patients when compared to age-matched controls. The effect is more prominent when normalization is performed per brain-enriched miRNA, such as miR-9, miR-127, miR-181a, miR-370, and miR-491-5p.

Figure 15A:
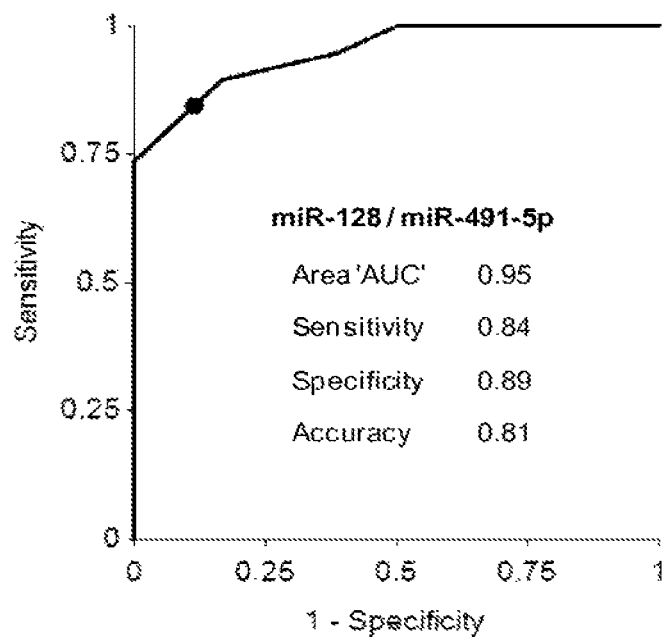
FIGS. 15A-15C present Receiver-Operating Characteristic (ROC) curve analysis of differentiation between MCI patients (MCI) and age-matched controls (AMC) obtained with miR-128 (A), miR-132 (B) and miR-874 (C) normalized per miR-491-5p. The areas under the ROC curve (AUC) are reported. Sensitivity, specificity and accuracy for each biomarker/normalizer pair are calculated for the "cutoff" point (indicated as a dot on each plot); the cutoff point is the biomarker/normalizer ratio, at which a sample is equally likely to belong to the AMC or the MCI groups.
Figure 15B:
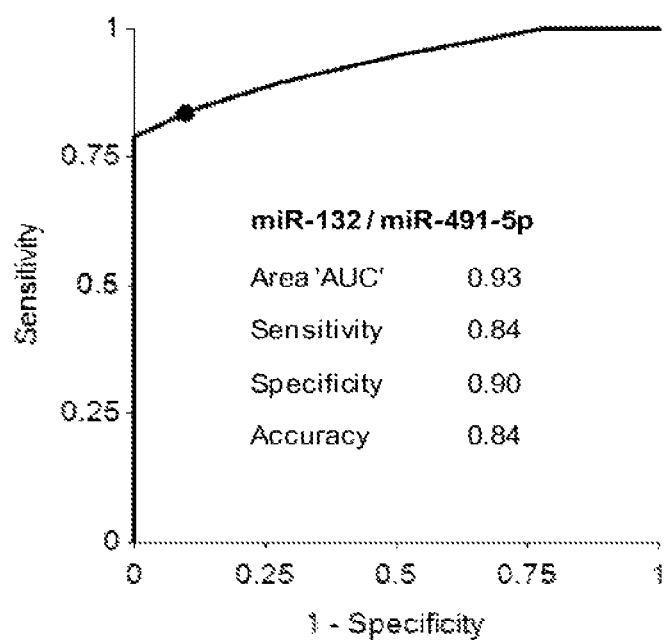
Figure 15C:
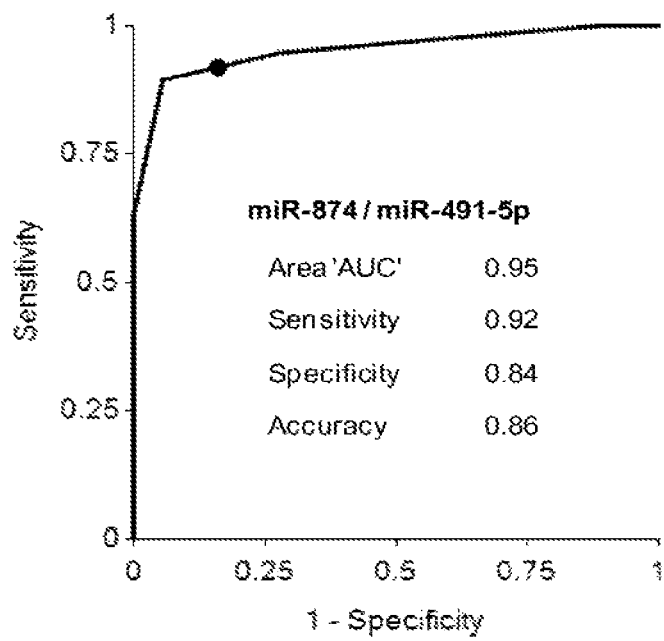
Figure 16A:
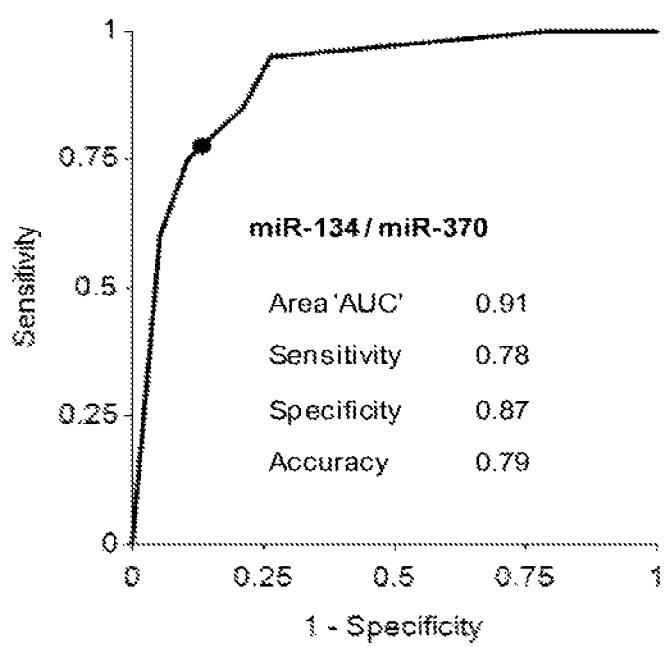
FIGS. 16A-16C present Receiver-Operating Characteristic (ROC) curve analysis of differentiation between MCI patients (MCI) and age-matched controls (AMC) obtained with miR-134 (A), miR-323-3p (B) and miR-382 (C) normalized per miR-370. The areas under the ROC curve (AUC) are reported. Sensitivity, specificity and accuracy for each biomarker/normalizer pair are calculated for the "cutoff" point (indicated as a dot on each plot); the cutoff point is the biomarker/normalizer ratio, at which a sample is equally likely to belong to the AMC or the MCI groups.
Figure 16B:
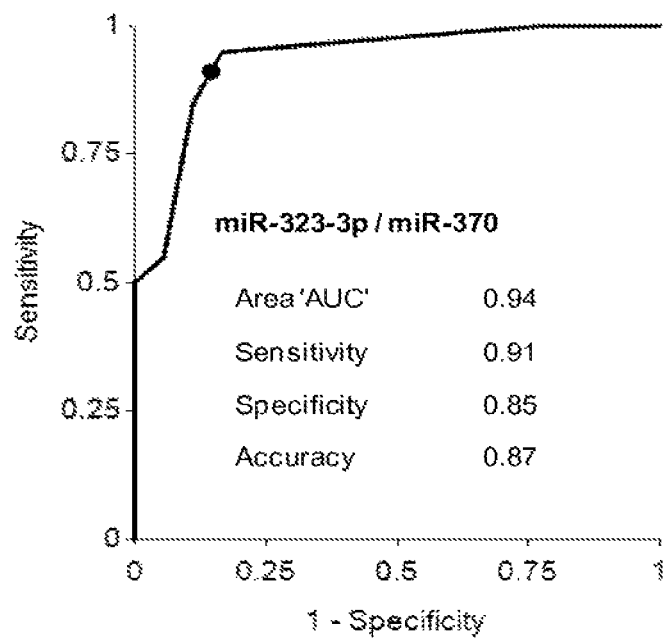
Figure 16C:
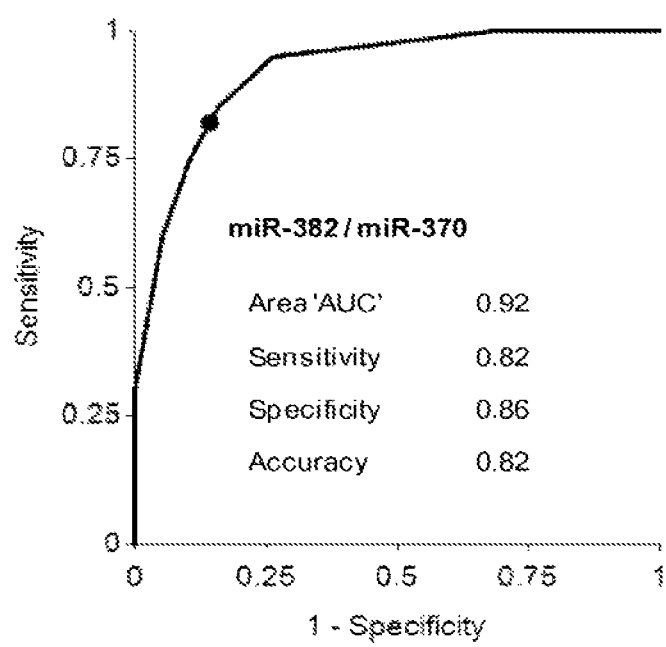
Figure 17A:
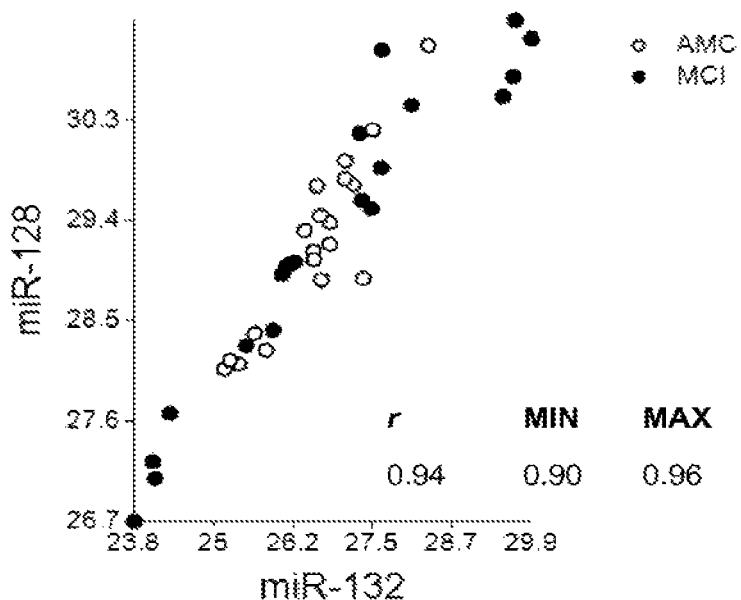
FIGS. 17A-17F present analysis of associations between miR128 and miR-132 (A), miR-128 and miR-874 (B), miR-132 and miR-874 (C), miR-134 and miR-323-3p (D), miR-134 and miR-382 (E), and miR-382 and miR-323-3p (F). The Ct values of various biomarker pairs were compared and Spearman's rank correlation coefficients r along with 95% confidence intervals (MIN & MAX) were calculated.
Figure 17B:
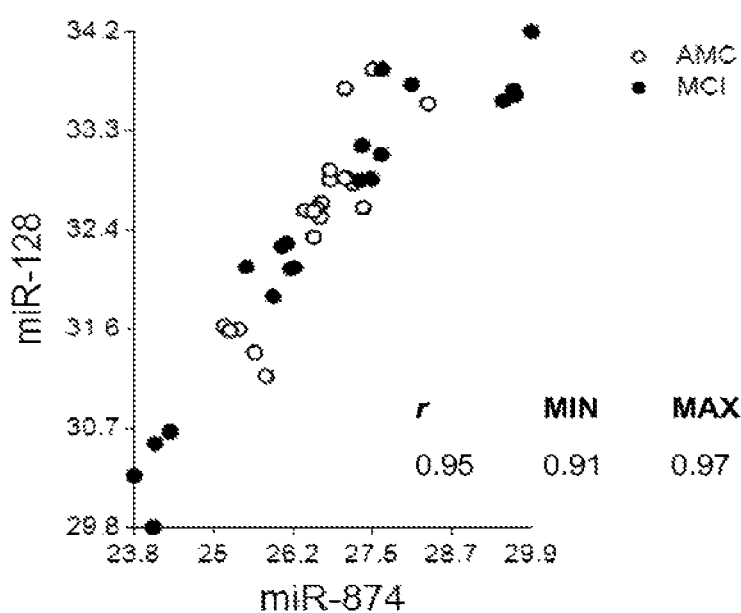
Figure 17C:
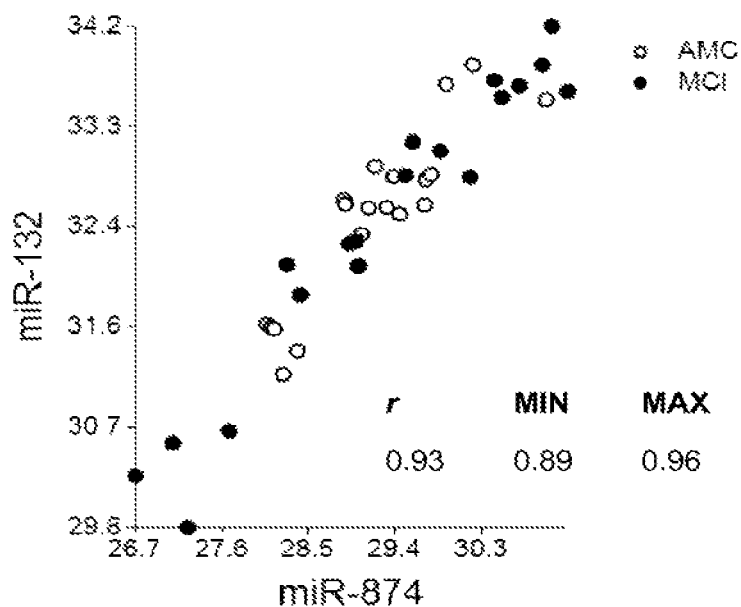
Figure 17D:
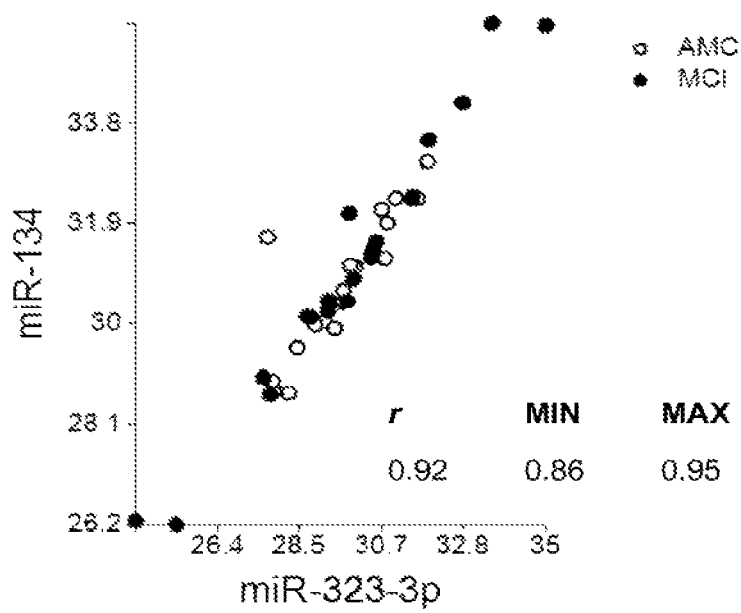
Figure 17E:
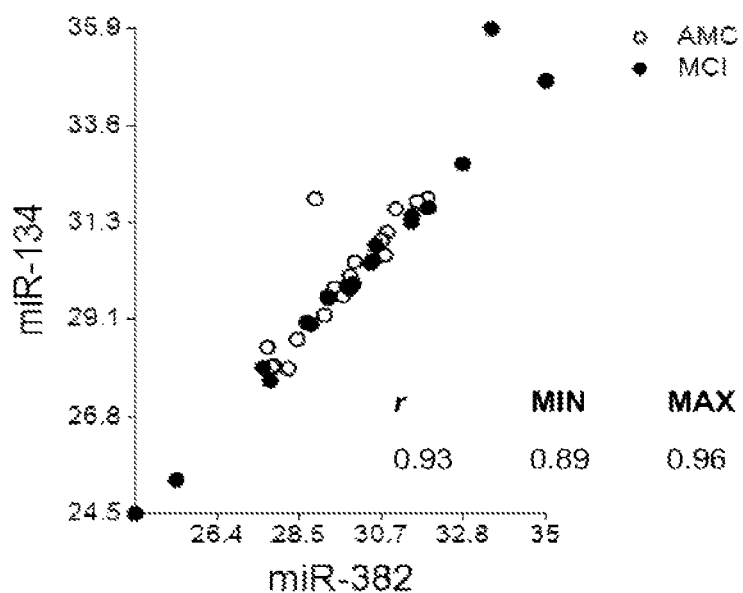
Figure 17F:
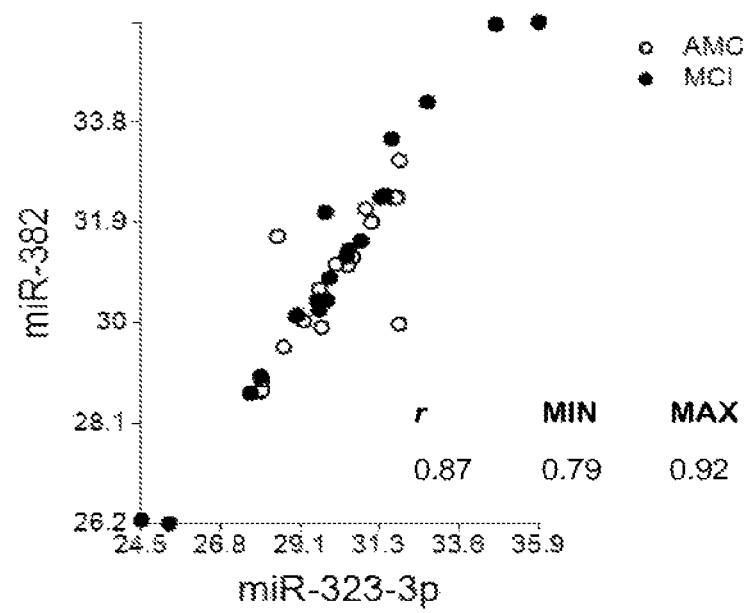
Figure 18A:
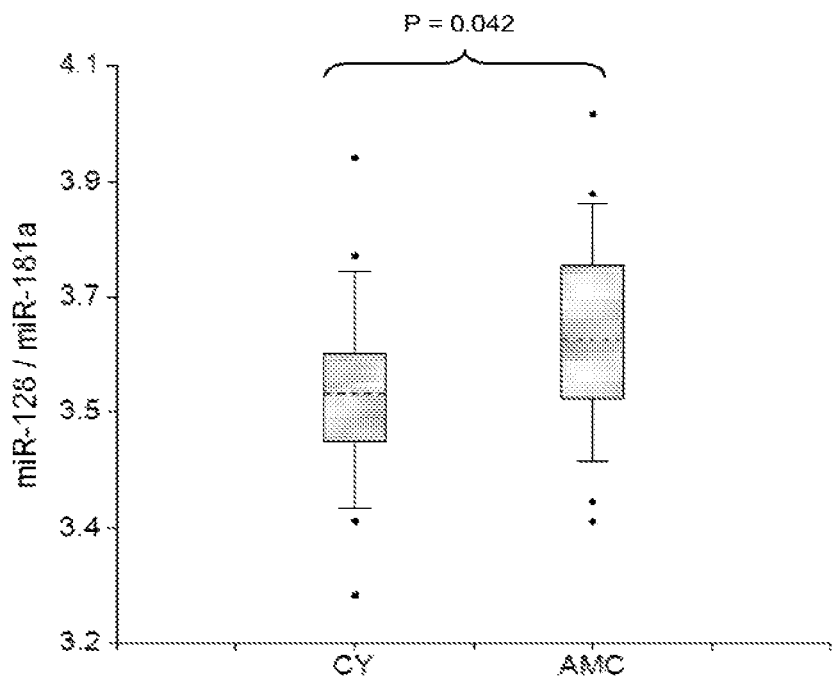
FIGS. 18A-18J are graphs showing comparison of miRNA concentrations in plasma of 21-50 (CY) and 76-86 (CO) years old controls. Concentrations of biomarker miRNAs were normalized per various miRNA normalizers and presented in relative units (ordinate axis). A: miR-128/miR-181a; B: miR-132/miR-181a; C: miR-874/miR-181a; D: miR-134/miR-370; E: miR-323-3p/miR-370; F: miR-382/miR-370; G: miR-132/miR-9; H: miR-382/miR-127-3p; I: miR-132/miR-491-5p; J: miR-874/miR-491-5p.
Figure 18B:
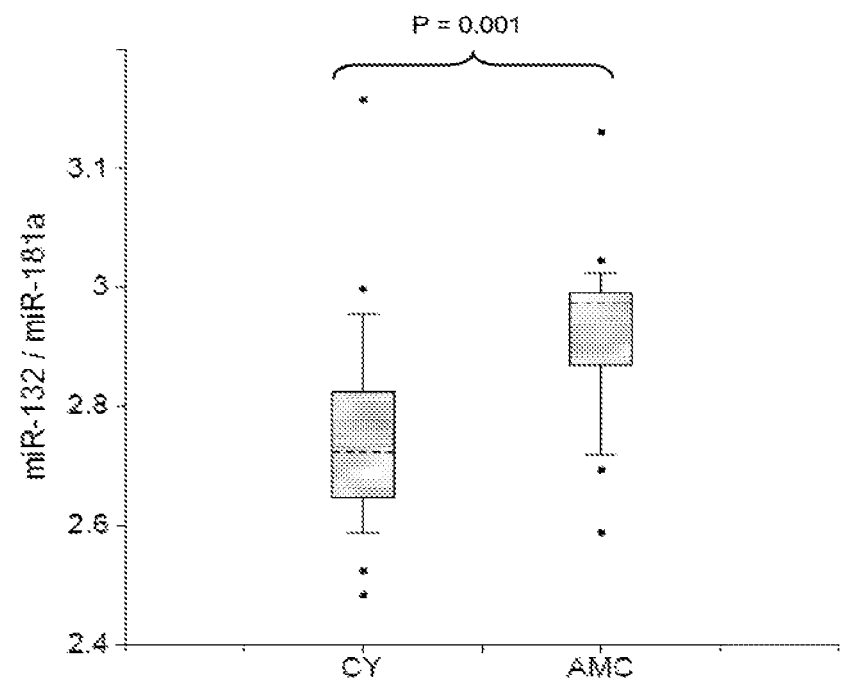
Figure 18C:
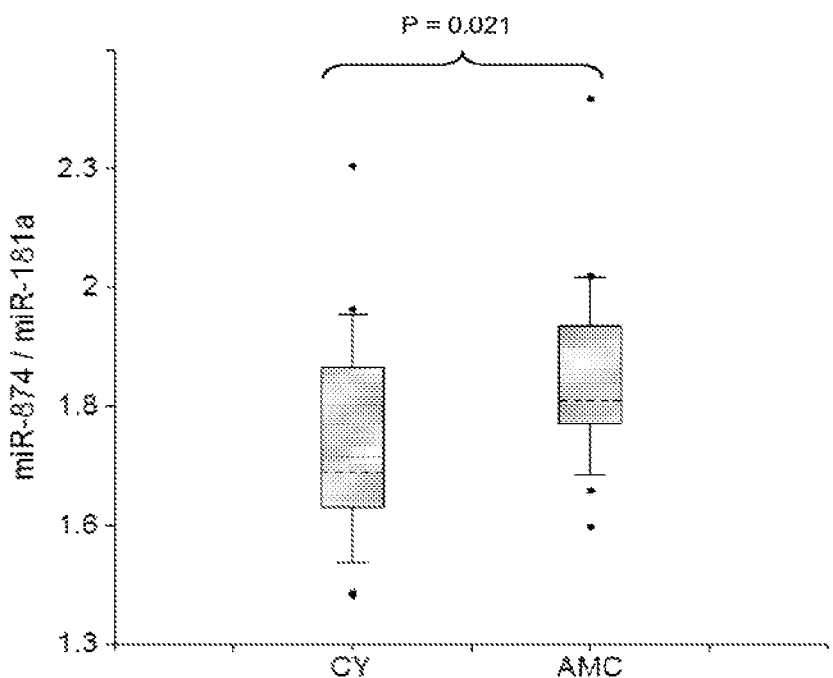
Figure 18D:
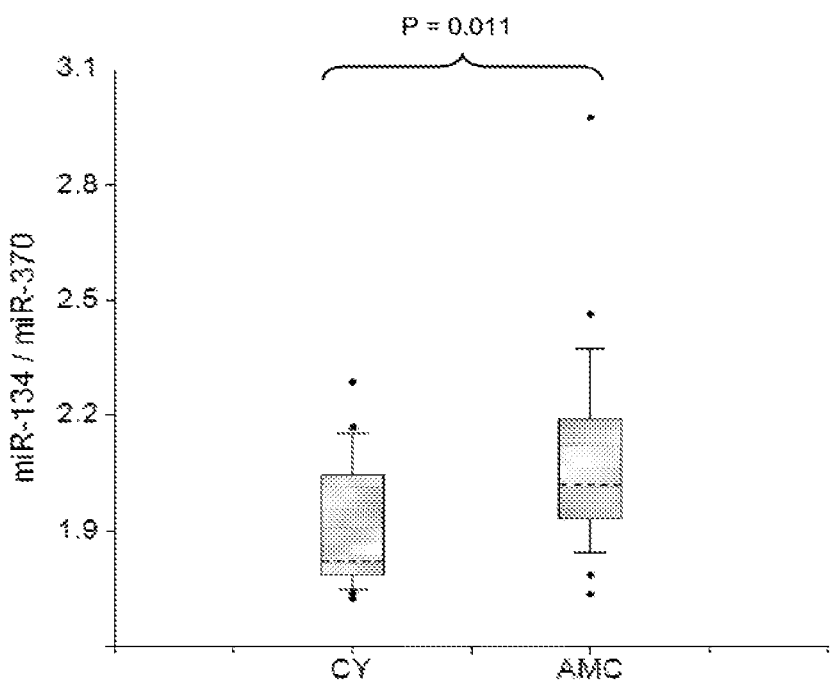
Figure 18E:
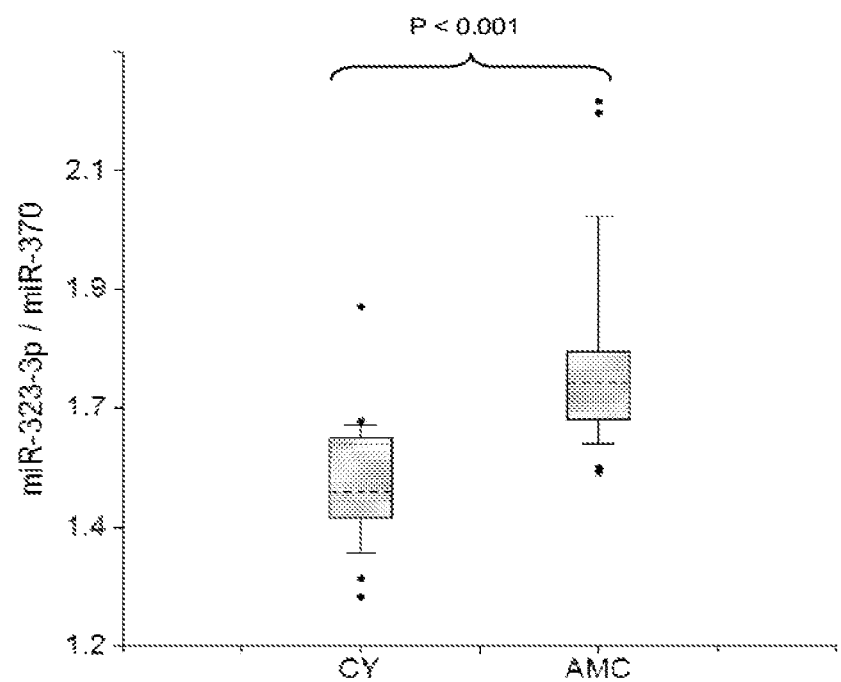
Figure 18F:
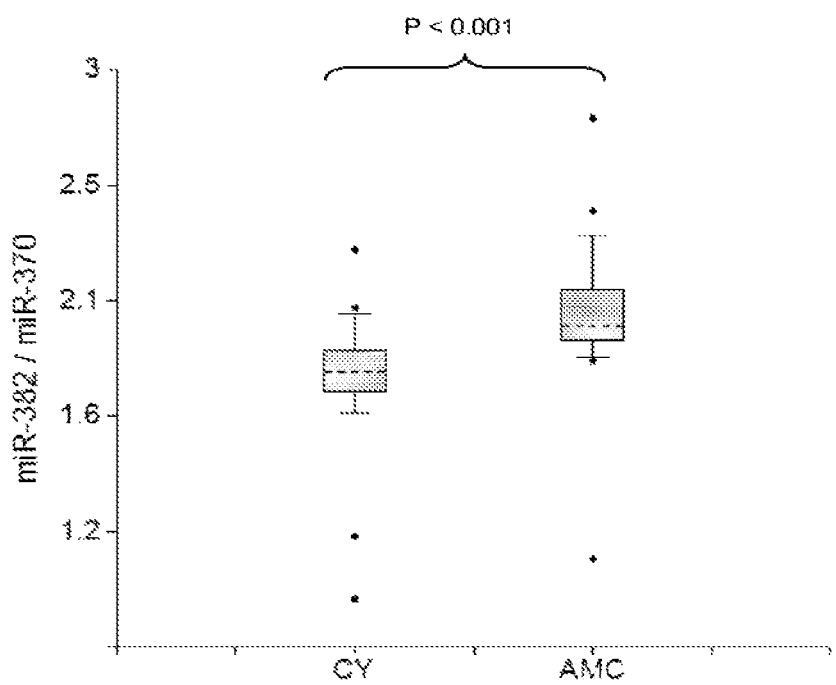
Figure 18G:
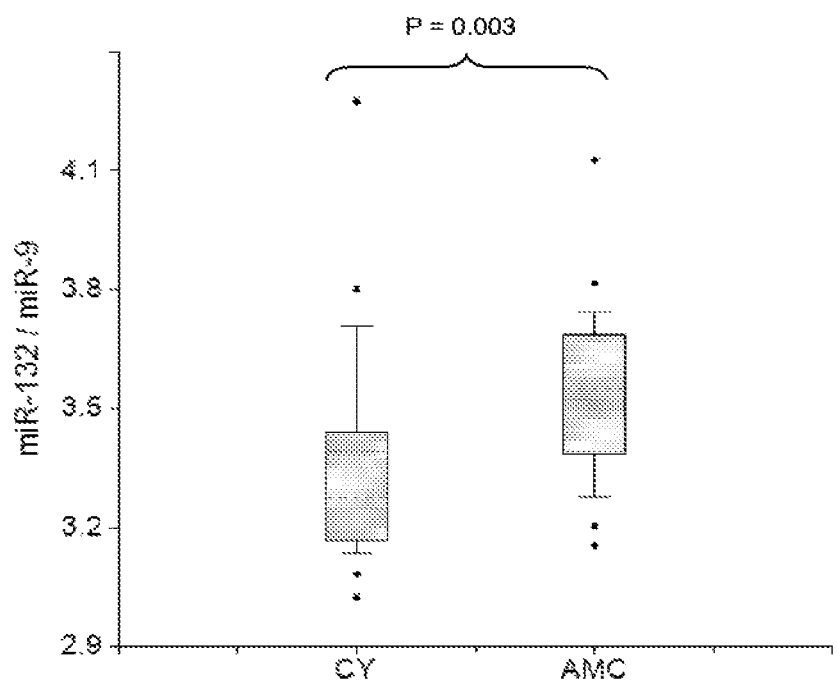
Figure 18H:
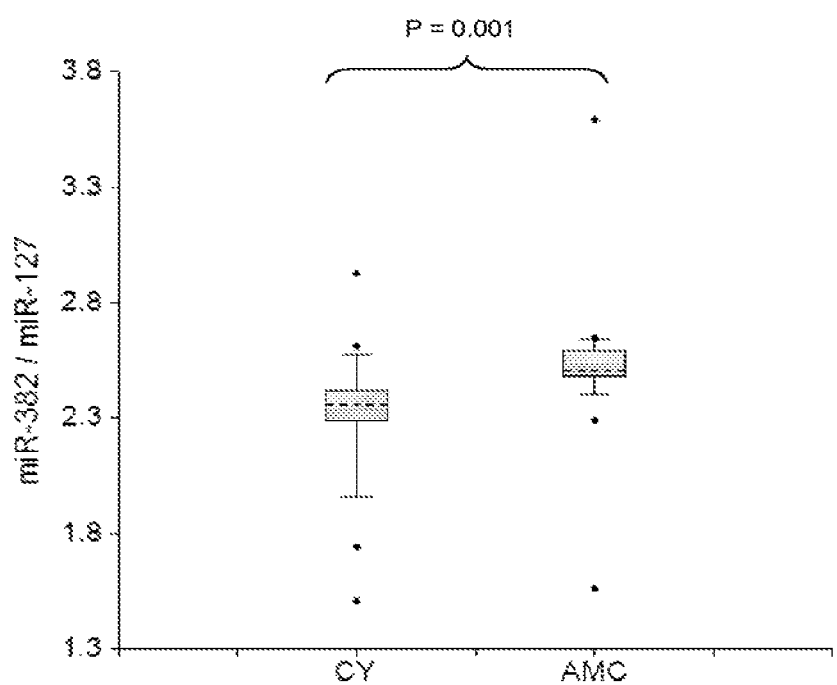
Figure 18I:
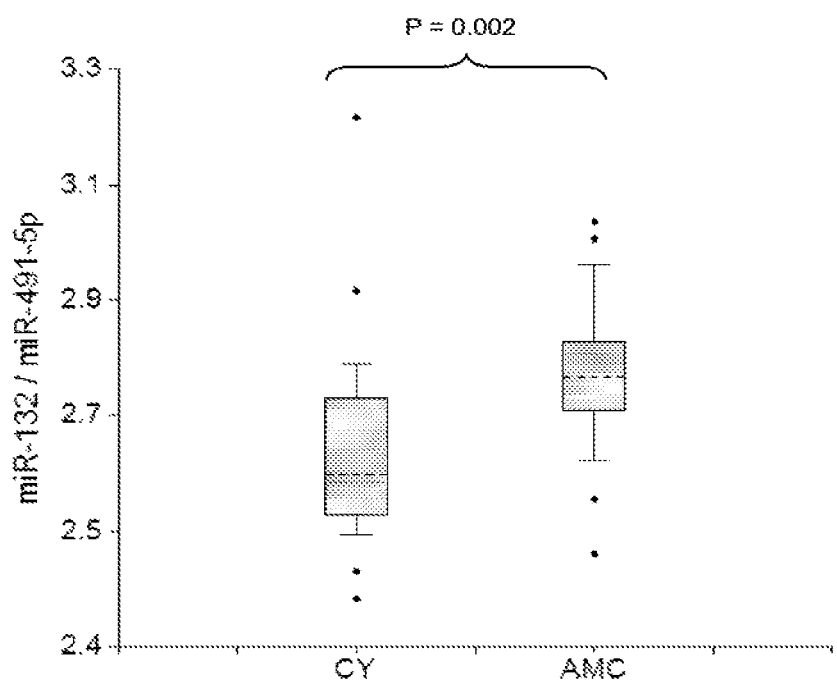
Figure 18J:
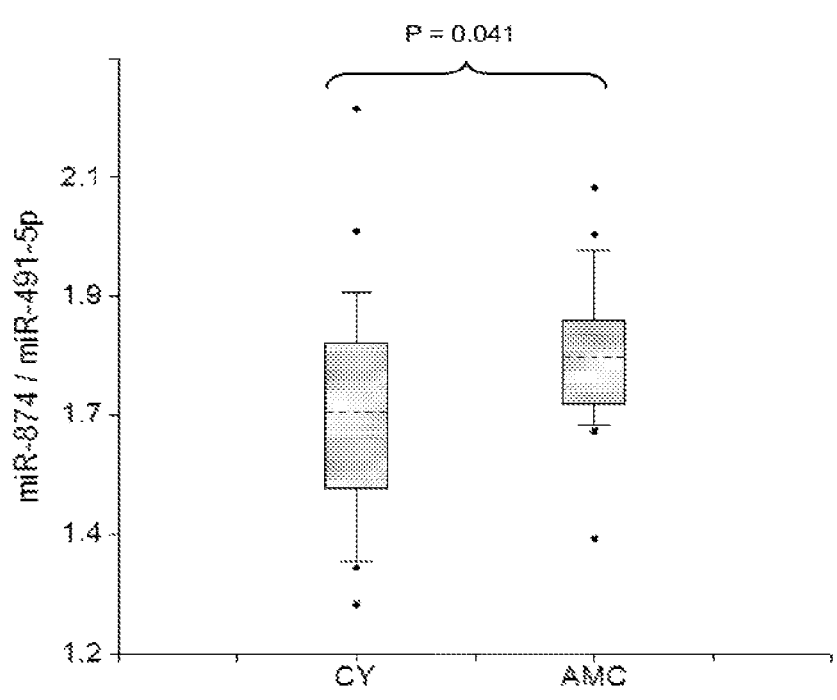

Two families of biomarkers, miR-132 family and miR-134 family, and several normalizers have demonstrated the highest sensitivity and specificity. Biomarkers miR-128, miR-132 and mir-874 ("miR-132 family") demonstrated 84%-92% sensitivity and 84%-90% specificity when normalized per miR-491-5p (FIG. 15A-C). Receiver-Operating Characteristic (ROC) curves for these combinations of biomarkers and the normalizer are presented in FIG. 15A-C. The area under the ROC curve (AUC) for miR-128, miR-132 and miR-874 is 0.95, 0.93 and 0.95, respectively. The second promising set of biomarkers consists of miR-134, miR-323-3p and miR-382 ("miR-134 family") and demonstrates 78%-91% sensitivity and 85-87% specificity when normalized per miR-370 (FIG. 16A-C). AUC for miR-134, miR-323-3p and miR-382 are 091, 0.94 and 0.92, respectively.

Correlation analysis shown in FIG. 17A-F demonstrates that miR-128, miR-132 and miR-874 form one family of biomarkers (Spearman test r values in the pair comparison are in the 0.93-0.95 range) and miR-134, miR-323-p and miR-382 form another family of biomarkers (Spearman test r values in the pair comparison are in the 0.87-0.93 range). High correlation between members of miR-134 family can be easily explained by the fact that all members of this family, namely miR-134, miR-323-3p and miR-382, belong to the same cluster and are expressed in the same cell types (http://www.diana.pcbi.upenn.edu/cgi-bin/miRGen/v3/Cluster.cgi). Close relationships between members of miR-132 family, namely miR-128, miR-132 and miR-874, have not been described before. It is also interesting that biomarker families miR-132 and miR-134 give better results with different normalizers. miR-132 family works better than miR-134 family with normalizers miR-491-5p, miR-181a, miR-9, and miR-141. On the other hand, miR-134 family demonstrates better results than miR-132 family with normalizers miR-370 and miR-127. Correlation between miR-132 and miR-134 biomarker families is relatively low (r values in the pair comparison Spearman test are in the 0.56-0.79 range) indicating that they either reflect distinct pathological processes or are located in different brain areas.

Concentrations of two other neurite/synapse miRNA, miR-7 and miR-125b, when analyzed with any normalizer, were increased in plasma of about 40-50% of MCI patients.

Example 5: Detection of Age-Related Changes in Plasma Concentrations of Neurite/Synapse miRNA There are a number of common processes, e.g. neurite and synapse destruction and finally neuronal death, although on a smaller scale and caused by different factors, characteristic of normal aging and MCI/AD development. Since MCI is detectable by the approach proposed in current invention, it was of interest to investigate whether normal aging could be analyzed and monitored using the same miRNA biomarkers and normalizers.

Plasma samples from Group 1 (21-50 years old) and Group 2 (76-86 years old) subjects with normal cognitive functions, 20 samples in each group, were used in the study. RNA was isolated from two 200 μl aliquots of plasma samples by the Trizol-silica method according to an Asuragen procedure. Single target TaqMan® miRNA qRT-PCR assays (Applied Biosystems) were run using 2 μl plasma equivalents in triplicate in a reaction volume of 10 μl for final PCR for measuring concentration of a neurite/synapse miRNA biomarker as well as levels of a normalizer miRNA selected as described in Example 3.

Data presented in FIG. 18A-J demonstrate that median concentrations of neurite/synapse miRNA biomarkers described in Example 4, such as miR-128, miR-132, miR-874, miR-134, miR-323-3p, or miR-382, after normalization per various brain-enriched miRNA normalizers, such as miR-9, miR-181a, miR-370, or miR-491-5p, are 40-60% higher in the plasma of Group 2 subjects when compared with those from Group 1. Thus, one can expect that prospective longitudinal analysis of neurite/synapse miRNAs and miRNA normalizers in subject bodily fluids will provide important information on brain processes associated with his/her normal aging. This also means that the two biomarker families detect neuronal processes that are common for normal aging and MCI development, such as neurite and synapse destruction.

Neurite/synapse miR-7 and miR-125b (FIG. 18) as well as miR-451, independent of miRNA normalizer used, are not increased during aging and, thus, do not differentiate between two groups.

Figure 19:
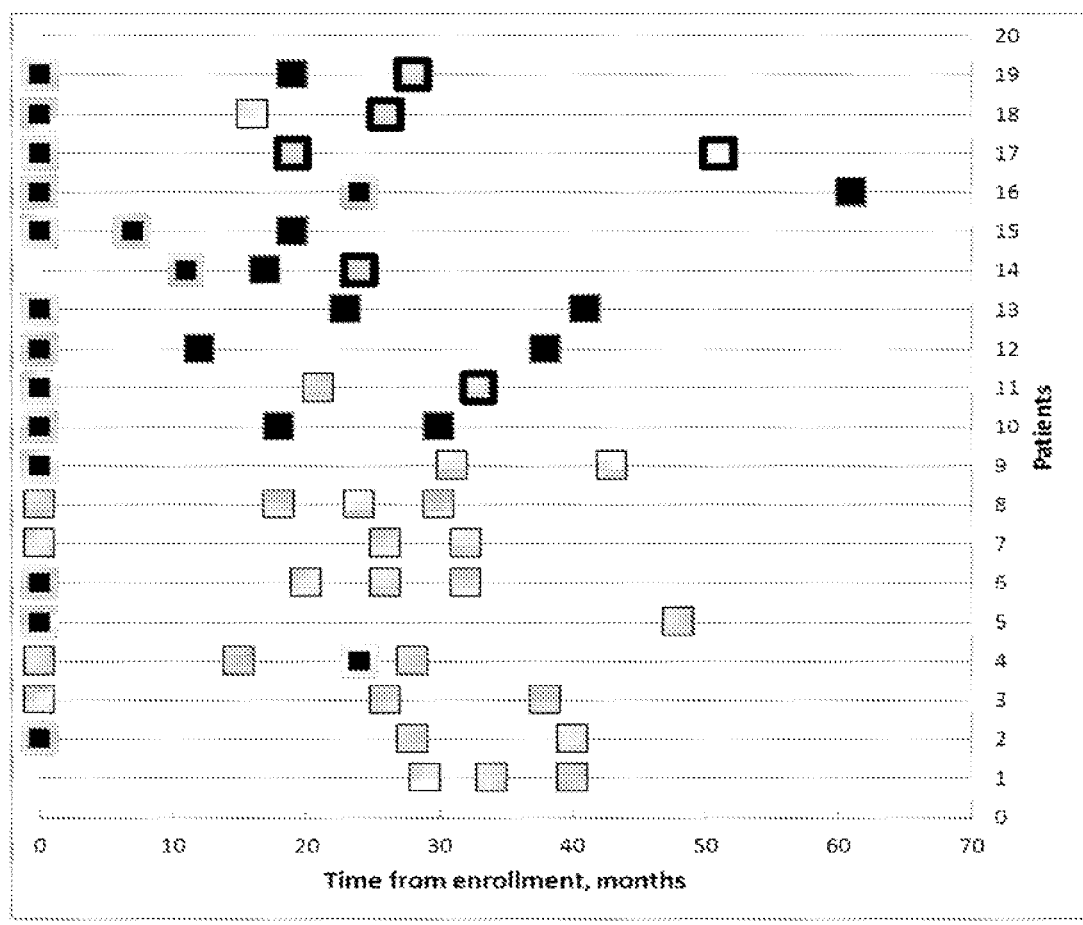
FIG. 19 presents analysis of concentrations of biomarkers in the plasma of elderly subjects with initially normal cognitive function over the course of 2-5 years. Levels of miR-128, miR-132 and miR-874 (biomarkers) were measured and normalized per miR-491-5p. Patients were considered pathology-positive if concentrations of at least two of the three biomarkers were higher than control values predetermined as cutoff points from ROC curves (FIG. 15). Grey and black colors indicate control and pathology, respectively. Small boxes provide results of the plasma miRNA test, and outer colors represent clinical diagnosis; thus, two colors are seen only for cases, in which clinical diagnosis differs from the predictions of the current method.
Figure 20A:
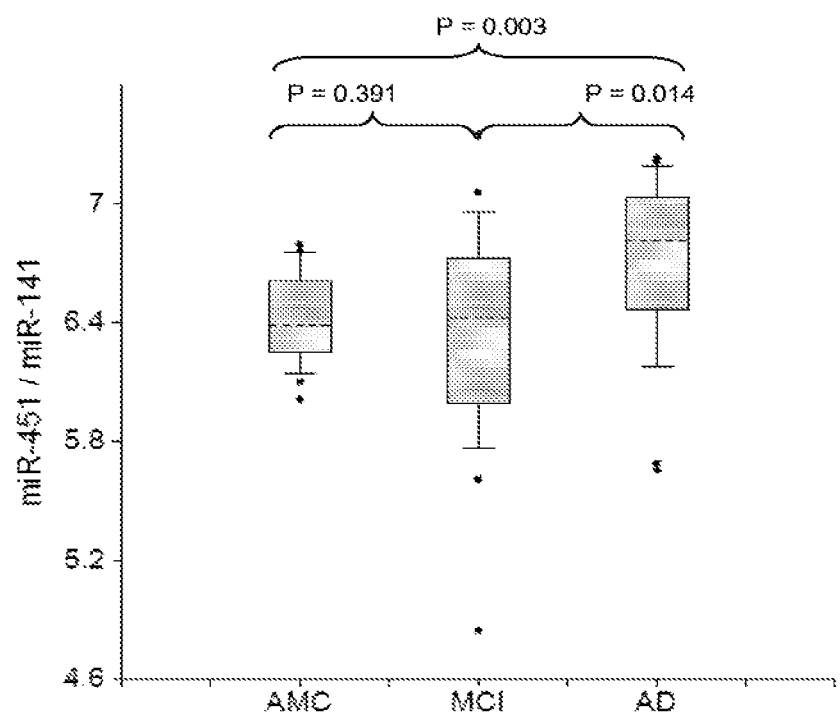
Figure 20B:
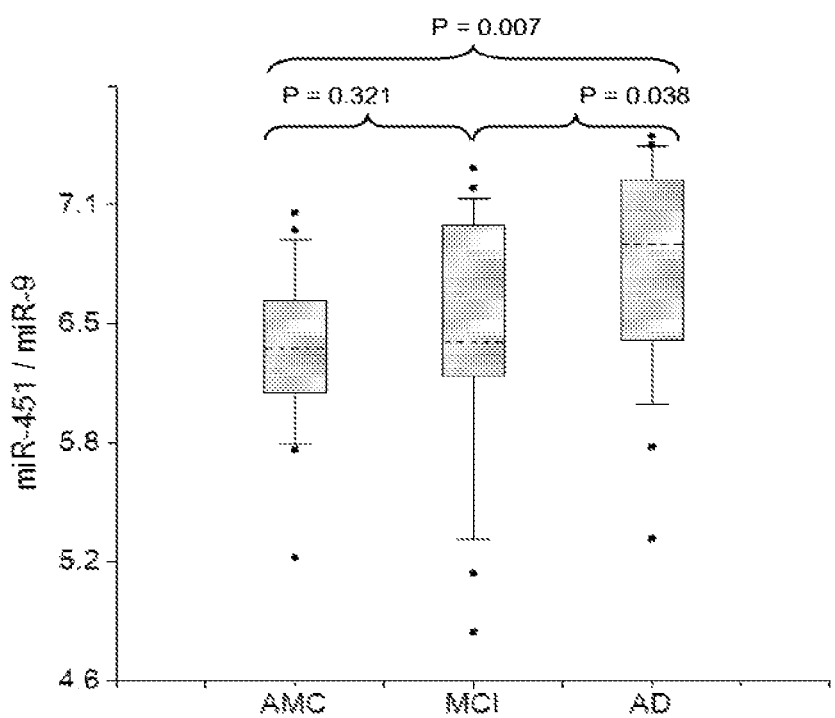
Figure 20C:
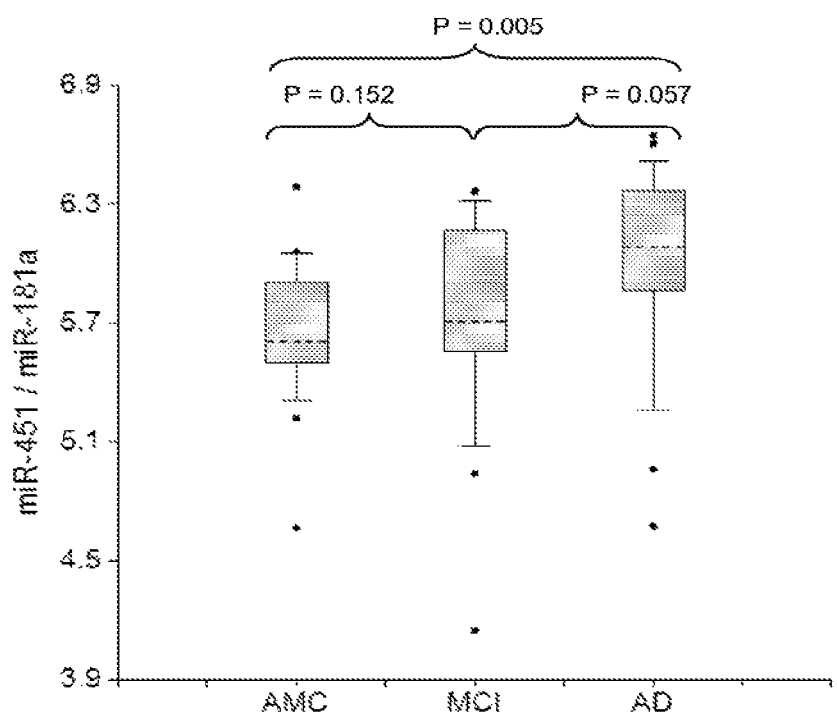
Figure 20D:
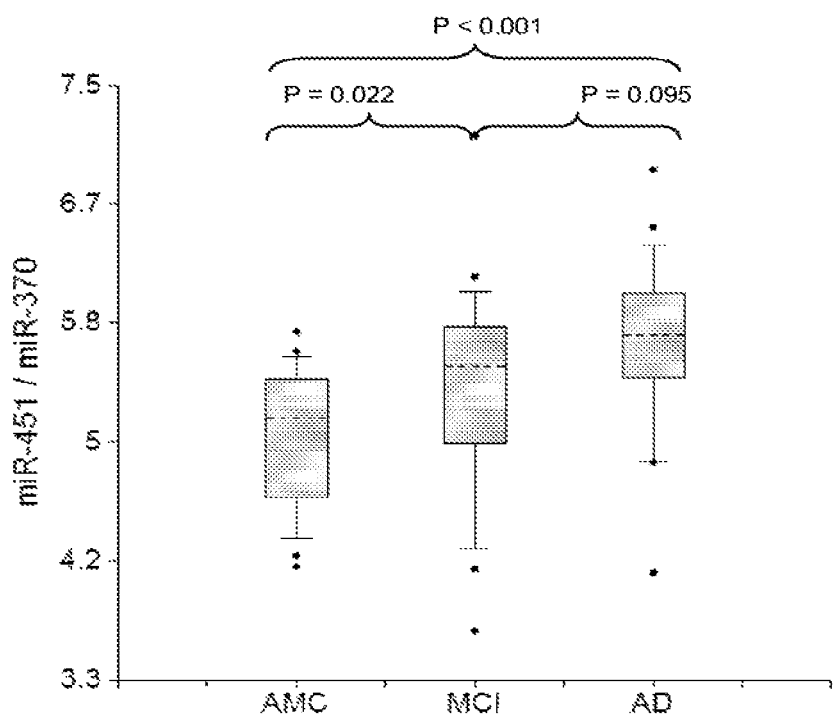
Figure 20E:
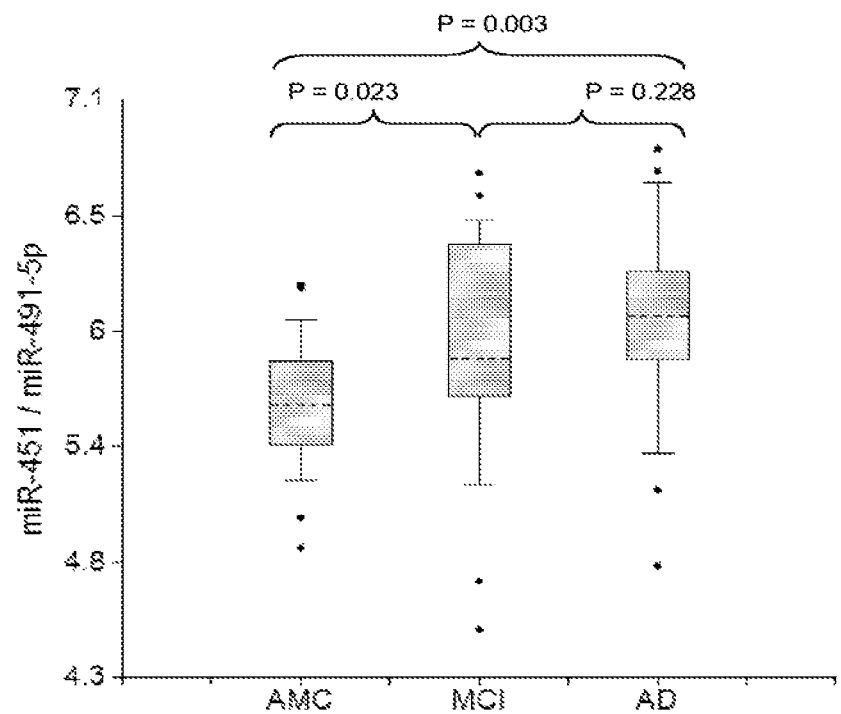
Figure 20F:
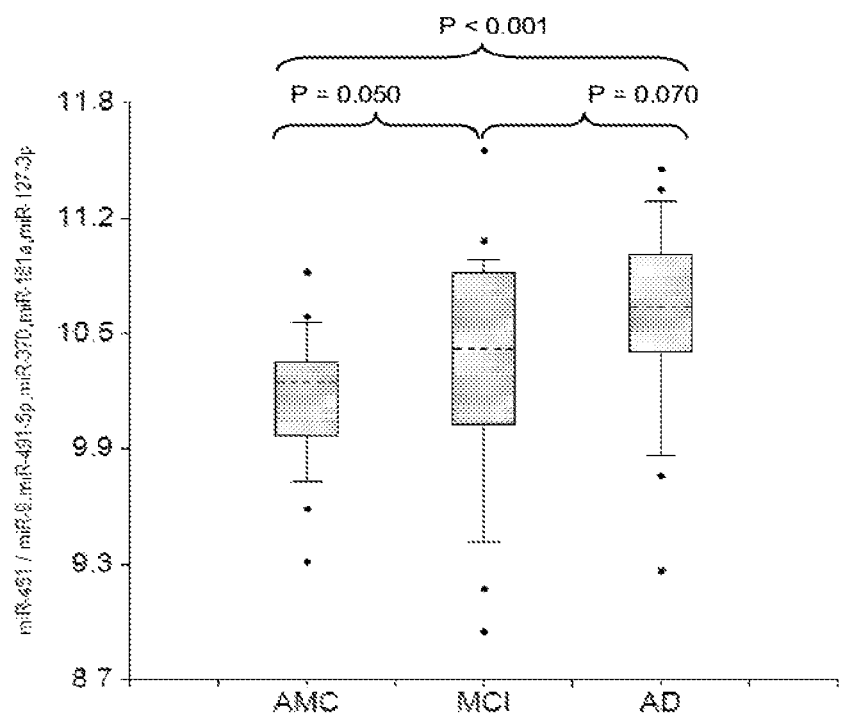
Figure 20G:
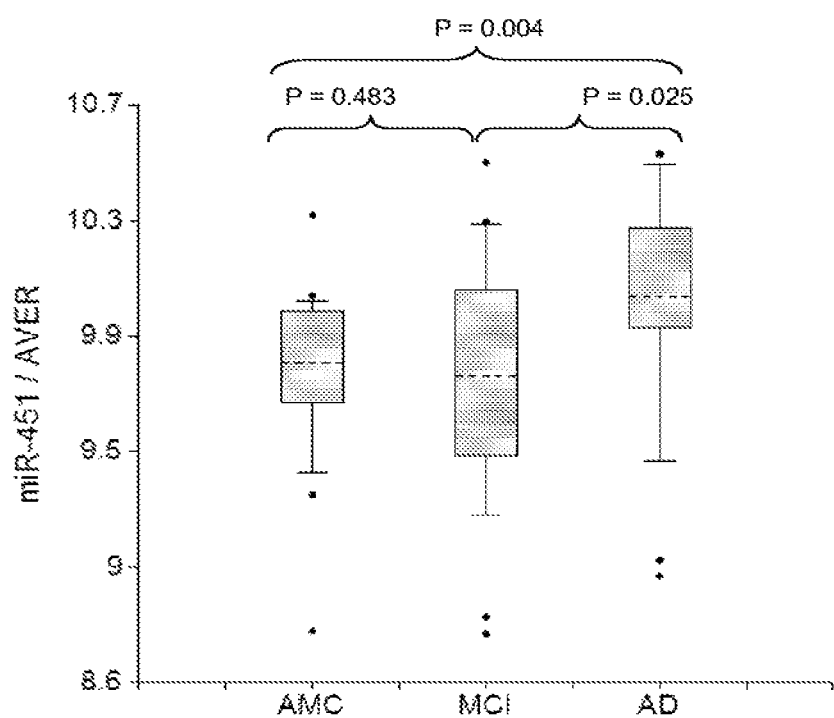

Example 6: Retrospective Longitudinal Study of MCI Development in Elderly Patients with Normal Cognitive Functions at Enrollment ≥70 years old subjects with normal cognitive functions were enrolled in the study. The dynamics of their cognitive function impairment had been investigated and plasma samples had been collected periodically for 4-5 years. Some subjects during this period remained MCI free and others progressed to MCI. miRNAs were extracted and analyzed as described in Example 4. Concentrations of neurite and/or synapse miR-128, miR-132 and miR-874 were measured and normalized per miR-491-5p. Patients were considered MCI-positive if concentrations of at least two of three biomarkers were higher than predetermined control values. Data presented in FIG. 19 demonstrate that in 70% cases the increase in plasma biomarker miRNA is detectable in pre-symptomatic disease stage starting from patient enrollment, which preceded MCI diagnosis by 1 to 5 years.

Example 7: Detection of MCI Transition to Dementia Stage of AD miR-451, which although is not brain-enriched is present in neurite and synapses and is secreted significantly more effectively from pathologic cells, was also included in the study.

FIG. 20 shows that the median concentration of miR-451 is slightly higher in plasma of MCI and is significantly (2-4 times) increased in plasma of AD patients when compared to age-matched controls. Ratios of miR-451 to neurite/synapse miRNA biomarkers concentrations differentiate MCI and AD populations even better (FIG. 21). At the same time in about 40-50% MCI patients this parameter is not distinguishable from that in AD patients, which indicates that these MCI patients will progress to the AD dementia. Thus, consecutive measurements of miR-451 concentration, particularly in combination with neurite/synapse miRNA, in plasma can be used as a marker of MCI-AD progression.

Since miR-7 and miR-125b also detect as pathologic about 40-50% of MCI patients (Example 4) and as miR-451 do not distinguish between young and old subjects (Example 5), these biomarkers were compared with miR-451. miR-16, which surprisingly behaved very similar to miR-7 in all experiments, was also included in the study. 2D graphs in FIG. 22 compare concentrations of these miRNA in plasma of MCI patients and age-matched controls after normalization per miR-491-5p. In all cases there is a group of MCI patients with higher plasma concentrations of both compared miRNA. Similar data were obtained when biomarker miRNA were normalized per the average of 5 brain-enriched normalizer miRNA (FIG. 23). FIG. 24 combines data presented in FIGS. 21-23 and demonstrates that practically the same patients are detected as pathologic (MCI, which will progress to the AD dementia) by described approaches.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for identifying a compound useful for slowing down the progression of or treating pre-MCI or MCI, which method comprises:
   a. measuring the level of at least one synapse or neurite miRNA in one or more bodily fluid samples collected from a subject having pre-MCI or MCI, wherein the synapse or neurite miRNA is selected from the group consisting of miR-7, miR-125b, miR-128, miR-132, miR-874, miR-134, miR-323-3p, and miR-382, wherein said bodily fluid sample(s) is collected prior to test compound administration and wherein the bodily fluid is selected from the group consisting of blood plasma, serum, urine, and saliva;
   b. measuring the level of a normalizer miRNA in the same bodily fluid sample(s) as in step (a), wherein the normalizer miRNA is selected from the group consisting of miR-9, miR-181a, miR-127-3p, miR-370, miR-141, and miR-491-5p;
   c. calculating the ratio of the level of the synapse or neurite miRNA measured in step (a) to the level of the normalizer miRNA measured in step (b) for each of the bodily fluid samples collected from the subject prior to a test compound administration;
   d. measuring the level of the same synapse or neurite miRNA(s) as in step (a) in one or more bodily fluid samples collected from the subject following administration of the test compound, wherein the bodily fluid is selected from the group consisting of blood plasma, serum, urine, and saliva;
   e. measuring the level of the same normalizer miRNA as in step (b) in the same bodily fluid sample(s) as in step (d);
   f. calculating the ratio of the level of the synapse or neurite miRNA measured in step (d) to the level of the normalizer miRNA measured in step (e) for each of the bodily fluid samples collected from the subject following administration of the test compound;
   g. comparing the ratios of the levels of the miRNAs calculated in steps (c) and (f), and
   h. (i) identifying the test compound as a candidate compound for slowing down the progression of or treating pre-MCI or MCI if the ratio of the levels of the miRNAs calculated in step (f) is lower than the ratio of the levels of the miRNAs calculated in step (c); (ii) identifying the test compound as not a candidate compound for slowing down the progression of or treating pre-MCI or MCI if the ratio of the levels of the miRNAs calculated in step (f) is not lower than the ratio of the levels of the miRNAs calculated in step (c).

2. The method of claim 1, wherein the synapse or neurite miRNA is selected from the group consisting of miR-128, miR-132, miR-874, miR-134, miR-323-3p, and miR-382.

3. The method of claim 1, wherein the normalizer miRNA is selected from the group consisting of miR-9, miR-181a, miR-127-3p, miR-370, and miR-491-5p.

4. The method of claim 1, comprising measuring the level of two or more synapse or neurite miRNAs.

5. The method of claim 1, wherein said method comprises the step of administering the test compound to the subject.

6. The method of claim 1, which method comprises a step of collecting the bodily fluid sample from the subject prior to steps (a) and (d).

7. The method of claim 1, wherein the levels of the miRNAs are determined using RT-PCR.

8. The method of claim 1, wherein, prior to measuring miRNA levels, the miRNAs are purified from the bodily fluid sample.

9. The method of claim 1, which method comprises a step of reducing or eliminating degradation of the miRNAs.

10. A method for determining the effectiveness of a pre-MCI or MCI treatment in a subject, which method comprises:
   a. measuring the level of at least one synapse or neurite miRNA in one or more bodily fluid samples collected from the subject prior to initiation of the treatment, wherein the synapse or neurite miRNA is selected from the group consisting of miR-7, miR-125b, miR-128, miR-132, miR-874, miR-134, miR-323-3p, and miR-382 and wherein the bodily fluid is selected from the group consisting of blood plasma, serum, urine, and saliva;
   b. measuring the level of a normalizer miRNA in the same bodily fluid sample(s) as in step (a), wherein the normalizer miRNA is selected from the group consisting of miR-9, miR-181a, miR-127-3p, miR-370, miR-141, and miR-491-5p;
   c. calculating the ratio of the level of the synapse or neurite miRNA measured in step (a) to the level of the normalizer miRNA measured in step (b) for each of the bodily fluid samples collected from the subject prior to initiation of the treatment;
   d. measuring the level of the same synapse or neurite miRNA as in step (a) in one or more bodily fluid samples collected from the subject in the course of or following the treatment, wherein the bodily fluid is selected from the group consisting of blood plasma, serum, urine, and saliva;

e. measuring the level of the same normalizer miRNA as in step (b) in the same bodily fluid sample(s) as in step (d);

f. calculating the ratio of the level of the synapse or neurite miRNA measured in step (d) to the level of the normalizer miRNA measured in step (e) for each of the bodily fluid samples collected from the subject in the course of or following the treatment;

g. comparing the ratios of the levels of the miRNAs calculated in steps (c) and (f), and h. (i) determining that the treatment is effective if the ratio of the levels of the miRNAs calculated in step (f) is lower than the ratio of the levels of the miRNAs calculated in step (c); (ii) determining that the treatment is not effective if the ratio of the levels of the miRNAs calculated in step (f) is not lower than the ratio of the levels of the miRNAs calculated in step (c).

11. The method of claim 10, wherein the subject does not have clinical symptoms of dementia.

12. The method of claim 10, wherein the synapse or neurite miRNA is selected from the group consisting of miR-128, miR-132, miR-874, miR-134, miR-323-3p, and miR-382.

13. The method of claim 10, wherein the normalizer miRNA is selected from the group consisting of miR-9, miR-181a, miR-127-3p, miR-370, and miR-491-5p.

14. The method of claim 10, comprising measuring the level of two or more synapse or neurite miRNAs.

15. The method of claim 10, wherein said method comprises the step of administering the treatment to the subject.

16. The method of claim 10, which method comprises a step of collecting the bodily fluid sample from the subject prior to steps (a) and (d).

17. The method of claim 10, wherein the levels of the miRNAs are determined using RT-PCR.

18. The method of claim 10, wherein, prior to measuring miRNA levels, the miRNAs are purified from the bodily fluid sample.

19. The method of claim 10, which method comprises a step of reducing or eliminating degradation of the miRNAs.

* * * * *